United States Patent
Sachdeva et al.

(10) Patent No.: US 12,144,872 B1
(45) Date of Patent: Nov. 19, 2024

(54) MODIFIED NANODELIVERY SYSTEM AND METHOD FOR ENHANCED IN VIVO MEDICAL AND PRECLINICAL IMAGING

(71) Applicant: Florida A&M University, Tallahassee, FL (US)

(72) Inventors: Mandip Sachdeva, Tallahassee, FL (US); Apurva Patel, Longwood, FL (US)

(73) Assignee: Florida A&M University, Tallahassee, FL (US)

( * ) Notice: Subject to any disclaimer, the term of this patent is extended or adjusted under 35 U.S.C. 154(b) by 805 days.

(21) Appl. No.: 17/369,104

(22) Filed: Jul. 7, 2021

Related U.S. Application Data

(60) Division of application No. 15/226,070, filed on Aug. 2, 2016, now Pat. No. 11,090,394, which is a continuation of application No. 13/851,610, filed on Mar. 27, 2013, now abandoned.

(60) Provisional application No. 61/674,449, filed on Jul. 23, 2012, provisional application No. 61/615,977, filed on Mar. 27, 2012.

(51) Int. Cl.
| | | |
|---|---|---|
| *A61B 5/00* | (2006.01) | |
| *A61B 8/00* | (2006.01) | |
| *A61B 8/08* | (2006.01) | |
| *A61B 10/00* | (2006.01) | |
| *A61K 9/127* | (2006.01) | |
| *A61K 47/14* | (2017.01) | |
| *A61K 49/00* | (2006.01) | |

(52) U.S. Cl.
CPC ........ *A61K 49/0084* (2013.01); *A61B 5/0071* (2013.01); *A61B 8/481* (2013.01); *A61K 9/1272* (2013.01); *A61K 47/14* (2013.01); *A61K 49/0032* (2013.01)

(58) Field of Classification Search
None
See application file for complete search history.

(56) References Cited

U.S. PATENT DOCUMENTS

| | | | |
|---|---|---|---|
| 4,775,620 A | 10/1988 | Cardiff et al. | |
| 5,462,059 A | 10/1995 | Ferrara et al. | |
| 5,543,158 A | 8/1996 | Gref et al. | |
| 5,877,175 A | 3/1999 | Sargent et al. | |
| 6,371,917 B1 | 4/2002 | Ferrara et al. | |
| 6,547,731 B1 | 4/2003 | Coleman et al. | |
| 6,875,438 B2 | 4/2005 | Kraemer et al. | |
| 7,358,226 B2 | 4/2008 | Dayton et al. | |
| 8,343,551 B2 | 1/2013 | Makino et al. | |
| 8,647,661 B1 | 2/2014 | Sachdeva et al. | |
| 2003/0079241 A1 | 4/2003 | Cardiff et al. | |
| 2007/0071683 A1 | 3/2007 | Dayton et al. | |
| 2007/0105220 A1 | 5/2007 | Crowe et al. | |
| 2009/0092548 A1 | 4/2009 | Ferrara et al. | |
| 2010/0068260 A1 | 3/2010 | Kruse et al. | |
| 2011/0195030 A1 | 8/2011 | Mumper et al. | |

OTHER PUBLICATIONS

Badr and Tannous. Bioluminescence imaging: progress and applications. Trends Biotechnol. 2011. vol. 29 (No. 12): 624-33.
Berger et al., Uptake kinetics and biodistribution of 14C-D-luciferin-a radiolabeled substrate for the firefly luciferase catalyzed bioluminescence reaction: impact on bioluminescence based reporter gene imaging. Eur J Nucl Med Mol Imaging. 2008. vol. 35: 2275-85.
Bhaumik and Gambhir. Optical imaging of Renilla luciferase reporter gene expression in living mice. Proc Natl Acad Sci U S A. 2002. vol. 99 (No. 1):377-82.
Hsieh et al., A luciferase transgenic mouse model: visualization of prostate development and its androgen responsiveness in live animals. Journal of Molecular Endocrinology. 2005. vol. 35: 293-305.
Cai and Chen. Multimodality molecular imaging of tumor angiogenesis. J Nucl Med. 2008. vol. 49 (Suppl 2): 113S-28S.
Cho et al., Noninvasive multimodality imaging of the tumor microenvironment: registered dynamic magnetic resonance imaging and positron emission tomography studies of a preclinical tumor model of tumor hypoxia. Neoplasia. 2009. vol. 11 (No. 3):247-59, 2p following 59.
Contag and Ross. It's not just about anatomy: in vivo bioluminescence imaging as an eyepiece into biology. J Magn Reson Imaging. 2002. vol. 16: 378-87.
Corn et al., Imaging Early Stage Osteogenic Differentiation of Mesenchymal Stem Cells. J Orthop Res. 2013. vol. 31: 871-879.

(Continued)

*Primary Examiner* — Michael G. Hartley
*Assistant Examiner* — Melissa J Perreira
(74) *Attorney, Agent, or Firm* — Michele L. Lawson; Smith & Hopen, P.A.

(57) ABSTRACT

A lipid-, polymer-, and metal-based system of modified nanostructures of active biomedical and pharmaceutical agents used for in vivo (whole body/organ or tissue-specific) imaging. The modified nanostructure system involves various combinations of excipients (lipids, oils, surfactant, polymers, metals, carbon, nanotubes, etc.) in a formulation that allows a user to: (1) sustain the bioluminescent, fluorescent, or contrast signal for a longer period than conventional systems without repetitive administration (e.g., nanostructure system of luciferin), (2) target specific sites of interest (e.g., organ, tissue, receptors, proteins, etc.) for enhanced imaging of the targeted site (e.g. nanostructure system of XenoLight DIR with CREKA allows imaging of tumor vasculature), and (3) increase bioluminescent, fluorescent, or contrast signal flux.

8 Claims, 31 Drawing Sheets

(56) References Cited

OTHER PUBLICATIONS

Di Carli et al., Clinical myocardial perfusion Pet/Ct. J Nucl Med. 2007. vol. 48: 783-793.
Lassailly et al., Microenvironmental contaminations induced by fluorescent lipophilic dyes used for noninvasive in vitro and in vivo cell tracking. Blood. 2010. vol. 115 (No. 26): 5347-5354.
Frackman et al., Cloning, organization, and expression of the bioluminescence genes of Xenorhabdus luminescens. J Bacteriol. 1990. vol. 172 (No. 10): 5767-5773.
Gross et al., Continuous delivery of D-luciferin by implanted micro-osmotic pumps enables true real-time bioluminescence imaging of luciferase activity in vivo. Mol Imaging. 2007. vol. 6 (No. 2): 121-30.
Gross and Piwnica-Worms. Real-time imaging of ligand-induced IKK activation in intact cells and in living mice. Nat Methods. 2005. vol. 2 (No. 8): 607-614.
Gross and Piwnica-Worms. Spying on cancer: molecular imaging in vivo with genetically encoded reporters. Cancer Cell. 2005. vol. 7: 5-15.
Ao et al., Development and optimization of baicalin-loaded solid lipid nanoparticles prepared by coacervation method using central composite design. Eur J Pharm Sci. 2012. vol. 47: 497-505.
Patel et al., Nanosuspension of efavirenz for improved oral bioavailability: formulation optimization, in vitro, in situ, and in vivo evaluation. Drug Dev Ind Pharm. 2013. Early Online: 1-12.
Hayashi et al., Gastroenteropancreatic neuroendocrine tumors: multimodality imaging features with pathological correlation. Jpn J Radiol. 2011 . vol. 29: 85-91.
Hiler et al., Imaging gene expression in live transgenic mice after providing luciferin in drinking water. Photochem Photobiol Sci. 2006. vol. 5: 1082-5.
Hillner et al., The National Oncologic PET Registry (NOPR): design and analysis plan. J Nucl Med. 2007. vol. 48: 1901-8.
Zhang et al., Application of Quality by Design to the Process Development of Botanical Drug Products: A Case Study. AAPS PharmSciTech. 2013. vol. 14 (No. 1): 277-286.
Jenkins et al., Bioluminescent human breast cancer cell lines that permit rapid and sensitive in vivo detection of mammary tumors and multiple metastases in immune deficient mice. Breast Cancer Res. 2005. vol. 7 (No. 4): 444-454.
Jenkins et al., Bioluminescent imaging (BLI) to improve and refine traditional murine models of tumor growth and metastasis. Clinical and Experimental Metastasis. 2003. vol. 20: 733-744.
Jenning et al., Vitamin A—Loaded Solid Lipid Nanoparticles for Topical use: Drug Release Properties. J. Control. Release. 2000. vol. 66: 115-126.
Kakkar et al., Curcumin loaded solid lipid nanoparticles: an efficient formulation approach for cerebral ischemic reperfusion injury in rats. Eur J Pharm Biopharm. 2013. vol. 85: 339-345.
Kheirolomoom et al., Enhanced in vivo bioluminescence imaging using liposomal luciferin delivery system. J Control Release. 2010. vol. 141: 128-36.
Singh et al., Nanocarrier based formulation of Thymoquinone improves oral delivery: Stability assessment, in vitro and in vivo studies. Colloid and Surfaces B: Biointerfaces. 2013. vol. 102: 822-832.
Lim et al., Monitoring tumor metastases and osteolytic lesions with bioluminescence and micro CT imaging. J Vis Exp. 2011. Issue 50. e2775: 1-3.
Lim et al., In vivo bioluminescent imaging of mammary tumors using IVIS spectrum. J Vis Exp. 2009. Issue 26: e1210: 1-2.
Mosconi et al., Multicenter standardized 18F-FDG Pet diagnosis of mild cognitive impairment, Alzheimer's disease, and other dementias. J Nucl Med. 2008. vol. 49 (No. 3):390-8.
Muller et al., Nanostructured lipid matrices for improved microencapsulation of drugs. Int J Pharm. 2002. vol. 242: 121-8.
Muller et al., Cytotoxicity of Solid Lipid Nanoparticles as a Function of the Lipid Matrix and the Surfactant. Pharm. Res. 1997. vol. 14 (No. 4): 458-462.

Niu and Chen. Has molecular and cellular imaging enhanced drug discovery and drug development? Drugs R D. 2008. vol. 9 (No. 6): 351-68.
Pardeike et al., Lipid nanoparticles (SLN, NLC) in cosmetic and pharmaceutical dermal products. Int J Pharm. 2009. vol. 366: 170-84.
Kaleemuddin and Srinivas. Lyophilized Oral Sustained Release Polymeric Nanoparticles of Nateglinide. AAPS PharmSciTech. 2013. vol. 14 (No. 1): 78-85.
Patlolla et al., Formulation, characterization and pulmonary deposition of nebulized celecoxib encapsulated nanostructured lipid carriers. J Control Release. 2010. vol. 144: 233-41.
Puglia et al., Lipid nanoparticles for prolonged topical delivery: an in vitro and in vivo investigation. Int J Pharm. 2008. vol. 357: 295-304.
Sadikot and Blackwell. Bioluminescence: Imaging. Proc Am Thorac Soc. 2005. vol. 2: 537-40.
Schwarz and Mehnert. Freeze-drying of drug-free and drug-loaded solid lipid nanoparticles (SLN). Int J Pharm. 1997. vol. 157: 171-9.
Shan et al., Dual probe with fluorescent and magnetic properties for imaging solid tumor xenografts. Molecular Imaging. 2007. vol. 6 (No. 2): 85-95.
Chalikwar et al., Formulation and evaluation of Nimodipine-loaded solid lipid nanoparticles delivered via lymphatic transport system. Colloids and Surfaces B: Biointerfaces. 2012. vol. 97: 109-116.
Singh et al., Developing micro-/nanoparticulate drug delivery systems using "design of experiments". Int J Pharm Investig. 2011. vol. 1 (No. 2): 75-87.
Siragusa et al., Real-time monitoring of *Escherichia coli* O157:H7 adherence to beef carcass surface tissues with a bioluminescent reporter. Appl Environ Microbiol. 1999. vol. 65 (No. 4): 1738-45.
Souto et al., Development of a controlled release formulation based on SLN and NLC for topical clotrimazole delivery. Int J Pharm. 2004. vol. 278: 71-7.
Park et al., Quality by design: screening of critical variables and formulation optimization of Eudragit E nanoparticles containing dutasteride. Arch. Pharm. Res. 2013.
Snoeks et al., 'In vivo' optical approaches to angiogenesis imaging. Angiogenesis. 2010. vol. 13: 135-147.
Venkateswarlu and Manjunath. Preparation, characterization and in vitro release kinetics of clozapine solid lipid nanoparticles. J Control Release. 2004. vol. 95: 627-38.
Willmann et al., Molecular imaging in drug development. Nat Rev Drug Discov. 2008. vol. 7: 591-607.
Wissing et al., Investigations on the Occlusive Properties of Solid Lipid Nanoparticles (SLN), J. Cosmet. Sci. 2001. vol. 52: 313-323.
Xiang et al. Lung-targeting delivery of dexamethasone acetate loaded solid lipid nanoparticles. Arch Pharm Res. 2007. vol. 30 (No. 4): 519-25.
Hakamata et al., Firefly Rats as an Organ/Cellular Source for Long-Term In Vivo Bioluminescent Imaging. Transplantation. 2006. vol. 81: 1179-1184.
Zhang et al. Visualization of Mitotic Arrest of Cell Cycle with Bioluminescence Imaging in Living Animals. Mol Imaging Biol. 2013. vol. 15: 431-440.
Zhang et al., A spontaneous acinar cell carcinoma model for monitoring progression of pancreatic lesions and response to treatment through noninvasive bioluminescence imaging. Clin Cancer Res. 2009. vol. 15:4915-24.
Zhang et al., Rapid in vivo functional analysis of transgenes in mice using whole body imaging of luciferase expression. Transgenic Res. 2001. vol. 10: 423-34.
Zhao et al., Imaging surrogates of tumor response to therapy: anatomic and functional biomarkers. J Nucl Med. 2009. vol. 50 (No. 2): 239-49.
Zinn et al. Noninvasive bioluminescence imaging in small animals. ILAR J. 2008. vol. 49 (No. 1): 103-15.
Zhao et al., Emission spectra of bioluminescent reporters and interaction with mammalian tissue determine the sensitivity of detection in vivo. J Biomed Opt. 2005. vol. 10 (No. 4): 1-9.
Hargreaves. The role of molecular imaging in drug discovery and development. Clin Pharmacol Ther. 2008. vol. 83 (No. 2): 349-53.

(56) References Cited

OTHER PUBLICATIONS

Jenkins et al. Luciferase-expressing MCF-7-luc-F5 human breast cancer cells used to monitor mammary fat pad tumor growth and metastasis in vivo in nude-beige mice. Proceedings of the American Association for Cancer Research 2004. vol. 45: Abstract.

Patel et al., Opening Up the Optical Imaging Window Using Nano-Luciferin. Pharm Res. 2014. vol. 31: 3073-3084.

Pietkiewicz et al., The choice of lipids and surfactants for injectable extravenous microspheres. Pharmazie. 2004. 325-326.

Chougule et al. Abstract 5511: Multifunctional CREKA peptide conjugated lipid nanocarriers of synergistically acting Noscapine and Doxorubicin for breast cancer therapy. Cancer Research 2010, Proceedings: AACR 101st Annual Meeting 2010—Apr. 17-21, 2010; Washington, D.C.

Fang et al. Tryptanthrin-Loaded Nanoparticles for Delivery into Cultured Human Breast Cancer Cells, MCF7: the Effects of Solid Lipid/Liquid Lipid Ratios in the Inner Core. Chem. Pharm. Bull. 59(2) 266-271 (2011).

Ichite et al. Enhancement of Docetaxel Anticancer Activity by a Novel Diindolylmethane Compound in Human Non-Small Cell Lung Cancer. Clin. Cancer Res. 2009; 15(2), Jan. 15, 2009.

Kasongo et al. Selection and Characterization of Suitable Lipid Excipients for use in the Manufacture of Didanosine-Loaded Solid Lipid Nanoparticles and Nanostructured Lipid Carriers. Journal of Pharmaceutical Sciences, vol. 100, No. 12, Dec. 2011, pp. 5185-5196.

Liu et al. Tumor Specific Delivery and Therapy by Double-Targeted Nanostructured Lipid Carriers with Anti-VEGFR-2 Antibody. Mol. Pharm. 2011, 8, 2291-2301.

Patlolla et al. Translocation of cell penetrating peptide engrafted nanoparticles across skin layers. Biomaterials 31 (2010) 5598-5607.

MODIFIED NANODELIVERY SYSTEM AND METHOD FOR ENHANCED IN VIVO MEDICAL AND PRECLINICAL IMAGING

CROSS-REFERENCE TO RELATED APPLICATIONS

This application is a divisional of and claims priority to currently pending U.S. Nonprovisional application Ser. No. 15/226,070, entitled "Modified Nanodelivery System and Method for Enhanced In Vivo Medical and Preclinical Imaging", filed Aug. 2, 2016, which is a continuation of and claims priority to U.S. Nonprovisional patent application Ser. No. 13/851,610, entitled "Modified Nanodelivery System and Method for Enhanced In Vivo Medical and Preclinical Imaging", filed on Mar. 27, 2013 by the same inventors, which claims priority to U.S. Provisional Patent Application No. 61/674,449, entitled "Novel Nano-Delivery System for Medical Imaging and Preclinical Imaging", filed on Jul. 23, 2012 by the same inventors, and also claims priority to U.S. Provisional Patent Application No. 61/615,977, entitled "Enhanced In Vivo Imaging of Tumors Using Modified Nanodelivery System", filed on Mar. 27, 2012 by the same inventors, all of which are incorporated herein by reference in their entireties.

BACKGROUND OF THE INVENTION

1. Field of the Invention

This invention relates, generally, to in vivo imaging. More specifically, it relates to a system and method of delivering of an active substance to a targeted tissue (and formulations thereof) to enhance in vivo medical and preclinical imaging in animals and humans.

2. Brief Description of the Prior Art

Imaging techniques have been used in medical practice and clinical trial (1-4) for non-invasive diagnosis of disease and progression of treatments. Medical imaging is the technique and process used to create images of the human body (or parts and function thereof) for clinical purposes (medical procedures seeking to reveal, diagnose or examine disease) or medical science (including the study of normal anatomy and physiology). Various imaging techniques are known in the art.

Radiography: Two forms of radiographic images are in use in medical imaging, fluoroscopy and projection radiography. Fluoroscopy produces real-time images of internal structures of the body in a similar fashion to radiography, but employs a constant input of X-rays, at a lower dose rate. Contrast media, such as barium, iodine, and air are used to visualize internal organs as they work. Fluoroscopy is also used in image-guided procedures when constant feedback during a procedure is required.

An image receptor is required to convert the radiation into an image after it has passed through the area of interest. Initially, this image receptor was a fluorescing screen, which advanced to an Image Amplifier (IA), a large vacuum tube that had the receiving end coated with cesium iodide and a mirror at the opposite end. Eventually, the mirror was replaced with a TV camera. Projectional radiographs, more commonly known as X-rays, are often used to determine the type and extent of a fracture as well as for detecting pathological changes in the lungs. With the use of radio-opaque contrast media, such as barium, they can also be used to visualize the structure of the stomach and intestines—this can help diagnose ulcers or certain types of colon cancer.

Magnetic resonance imaging (MRI): A magnetic resonance imaging instrument (MRI scanner), or nuclear magnetic resonance (NMR) imaging scanner as it was originally known, uses powerful magnets to polarize and excite hydrogen nuclei (single proton) in water molecules in human tissue, producing a detectable signal which is spatially encoded, resulting in images of the body. The MRI machine emits a radio frequency (RF) pulse that specifically binds only to hydrogen. The system sends the pulse to the area of the body to be examined. The pulse makes the protons in that area absorb the energy needed to make them spin in a different direction. This is the "resonance" part of MRI. The RF pulse makes them (only the one or two extra unmatched protons per million) spin at a specific frequency, in a specific direction. The particular frequency of resonance is known as the Larmour frequency and is calculated based on the particular tissue being imaged and the strength of the main magnetic field. MRI uses three electromagnetic fields: (1) a very strong (on the order of units of tesla) static magnetic field to polarize the hydrogen nuclei, called the static field; (2) a weaker time-varying (on the order of 1 kHz) field(s) for spatial encoding, called the gradient field(s); and (3) a weak RF field for manipulation of the hydrogen nuclei to produce measurable signals, collected through an RF antenna.

The most commonly used intravenous contrast agents are based on chelates of gadolinium. In general, these agents have proved safer than the iodinated contrast agents used in X-ray radiography or CT. Anaphylactoid reactions are rare, occurring in approximately 0.03-0.1% of patients. Of particular interest is the lower incidence of nephrotoxicity, compared with iodinated agents, when given at usual doses—this has made contrast-enhanced MRI scanning an option for patients with renal impairment, who would otherwise not be able to undergo contrast-enhanced CT.

Although gadolinium agents have proved useful for patients with renal impairment, in patients with severe renal failure requiring dialysis there is a risk of a rare but serious illness, nephrogenic systemic fibrosis that may be linked to the use of certain gadolinium-containing agents. The most frequently linked agent is gadodiamide, but other agents have been linked as well. Although a causal link has not been definitively established, current guidelines in the U.S. are that dialysis patients should only receive gadolinium agents where essential, and that dialysis should be performed as soon as possible after the scan to remove the agent from the body promptly. In Europe, where more gadolinium-containing agents are available, a classification of agents according to potential risks has been released. Recently, a new contrast agent named gadoxetate, brand name Eovist (US) or Primovist (EU) was approved for diagnostic use—this has the theoretical benefit of a dual excretion path.

Additionally, phosphate-based compounds, such as disodium etidronate, tin pyrophosphate, polyphosphate, and sodium trimetaphosphate, are used as imaging agents for bone and cartilages.

Fiduciary Markers: Fiduciary markers are used in a wide-range of medical imaging applications. Images of the same subject produced with two different imaging systems may be correlated (called image registration) by placing a fiduciary marker in the area imaged by both systems. In this case, a marker that is visible in the images produced by both imaging modalities must be used. By this method, functional information from SPECT or positron emission tomography can be related to anatomical information provided by magnetic resonance imaging (MRI). Similarly, fiducial points established during MRI can be correlated with brain images generated by magnetoencephalography to localize the source of brain activity.

Nuclear medicine: Nuclear medicine encompasses both diagnostic imaging and treatment of disease, and may also be referred to as molecular medicine or molecular imaging and therapeutics. Nuclear medicine uses certain properties of isotopes and the energetic particles emitted from radioactive material to diagnose or treat various pathology. Different from the typical concept of anatomic radiology, nuclear medicine enables assessment of physiology. This function-based approach to medical evaluation has useful applications in most subspecialties, notably oncology, neurology, and cardiology.

Gamma cameras are used, for example in scintigraphy, SPECT and PET, to detect regions of biologic activity that may be associated with disease. Relatively short lived isotope, such as 123I, is administered to the patient. Isotopes are often preferentially absorbed by biologically active tissue in the body, and can be used to identify tumors or fracture points in bone. Images are acquired after collimated photons are detected by a crystal that gives off a light signal, which is in turn amplified and converted into count data.

Scintigraphy ("scint") is a form of diagnostic test wherein radioisotopes are taken internally, for example intravenously or orally. Then, gamma cameras capture and form two-dimensional images from the radiation emitted by the radiopharmaceuticals.

SPECT is a 3D tomographic technique that uses gamma camera data from many projections and can be reconstructed in different planes. A dual detector head gamma camera combined with a CT scanner, which provides localization of functional SPECT data, is termed a SPECT/CT camera, and has shown utility in advancing the field of molecular imaging. In most other medical imaging modalities, energy is passed through the body and the reaction or result is read by detectors. In SPECT imaging, the patient is injected with a radioisotope, most commonly Thallium 201Tl, Technetium 99mTC, Iodine 123I, and Gallium 67Ga. The radioactive gamma rays are emitted through the body as the natural decaying process of these isotopes takes place. The emissions of the gamma rays are captured by detectors that surround the body. This essentially means that the human is now the source of the radioactivity, rather than the medical imaging device, such as X-Ray or CT.

Positron emission tomography (PET) uses coincidence detection to image functional processes. Short-lived positron emitting isotope, such as 18F, is incorporated with an organic substance such as glucose, creating F18-fluorodeoxyglucose, which can be used as a marker of metabolic utilization. Images of activity distribution throughout the body can show rapidly growing tissue, like tumor, metastasis, or infection. PET images can be viewed in comparison to computed tomography scans to determine an anatomic correlate. Modern scanners combine PET with a CT, or even MRI, to optimize the image reconstruction involved with positron imaging. This is performed on the same equipment without physically moving the patient off of the gantry. The resultant hybrid of functional and anatomic imaging information is a useful tool in non-invasive diagnosis and patient management.

Photoacoustic imaging: Photoacoustic imaging is a recently developed hybrid biomedical imaging modality based on the photoacoustic effect. It combines the advantages of optical absorption contrast with ultrasonic spatial resolution for deep imaging in (optical) diffusive or quasi-diffusive regime. Recent studies have shown that photoacoustic imaging can be used in vivo for tumor angiogenesis monitoring, blood oxygenation mapping, functional brain imaging, and skin melanoma detection, etc.

Tomography: Tomography is the method of imaging a single plane, or slice, of an object resulting in a tomogram. There are several forms of tomography. Linear tomography is the most basic form of tomography. The X-ray tube moved from point "A" to point "B" above the patient, while the cassette holder (or "bucky") moves simultaneously under the patient from point "B" to point "A." The fulcrum, or pivot point, is set to the area of interest. In this manner, the points above and below the focal plane are blurred out, just as the background is blurred when panning a camera during exposure. No longer carried out and replaced by computed tomography.

Polytomography was a complex form of tomography. With this technique, a number of geometrical movements were programmed, such as hypocycloidic, circular, and elliptical. Philips Medical Systems produced one such device called the "Polytome." This unit was still in use into the 1990s, as its resulting images for small or difficult physiology, such as the inner ear, was still difficult to image with CTs at that time. As the resolution of CTs got better, this procedure was taken over by the CT.

Zonography is a variant of linear tomography, where a limited arc of movement is used. It is still used in some centers for visualizing the kidney during an intravenous urogram (IVU).

Orthopantomography (OPT or OPG) is the only common tomographic examination in use. This makes use of a complex movement to allow the radiographic examination of the mandible, as if it were a flat bone.

Computed Tomography (CT), or Computed Axial Tomography (CAT: A CT scan, also known as a CAT scan), is a helical tomography (latest generation), which traditionally produces a 2D image of the structures in a thin section of the body. It uses X-rays. It has a greater ionizing radiation dose burden than projection radiography; repeated scans must be limited to avoid health effects. CT is based on the same principles as X-Ray projections but in this case, the patient is enclosed in a surrounding ring of detectors assigned with 500-1000 scintillation detectors (fourth-generation X-Ray CT scanner geometry). Previously in older generation scanners, the X-Ray beam was paired by a translating source and detector.

Ultrasound: Medical ultrasonography uses high frequency broadband sound waves in the megahertz range that are reflected by tissue to varying degrees to produce (up to 3D) images. This is commonly associated with imaging the fetus in pregnant women. Uses of ultrasound are much broader, however. Other important uses include imaging the abdominal organs, heart, breast, muscles, tendons, arteries and veins. While it may provide less anatomical detail than techniques such as CT or MRI, it has several advantages which make it ideal in numerous situations, in particular that it studies the function of moving structures in real-time, emits no ionizing radiation, and contains speckle that can be used in elastography.

Ultrasound is also used as a popular research tool for capturing raw data, which can be made available through an ultrasound research interface, for the purpose of tissue characterization and implementation of new image processing techniques. The concepts of ultrasound differ from other medical imaging modalities in the fact that it is operated by the transmission and receipt of sound waves. The high frequency sound waves are sent into the tissue and depending on the composition of the different tissues; the signal will be attenuated and returned at separate intervals. A path of reflected sound waves in a multilayered structure can be defined by input acoustic impedance (ultrasound sound wave) and the reflection and transmission coefficients of the relative structures.

Contrast-enhanced ultrasound (CEUS) is the application of ultrasound contrast medium to traditional medical sonography. Ultrasound contrast agents rely on the different ways in which sound waves are reflected from interfaces between substances. This may be the surface of a small air bubble or a more complex structure. Commercially-available contrast media are gas-filled microbubbles or microspheres that are administered intravenously to the systemic circulation. Microbubbles have a high degree of echogenicity, which is the ability of an object to reflect the ultrasound waves. The echogenicity difference between the gas in the microbubbles and the soft tissue surroundings of the body is immense. Thus, ultrasonic imaging using microbubble contrast agents enhances the ultrasound backscatter, or reflection of the ultrasound waves, to produce a unique sonogram with increased contrast due to the high echogenicity difference. Contrast-enhanced ultrasound can be used to image blood perfusion in organs, measure blood flow rate in the heart and other organs, and has other applications as well.

There are a variety of microbubble contrast agents. Microbubbles differ in their shell makeup, gas core makeup, and whether or not they are targeted. Selection of microbubble shell material determines how easily the microbubble is taken up by the immune system. A more hydrophilic material tends to be taken up more easily, which reduces the microbubble residence time in the circulation. This reduces the time available for contrast imaging. The shell material also affects microbubble mechanical elasticity. The more elastic the material, the more acoustic energy it can withstand before bursting. Currently, microbubble shells are composed of albumin, galactose, lipid, or polymers.

Microbubble gas core is the most important part of the ultrasound contrast microbubble because it determines the echogenicity. When gas bubbles are caught in an ultrasonic frequency field, they compress, oscillate, and reflect a characteristic echo—this generates the strong and unique sonogram in contrast-enhanced ultrasound. Gas cores can be composed of air, or heavy gases like perfluorocarbon, or nitrogen. Heavy gases are less water-soluble so they are less likely to leak out from the microbubble to impair echogenicity. Therefore, microbubbles with heavy gas cores are likely to last longer in circulation.

Regardless of the shell or gas core composition, microbubble size is fairly uniform. They lie within a range of one (1) to four (4) micrometers in diameter. That makes them smaller than red blood cells, which allows them to flow easily through the circulation as well as the microcirculation.

Regarding specific microbubble agents, Optison, an FDA-approved microbubble made by GE Healthcare, has an albumin shell and octafluoropropane gas core. The second FDA-approved microbubble, Levovist, made by Schering, has a lipid/galactose shell and an air core.

Perflexane lipid microspheres (trade name Imagent or previously Imavist) is an injectable suspension developed by Alliance Pharmaceutical approved by the FDA (in June 2002) for improving visualization of the left ventricular chamber of the heart, the delineation of the endocardial borders in patients with suboptimal echocardiograms. Besides its use to assess cardiac function and perfusion, it is also used as an enhancer of the images of prostate, liver, kidney and other organs.

Perflutren lipid microspheres (trade name Definity) are composed of octafluoropropane encapsulated in an outer lipid shell.

Targeted microbubbles are under preclinical development. They retain the same general features as untargeted microbubbles, but they are outfitted with ligands that bind specific receptors expressed by cell types of interest, such as inflamed cells or cancer cells. Current microbubbles in development are composed of a lipid monolayer shell with a perflurocarbon gas core.

The lipid shell is also covered with a polyethylene glycol (PEG) layer. PEG prevents microbubble aggregation and makes the microbubble more non-reactive. It temporarily "hides" the microbubble from the immune system uptake, increasing the amount of circulation time, and hence, imaging time. In addition to the PEG layer, the shell is modified with molecules that allow for the attachment of ligands that bind certain receptors. These ligands are attached to the microbubbles using carbodiimide, maleimide, or biotin-streptavidin coupling. Biotin-streptavidin is the most popular coupling strategy because biotin's affinity for streptavidin is very strong and it is easy to label the ligands with biotin.

Currently, these ligands are monoclonal antibodies produced from animal cell cultures that bind specifically to receptors and molecules expressed by the target cell type. Since the antibodies are not humanized, they will elicit an immune response when used in human therapy. Humanizing antibodies is an expensive and time-intensive process, so it would be ideal to find an alternative source of ligands, such as synthetically manufactured targeting peptides that perform the same function, but without the immune issues.

Optical imaging is a technology that measures light produced by biological or chemical moieties. It is a "window of opportunity" for the non-invasive spatiotemporal visualization of biological phenomena inside a live animal. Optical imaging technologies rely on light producing optical reporters such as luciferase and fluorescent proteins, fluorescent dyes and conjugates. Genes encoding luciferase and fluorescent proteins can be engineered into cells (e.g., cancer cell lines and infectious disease agents) and animals (transgenic mice and rats) to enable them to produce light that can then be visualized through the tissues of a live animal using specialized imaging equipment and software. These highly sensitive dual bioluminescence and fluorescence imaging systems allow significantly fewer animals to be used due to the generation of superior data and better biostatistics.

XenoLight Bio/Chemi-luminescent Substrates: Luciferin (D-Luciferin, Potassium salt) is a chemical substance found in the cells of various bioluminescent organisms. When luciferin is oxidized under the catalytic effects of luciferase and ATP, a bluish-green light is produced. Because the reaction is dependent on ATP, it allows researchers to determine the presence of energy or life. Firefly luciferin is a particularly good reporter for in vivo biophotonic imaging due to properties of its emission spectra. RediJect Coelenterazine h is a bioluminescence substrate in a ready-to-use, injectable format. With Caliper's RediJect Coelenterazine, reproducible results can be ensured by minimizing variability in formulation, minimizing freeze/thaw and controlling batch-to-batch variation. RediJect Coelenterazine has been pre-formulated to fit common workflow patterns and optimize results for all experiments with *Renilla* luciferase. The ready-to-use substrate formulation allows one to focus on animal handling and biology.

XenoLight NIR Fluorescent Reagents: XenoLight CF™ labeling kits provide a flexible solution for labeling proteins, peptides or antibodies. Available in a 680 run, 750 run or 770 run dye formulation, XenoLight CF kits are effective for in vivo optical imaging. The low immunogenicity coupled with high solubility and >95% reactivity results in conjugates that are highly specific, bright and with improved half-life. These reagents, in solution form or as a free drug, are widely used by many scientists (See Jenkins, D., Y. Oei, et al. (2003) "Bioluminescent imaging (BLI) to improve and refine traditional murine models of tumor growth and metastasis." Clinical and Experimental Metastasis 20 (8): 733-744; Jenkins, D., Y. Hornig, et al. (2004). "Luciferase-expressing MCF-7-luc-F5 human breast cancer cells used to monitor mammary fat pad tumor growth and metastasis in vivo in nude-beige mice." Proceedings of the American Association for Cancer Research 2004 (1): 1179.; F Lassailly, E Griessinger, D Bonnet" Microenvironmental contaminations" induced by fluorescent lipophilic dyes used for non-invasive in vitro and in vivo cell tracking, 2010; Yoji Hakamata, Takashi Murakami, Eiji Kobayashi "Firefly Rats" as an Organ/Cellular Source for Long-Term In Vivo Bioluminescent Imaging, 2006; T. J. Snoeks, C. W. Lowik, E. L. Kaijzel 'In vivo' optical approaches to angiogenesis imaging. 2010; C. L. Hsieh, Z. Xie, Z. Y. Liu, J. E. Green, W. D. Martin, M. W. Datta, F. Yeung, D. Pan, L. W. K. Chung luciferase transgenic mouse model: visualization of prostate development and its androgen responsiveness in live animals, 2005; Jenkins, D., Y. Hornig, et al. (2005). "Bioluminescent human breast cancer cell lines that permit rapid and sensitive in vivo detection of mammary tumors and multiple metastases in immune deficient mice." Breast Cancer Res 7 (4): 444-454; and Shan, L., S. Wang, et al. (2007). "Dual probe with fluorescent and magnetic properties for imaging solid tumor xenografts." Molecular Imaging 6 (2): 85-95).

With recent advancement in imaging technology, preclinical imaging and molecular imaging is becoming integral part of research and development in medical science (5-6). Non-invasive and in vivo imaging techniques have been essential to study changes at the organ, tissue, cell, or molecular level in animal models responding to physiological or environmental changes. Particularly, tumor imaging provides several advantages, such as (1) better prediction of disease progression, (2) untangling of the complex biology of tumors (feasibility of longitudinal measurements, three-dimensional maps of tumor, etc.), (3) visualization of different biological aspects of metastasis, (4) strategies to alter tumor micro environment and interpret them into improved cancer detection, (5) tailored cancer therapeutics to match individual needs, (6) streamlining of cancer drug development, and (7) identification of targets on tumors and translation into new therapy in humans.

Preclinical imaging techniques can be classified into morphological/anatomical techniques (high-frequency micro-ultrasound, magnetic resonance imaging (MRI) and computed tomography (CT)) and molecular imaging techniques (optical imaging (fluorescence and bioluminescence), positron emission tomography (PET), and single photon emission computed tomography (SPECT)) (7). These techniques have their own advantages and limitations. To overcome these limitations and gain further advantage, multi-modal systems are developed by combining the advantages of anatomical modalities, such as CT and MRI, with the functional imaging of PET and SPECT (8-10).

Bioluminescence imaging is a noninvasive and cost-effective method of imaging that allows real-time observation of complex biological activity in live animals (11-13). Bioluminescence imaging is based on a gene construct to produce a protein "luciferase", an enzyme that converts D-luciferin to oxyluciferin by luciferase-catalyzed conversion to provide imaging contrast as a light emission (14-16). As mentioned above, bioluminescence imaging in animal models requires a gene construct that produces the luciferase enzyme; typically firefly luciferase expressing construct is used. Other luciferases used, except the firefly variety, are *Renilla* luciferase (17) and nematode luciferase (18-19). Due to their unique substrate specificity and characteristic (20), they can be used simultaneously.

Substrate "luciferin" is given as an intravenous (IV) or intraperitoneal (IP) injection to animal for imaging purpose. Other methods of delivery are reported as an osmotic pump (21) and mixing with drinking water (22). Due to faster clearance of luciferin from plasma, it renders a very short imaging window with relatively stable light emission (23). However, multiple injections are needed and do alter many variables, such as luciferin concentration, substrate elimination, etc. In an effort to overcome these problems, researchers have reported continuous delivery of luciferin to enhance temporal resolution by use of osmotic pump (21, 24) and increase in radiance by liposomal delivery (25).

The use of nanoparticle delivery systems is known to be biocompatible and protect the active ingredient from degradation. Among the various nanoparticle systems, lipid nanoparticles are thought to be promising as drug carrier systems for tissue application. Melt-emulsified nanoparticles, based on lipids that are solid at room temperature, have several advantages over nanoemulsions, nanosuspensions, mixed micelles, polymeric nanoparticles and liposomes. The advantages of these solid lipid nanoparticles (SLN) is that they protect the active ingredients from enzymatic degradation, prevent trans-epidermal water loss, and release the drugs in a controlled manner for prolonged periods and thereby enhance the therapeutic effect (Jenning, V., et al., Vitamin A-Loaded Solid Lipid Nanoparticles for Topical use: Drug Release Properties, J. Control. Release. 2000, 66, 115-126). The stabilization of chemically unstable drugs by incorporation into a lipid matrix and also sustained release is possible due to the solid matrix properties of solid lipid nanoparticles (SLN) (Souto, E. B., et al., Development of a Controlled Release Formulation Based on SLNI and NLC for Topical Clotrimazole Delivery, Int. J. Pharm. 2004, 278, 71-77, Muller, R. H., et al., Cytotoxicity of Solid Lipid Nanoparticles as a Function of the Lipid Matrix and the Surfactant, Pharm. Res. 1997, 14, 458-462; Wissing. S. A., et al., Investigations on the Occlusive Properties of Solid Lipid Nanoparticles (SLN), J. Cosmet. Sci. 2001, 52. 313-323).

In order to decrease the degree of organization of the lipid matrix in SLN and the drug loading, carrier nano lipid crystal nanoparticles (NLCN) were developed and are known as the second generation of lipid nanoparticles (Pardeike, J., et al., Lipid Nanoparticles (SLN. NLC) in Cosmetic and Pharmaceutical Dermal Products, Int. J. Pharm. 366 (1-2) (2009) 170-184). Based on the chemical nature of the lipid molecules, the inner structure of NLCN differs from that of SLN, in that NLCNs are composed of mixtures of solid and liquid (oils) lipids, whereas SLNs are composed only of solid lipids. Because the solubility of active ingredients in oils is generally much higher than in solid lipids, higher drug loading capacity and minimal expulsion during storage can be achieved by NLCN.

Kheirolomoom et al. developed a method of enhancing in vivo bioluminescence imaging using a liposomal luciferin delivery system (Kheirolomoom et al., "Enhanced in vivo bioluminescence imaging using liposomal luciferin delivery system", J Control Release, 141 (2), NIH Public Access: Author Manuscipt, January 2010). However, they used phospholipids to create liposomes and would be unable to fabricate nanoparticle carrier systems, as phospholipids are incompatible with the creation of nanoparticle systems. In contrast, nanoparticle systems provide their own range of benefits, including increased stability, entrapment, carrier capacity, in vivo transportation, ability to incorporate hydrophilic and hydrophobic substances, variable routes of administration, controlled drug release (thus increased bioavailability), etc.

Despite the foregoing advancements, the outcome or utility of these techniques is limited for one or more reasons, as has been made apparent. Accordingly, what is needed is a delivery system of active biomedical/pharmaceutical agent(s) used for in vivo (whole body, organ, or tissue-specific) medical and preclinical imaging for intravenous, intraperitoneal, or inhalation route in such a fashion that it allows incorporation of the multiple systems in such manner that hurdles of individual techniques may be overcome. However, in view of the art considered as a whole at the time the present invention was made, it was not obvious to those of ordinary skill in the field of this invention how the shortcomings of the prior art could be overcome. To date, no study has been reported on the use of modified nanoparticle for in vivo (whole body, organ or tissue-specific) imaging comprising one or more active biomedical/pharmaceutical agents.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved nanodelivery system for enhancing in vivo medical and preclinical imaging of tumors to diagnose and detect tumors is now met by a new, useful, and nonobvious invention.

In an embodiment, the current invention includes a modified nanoparticle, microbubble or microsphere delivery system for noninvasively delivering an active substance or agent to a target within a subject's body for medical and preclinical imaging. The delivery system comprises a nanoparticle carrier formed from solid phase and liquid phase "ingredients", for example lipids, metals, polymers, and carbon nanotubes. The solid-to-liquid ingredient ratio is important in that it should be optimized based on entrapment efficiency, loading efficiency, and the release rate of the active agent desired over a period of time. A drug delivery enhancer, target specifier, or target-honing molecule is engrafted onto the surface of the carrier to direct carrier to the target within the subject. A bio-imaging agent (causing bioluminescence at the target within the subject) is encapsulated within the modified, optimized carrier, which unexpectedly enhances or increases the half-life of the bio-imaging agent.

If the ingredients used to fabricate the carrier are lipids, then they can be a mixture of monoglycerides, diglycerides, and triglycerides. The ingredient would further include a nickel chelating compound as well. In a further embodiment, the lipids would include a lipid solid state and an oil liquid state. The lipid solid state can be Monosteol™ and Precirol™, as they showed many benefits, though an array of other examples is contemplated and will become apparent herein. The oil liquid state can be Miglyol™, as it showed many benefits, though an array of other examples is contemplated and will become apparent herein.

The target-honing molecule can be a tumor-honing molecule that targets tumor cells and directs the carrier system to a tumor within the subject, thereby permitting medical and preclinical imaging of a tumor in said subject and multimodality of said tumor.

The bio-imaging agent may be luciferin, D-luciferin, coelenterazine h, XenoLight fluorescent dye, or Galacton-Star, though other bioluminescent agents are contemplated as well. If the bio-imaging agent is luciferin, then the half-life of luciferin can be increased to greater than two (2) hours by utilizing the current invention. Additionally, luciferin can have an effective biofluorescence (detectable by known imaging techniques) greater than 24 hours after administering the carrier to the subject.

The nanoparticle delivery system, as a whole, can be less than 200 nm and still carry sufficient active agent. This size allows for easier movement through the circulatory system of the subject.

By using the current system, the release rate of the bio-imaging agent can be less than about 50% at least 24 hours after administration of the carrier to the subject. This provides a controlled, sustained release of the bio-imaging agent, thus also allowing for a longer time to image the target in vivo.

In a separate embodiment, the current invention includes a method of delivering an active substance or agent to a target within a subject for medical and preclinical imaging. The method comprises fabricating a nanoparticle carrier system from a plurality of solid phase and liquid phase ingredients, for example lipids, metals, polymers, and carbon nanotubes. The solid-to-liquid ingredient ratio is important in that it should be optimized based on entrapment efficiency, loading efficiency, and the release rate of the active agent desired over a period of time. The carrier system is modified by engrafting a target-honing molecule onto the surface of the carrier system. This directs the system to the target in the subject. Further, a bio-imaging agent is encapsulated or entrapped within the carrier system and, when released from the system, causes bioluminescence at the site of the target in the subject. The modified nanoparticle carrier system containing the bio-imaging agent is then administered to the subject (e.g., subcutaneously, intraperitoneally, intravenously), which, in turn, enhances or increases the half-life of the bio-imaging agent in circulation in the subject.

Among other methodologies, the carrier system can be modified by maleimide chemical conjugation of the target-honing molecule to the surface of the system.

The bio-imaging agent may be luciferin, D-luciferin, coelenterazine h, XenoLight fluorescent dye, or Galacton-Star, though other bioluminescent agents are contemplated as well. If the bio-imaging agent is luciferin, then the half-life of luciferin can be increased to greater than two (2) hours by utilizing the current invention. Additionally, luciferin can have an effective biofluorescence (detectable by known imaging techniques) greater than 24 hours after administering the carrier to the subject.

By using the current methodology, the release rate of the bio-imaging agent can be less than about 50% at least 24 hours after administration of the carrier to the subject. This provides a controlled, sustained release of the bio-imaging agent, thus also allowing for a longer time to image the target in vivo.

The target-honing molecule can be a tumor-honing molecule that targets tumor cells and directs the carrier system to a tumor within the subject, thereby permitting medical and preclinical imaging of a tumor in said subject and multimodality of said tumor.

As a whole, the nanoparticle carrier system can be less than 200 nm and still carry sufficient active agent. This size allows for easier movement through the circulatory system of the subject.

In a separate embodiment, the current invention includes a method of evaluating or monitoring tumor progression or tumor vasculature via in vivo imaging of a tumor within a subject by administering luciferin to the subject. The method comprises fabricating a nanoparticle carrier system of less than 200 nm in size from a plurality of lipids. The lipids include solid phase lipids and liquid phase oils in a stable, optimized ratio based on entrapment efficiency, loading efficiency, and release rate of luciferin desired over a period of time. The solid phase is Monosteol™ and/or Precirol™ (others are contemplated and will become apparent), and the liquid phase is Miglyol™ (others are contemplated and will become apparent). The carrier system is modified by engrafting a tumor-honing molecule on the surface of the carrier system to direct the system to the tumor in the subject. This permits medical and preclinical imaging of the tumor in the subject and multimodality of the tumor. Luciferin is then encapsulated within the carrier system. Luciferin causes bioluminescence at the site of the tumor. The modified nanoparticle carrier system containing luciferin is then administered to the subject subcutaneously, intraperitoneally, or intravenously. By performing this method, the half-life of luciferin can increase to more than two (2) hours in the carrier system after being administered to the subject. Additionally, the release rate of luciferin can be lower than 50% at least 24 hours after administration of the carrier system to the subject, thereby providing a controlled sustained release of luciferin, which continues to be detectable by known imaging techniques at this 24-hour mark and later.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
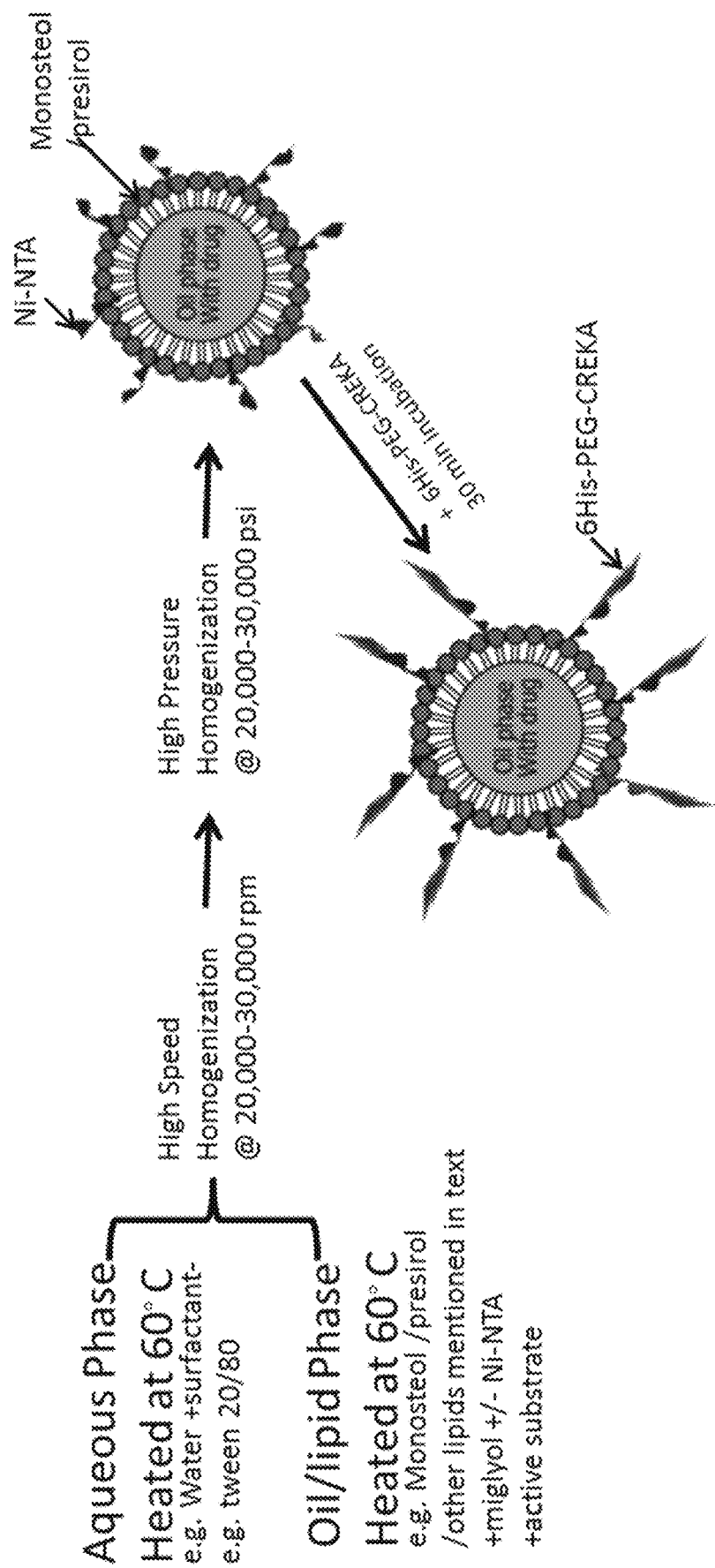
FIG. 1 is a schematic illustrating preparation of modified nanoparticles according to an embodiment of the current invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The present invention relates to a method of delivery of modified nanostructures of active biomedical and pharmaceutical agent(s) for longer sustained bioluminescent, fluorescent, or contrast signals and increased signal flux at specific sites of interest on the body. The invention is described herein in detail using the terms defined below unless otherwise specified.

The terms "nanostructured carrier nanoparticles" (NCN or NCNs) and "nanostructured carrier" (NC or NCs) are used interchangeably and are meant to describe the plurality of lipid, metal, polymers, or carbon nanotube carrier nanoparticles forming the nanostructure. The lipid, metal, polymer, or carbon nanotube carrier nanoparticles in the nanostructure are produced using blends of solid and liquid (lipids/oils) ingredients. To obtain blends for the particles in the nanostructure, solids are mixed with liquids in a desired ratio. The blends obtained are solid at body temperature. These NCNs can encapsulate active substances; NCNs can be produced by known hot or cold high pressure homogenization techniques.

Exemplary oil-based or lipidic medium carriers for the NCN are mono-, di- and triglycerides or mixtures thereof, and nickel chelating compounds. In a preferred embodiment, the oil-based or lipidic medium carrier may be COMPRITOL 888 ATO brand, MIGLYOL 812 brand, and DOGS-NTA-Ni chelating lipid and the like.

A nanoparticle or particulate of this invention has an active substance encapsulated within the nanoparticles forming the nanostructure or carrier system. Methods of preparing nanoparticles that include an active substance encapsulated within are known to those skilled in the art.

As an example used herein, "encapsulated within" means the active substance is contained substantially inside the NCN or nanoparticle.

Modifying a surface of the nanostructured carrier nanoparticles refers to the method of coating the outside of the surface of the nanoparticles with a drug delivery enhancer. More specifically, the surface is modified by engraftment intern coating of the drug delivery enhancer onto the nanoparticle, for example coating a CREKA peptide onto the nanoparticle surface. The engraftment can be accomplished by using, for example, DOGS-NTA-Ni chelating/spacer (e.g., lipid), wherein the DOGS (portion of the spacer, e.g., lipid portion) is embedded in the preformed nanoparticle, and the NTA-Ni portion/tail of the spacer is projected outside of the nanoparticle surface such that the 6-histidine on the peptide bonds strongly to NTA-Ni portion/tail to form a nanoparticle with an NTA-Ni-6Histidine-CREKA surface. It is well-known in the field that histidine tag binds to NTA-Ni. The surface modification of the nanoparticles can also be accomplished by utilizing methods such as maleimide chemical conjugation and chemical conjugation of peptide to the nanoparticle's surfaces using PEG spacers, or other suitable methods. The preformed nanoparticles are coated as described and incubated for a period of time such that a bond is formed between the 6 histidine and NTA-Ni.

As used herein, the term "liposome" means a type of lipid-based particulate and specifically includes a compartment that is completely enclosed by a lipid bilayer typically composed of phospholipids. Liposomes are prepared according to standard techniques known to those skilled in the art. Emulsion, polymeric, silica, carbon nanotubes, rare metals, silver and/or gold nanoparticle carrier systems may also encapsulate an active agent and be modified on the surface with a drug delivery enhancer for topical applications. Examples of suitable polymeric nanoparticles are PLGA, poly(D,L-lactide-co-glycolide), poly(D,L-lactide), poly(D,L-lactide-co-lactide), poly(L-lactide), poly(glycolide), poly(L-lactide-co-glycolide), poly(caprolactone), poly(glycolide-co-trimethylene carbonate), poly(3-hydroxybutyrate), poly(3-hydroxybutyrate-co-3-hydroxyvalerate), poly(4-hydroxybutyrate), poly(ester amide), poly(ester-sulfoester amide), poly(orthoester), poly(anhydride), and polysaccharides, such as alginate and chitosan.

The active biomedical or pharmaceutical agent(s) can include small molecules, proteins or peptides, alone or in combination with other small molecules, proteins and/or peptides. The examples below serve to further illustrate the invention, to provide those of ordinary skill in the art with a complete disclosure and description of how the nanostructures or methods herein are made and evaluated, and are not intended to limit the scope of the invention.

In the following examples, luciferin was encapsulated within a lipid nanocarrier system ("Nano-Luc") for continuous prolonged sustained delivery once administered through variable routs such as IV, IP, and subcutaneous (SQ) delivery. Lipid nanoparticles have been shown to protect the active ingredients from enzymatic degradation, provide controlled release of the active drug, and enhance the therapeutic effect and stabilization of chemically unstable drugs due to lipid matrix (26-28). Along with the Nano-Luc, nanoparticles were developed containing XenoLight DiR (near infrared region fluorescence dye) and luciferin for multimodality imaging of tumors. These were known as NanoLuc-DiR.

Example 1

Lung cancer is one of the leading causes of deaths (1.3 million deaths annually) worldwide. Non-small cell lung cancer (NSCLC) accounts for 85% of all lung cancers. Vascular endothelial growth factor (VEGF) over-expression (61% to 92% of NSCLC) is associated with poor survival. Recently, new approaches in the treatment of lung cancer with novel drugs, which selectively inhibit tumor blood supply, thus controlling cancer cell survival, proliferation and/or metastasis, in combination with conventional anticancer or antiangiogenic drugs, have generated clinical interest. DIM-C-pPhC6H5 (DIM-P), a c-substituted diindolylmethanes is a recent anti-cancer agent. Objectives of this study were: (1) to formulate tumor homing pegylated CREKA peptide coated nanoparticles of DIM-P (PCNCs-D)/D-luciferin (PCNCs-DI)/XenoLight-DiR (PCNCs-Di); and (2) to evaluate in vivo imaging of tumor progression/tumor vasculature and tracking of nanoparticle delivery system.

Nanoparticles were prepared with DIM-P (NCs-D)/D-luciferin (NCs-DI)/XenoLight-DiR (NCs-Di), Compritol, Miglyol, DOGS-NTA-Ni and sodium taurocholate using a high pressure homogenizer (Nano-DeBEE). PCNCs-D and PCNCs-DI/PCNCs-Di were prepared by conjugating NCs-D and NCs-DI/NCs-Di with 6His-PEG2K-CREKA peptide and characterized for physical properties, clot binding assay and tube formation assay.

Figure 2A:
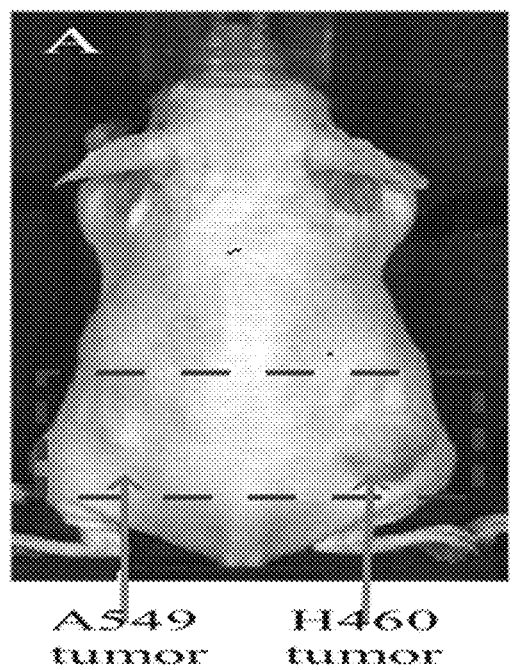
FIG. 2A is an in vivo image of an A549 and H460 lung cancer cell tumor bearing mouse in in vivo imaging system and spectrally unmixed image of vasculature.
Figure 2B:
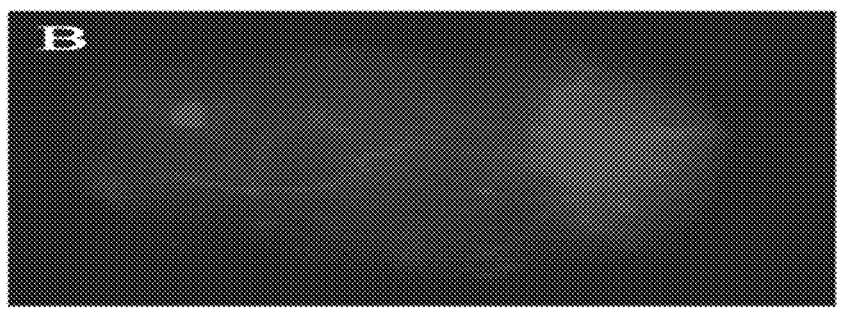
FIG. 2B is an in vivo image of FIG. 2A with PCNCs-Di.
Figure 2C:
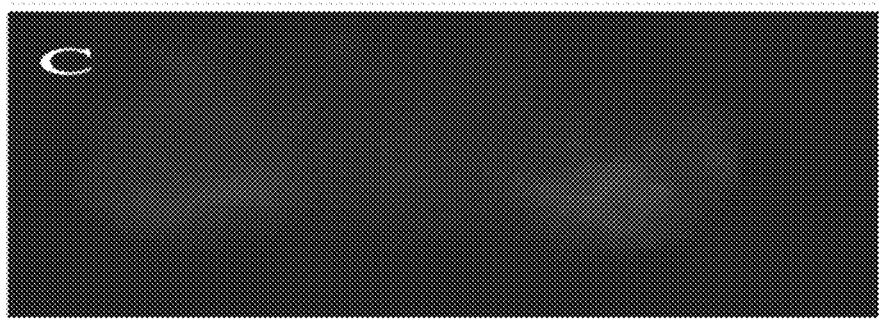
FIG. 2C is an in vivo image of FIG. 2A with NCs-Di.
Figure 3:
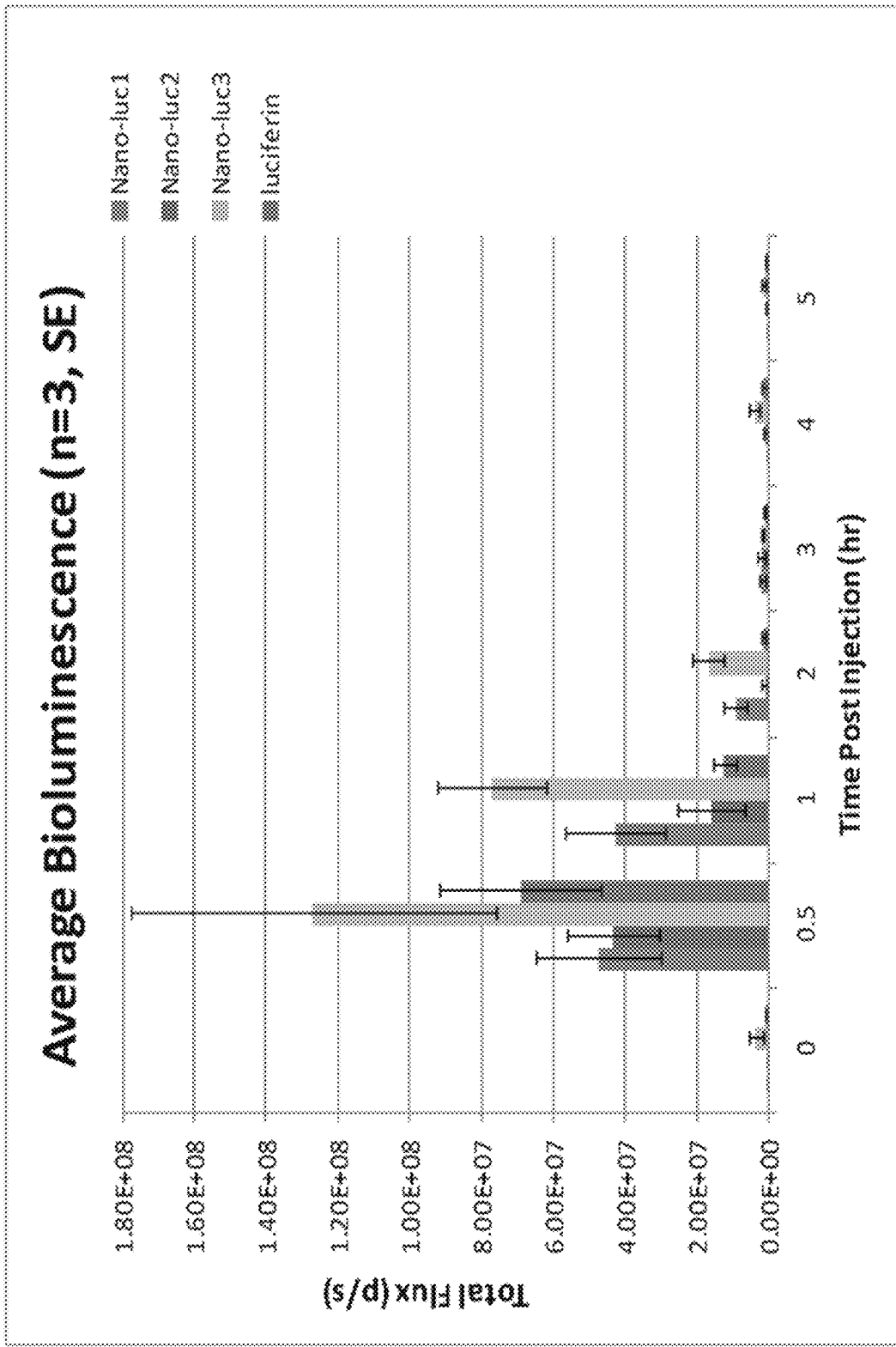
FIG. 3 is a graphical illustration showing that all three modified nanoparticles (Nano-Luc1, 2, and 3) produced equivalent level of luciferase signals. The luciferase signals were brightest at 30-60 minutes after injection of the Nano-Lucs. Nano-Luc1 and Nano-Luc3 prolonged the luciferase signal as compared with free luciferin.
Figure 4:
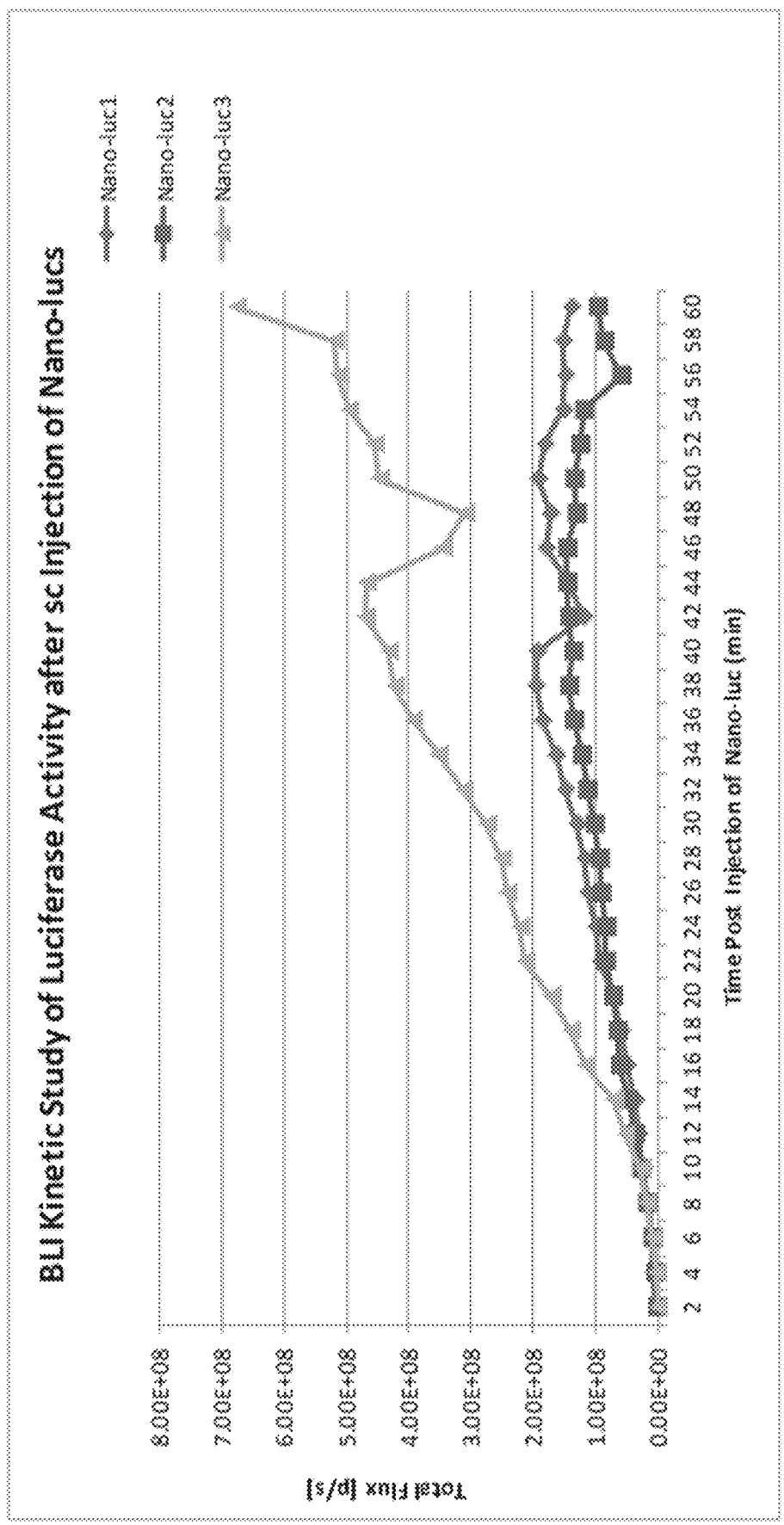
FIG. 4 is a graphical illustration showing that all three Nano-Lucs displayed different luciferase kinetics. Nano-Luc1 and Nano-Luc2 showed peak luciferase signal at 40-50 minutes. Nano-Luc3 showed continuous increase of luciferase signal over 60 minutes.
Figure 5A:
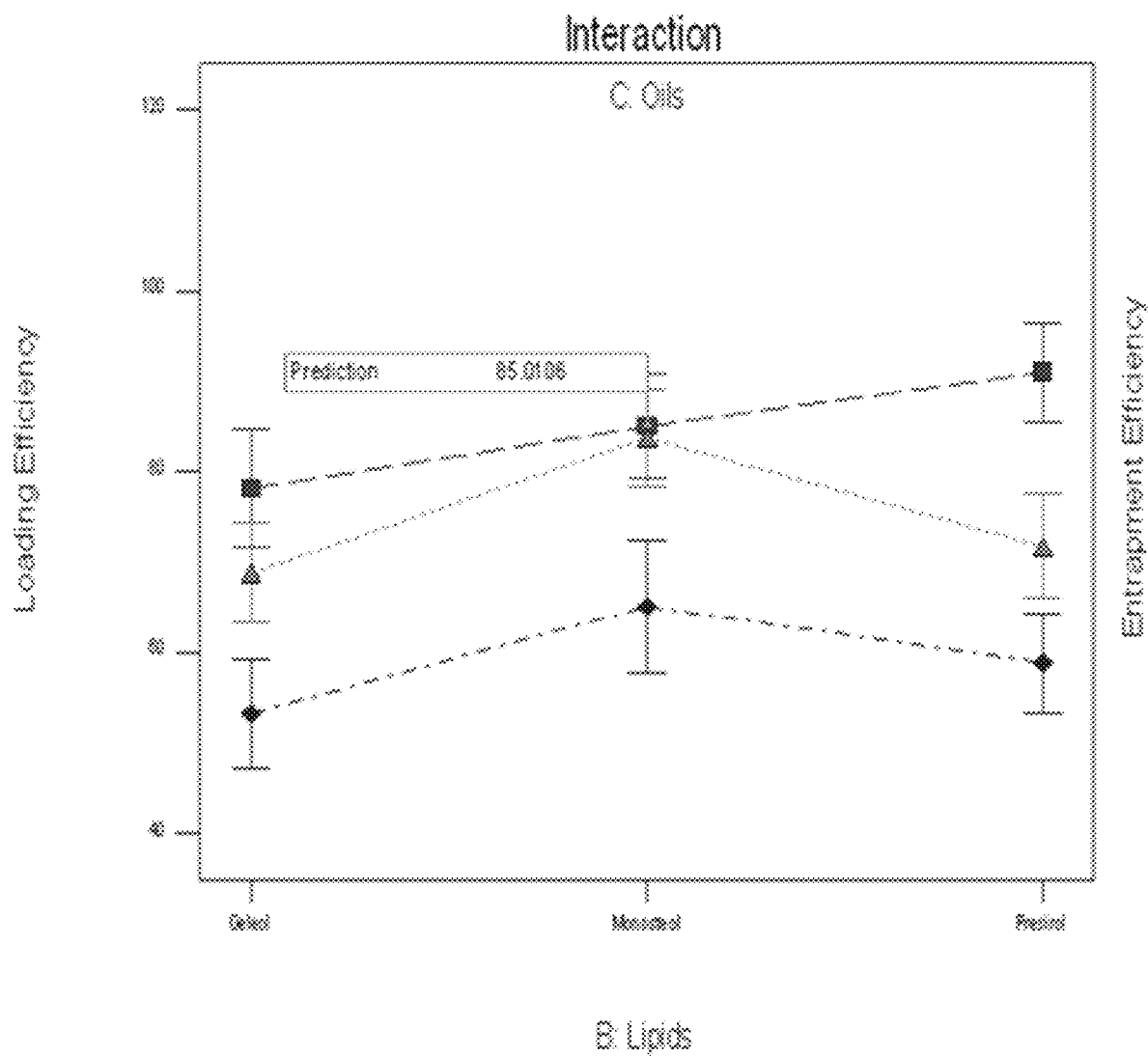
FIG. 5A depicts the effect of lipid- and oil-type on loading efficiency.
Figure 5B:
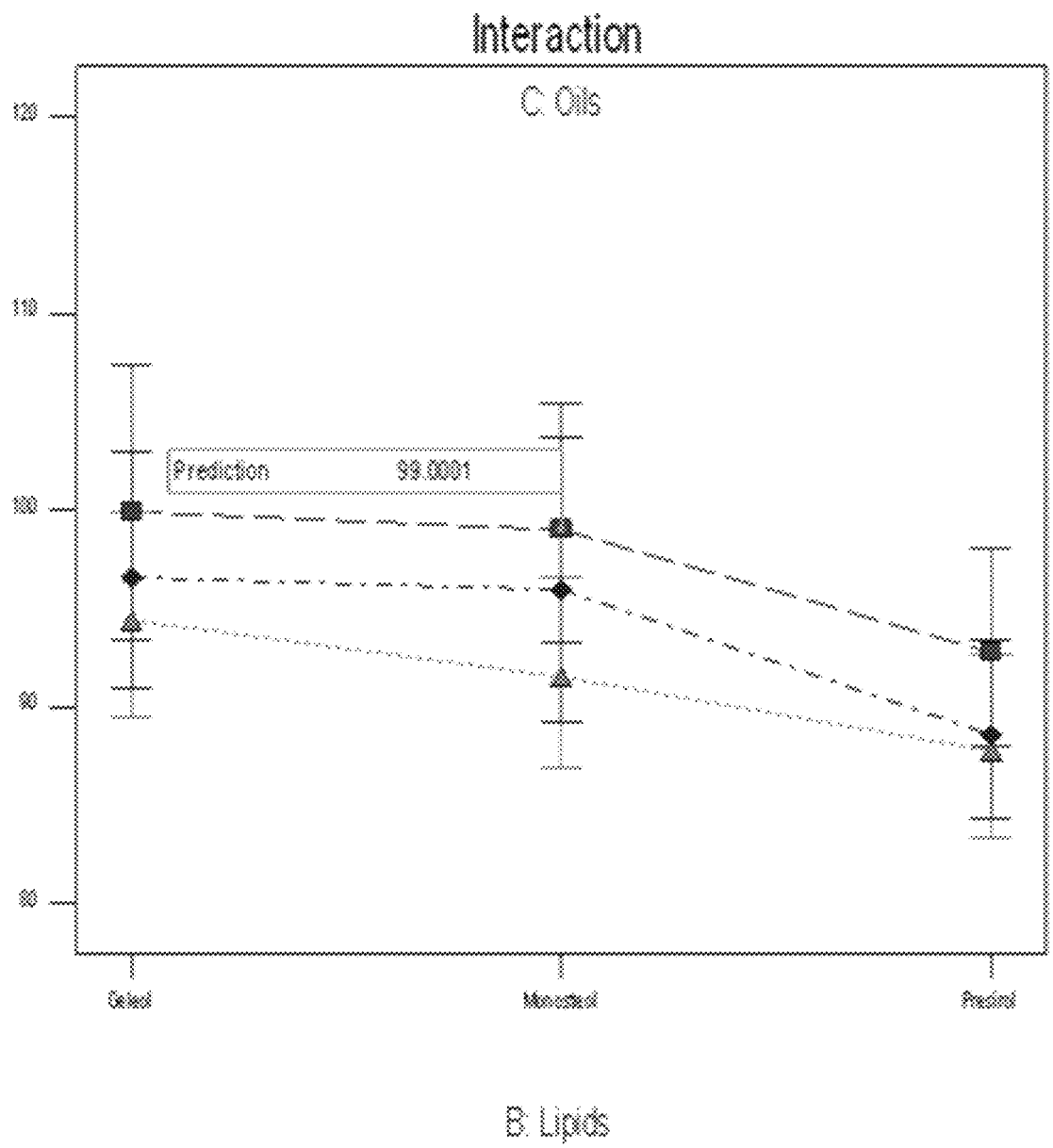
FIG. 5B depicts the effect of lipid- and oil-type on entrapment efficiency.
Figure 5C:
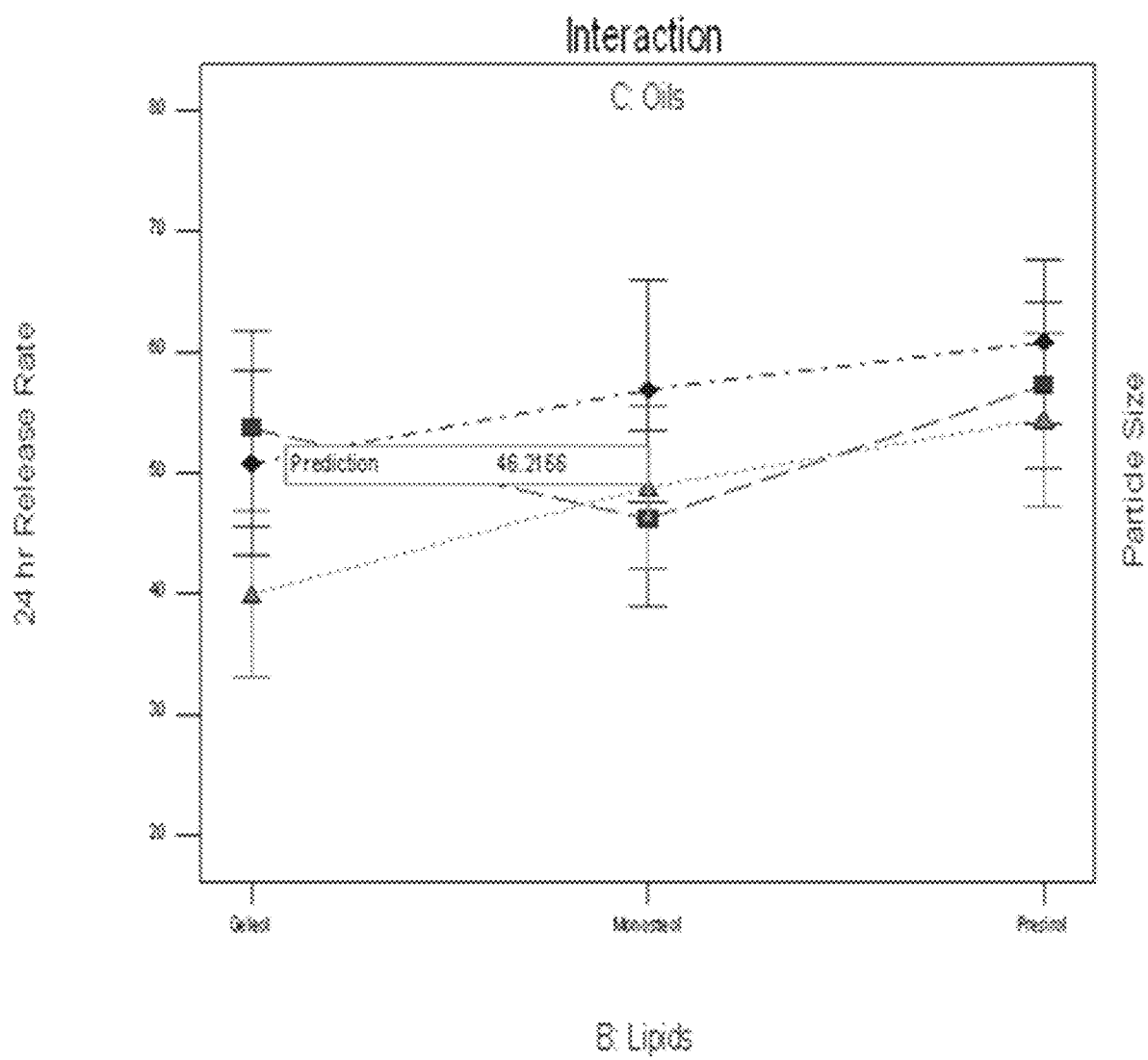
FIG. 5C depicts the effect of lipid- and oil-type on 24-hour release rate.
Figure 5D:
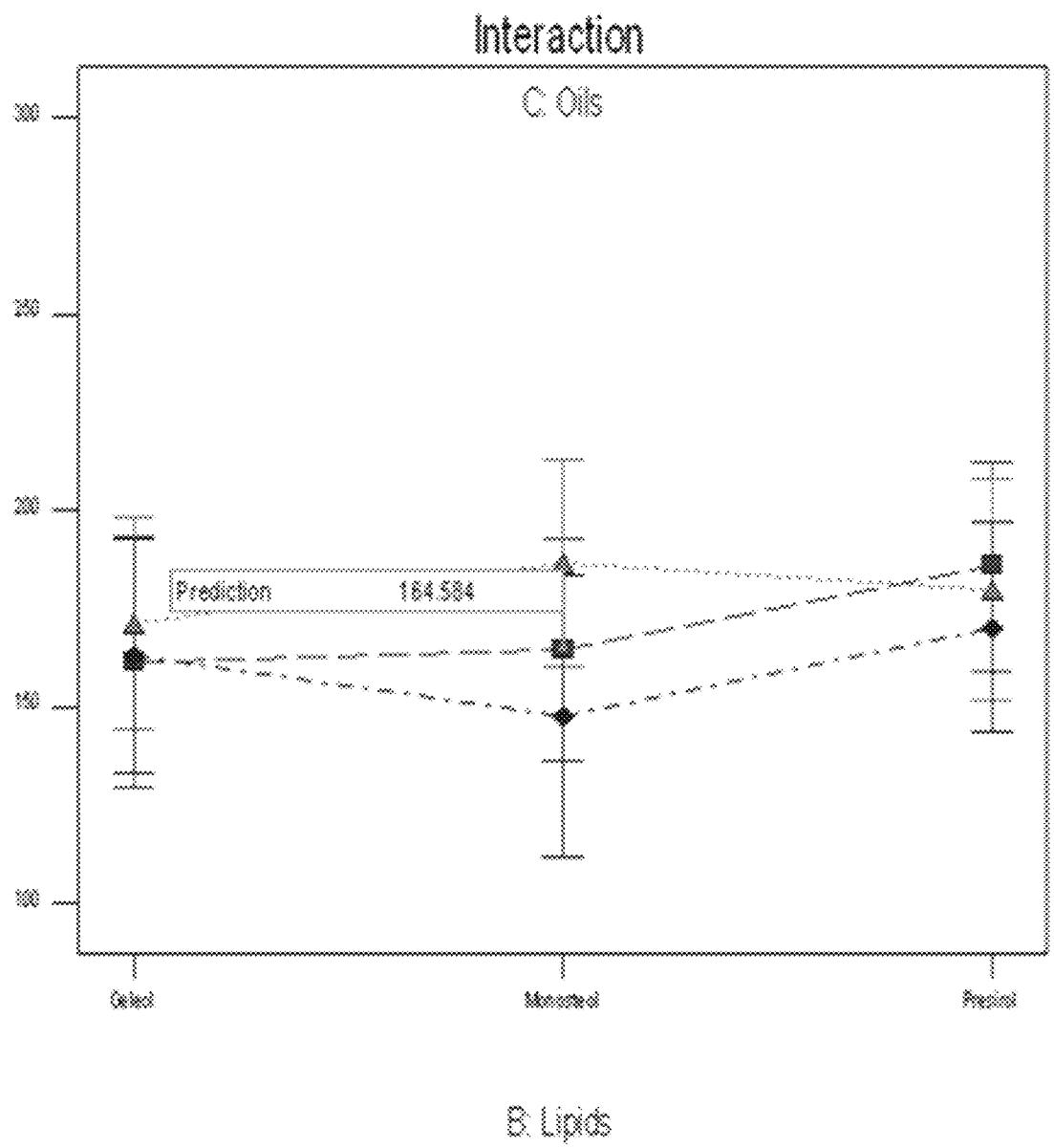
FIG. 5D depicts the effect of lipid- and oil-type in the RSM.

Pharmacokinetic parameters of formulations were evaluated in BALB/c mice. In vivo imaging of tumor and tracking of nanoparticles was carried out with IVIS® Spectrum CT (Caliper Life Sciences) by using fluorescent dye (XenoLight DiR) and bioluminescence (luciferin) following intravenous and inhalation delivery of nanocarriers. In vivo imaging following exposure of PCNCs-DL/PCNCs-Di demonstrated their targeting to the tumor vasculature (see FIG. 2), where the PCNCs-Di were found to migrate more in newly formed blood vessels, and total radiant efficiency $[p/s]/[\mu W/cm^2]$ was $2.1*10^{12} \pm 0.5*10^{12}$ over the period of 0.5 h to 3 h. NCs-Di did not show any specific migration to tumors confirming the specific targeting of PCNCs-Di, and total radiant efficiency $[p/s]/[\mu W/cm^2]$ was $0.6*10^{12} \pm 0.18*10^{12}$.

Example 2

The objective of this study was to formulate nanoparticles of D-luciferin (Nano-Luc), XenoLight-DiR (Nano-DiR) and dual probe nanoparticles with DiR and Luciferin (NanoLuc-DiR) for enhanced in vivo imaging of tumor progression, tumor vasculature and tumor multimodality as well as tracking of the nanoparticle delivery system. Nano-Luc and NanoLuc-DiR were prepared using different lipids for imaging studies. Nanoparticles were characterized for loading and entrapment efficiency, physical properties, release profile, toxicity and stability. Response Surface Methodology (RSM) was utilized to optimize the nanoparticles using design of experiment (DOE Vr.8.0).

Nano-Luc was evaluated against free luciferin for their pharmacokinetic parameters in mice. In vivo imaging of tumors and tracking of nanoparticles was carried out with an IVIS® SpectrumCT (Caliper life Sciences) using a murine xenograft, orthotopic and metastatic tumor models using different cell lines by subcutaneous, intraperitoneal, and intravenous administration of nanoparticles.

Particle size of Nano-Luc and NanoLuc-DiR were found to be <200 nm. Nano-Luc formulation showed a slow and controlled release up to 72 hr (90%). The optimized Nano-Luc had loading efficiency of 5.0 mg/ml with 99% encapsulation efficiency. Nano-Luc and NanoLuc-DiR formulations had good shelf stability, with less than 1% release over one month storage at room temperature and 10% release with accelerated stability testing at 40° C. Pharmacokinetic parameters showed that compared to quick in-and-out of free luciferin, Nano-Luc and NanoLuc-DiR enhanced plasma half-life of luciferin by longer circulation in plasma for more than 24 hr. Tumor multimodality was detected using spectrum CT/DLIT/FLIT imaging of subcutaneous tumor model in mice followed by NanoLuc-DiR administration. Nano-Luc and NanoLuc-DiR were seen to provide enhanced in vivo imaging for tumor diagnostic/detection and multimodality of tumors.

The efficiency and stability of Nano-Luc and NanoLuc-DiR were evaluated in nu/nu and Balb/c mouse models injected with tumor cells (lung and breast tumor cells) expressing the luciferase reporter gene (16, 29-30). The formulation for drug loading, entrapment efficiency and release of luciferin were characterized. Factors that affect these parameters, such as lipid formulation, ratio of lipids/oil/surfactant and process variables, were investigated and optimized by quality by design approach. The formulations were also characterized for stability by accelerated stability studies and differential scanning calorimetry.

Materials

Luciferin and Xenolight DiR were obtained from Calipers-Life Sciences & Technology-A Perkinelmer Company (Alameda, CA). The triglyceride Miglyol 812 was obtained from Sasol Germany GmbH (Witten, Germany), and other lipids were obtained from Gattefosse (Saint Priest, France). Dialysis tubing (Molecular weight cut off 6000-8000 Daltons and flat width of 23 mm) was obtained from Fisher Scientific (Pittsburgh, PA). Polyoxyethylene-20 oleyl ether or Volpo-20 (Oleth-20) was obtained from Croda Inc (New Jersey, USA). Vivaspin centrifuge filters (Molecular weight Cut off: 10, 000 Daltons) were procured from Sartorius Ltd, (Stonehouse, UK). Fetal bovine serum (FBS) and antibiotics were procured from Invitrogen Corp (Eugene, OR). The lung cancer cell lines (A549-luc, H460-luc) and breast cancer cell lines (4T1-luc, MDA-MB-231-luc) were obtained from Perkinelmer Company (Alameda, CA). The cells were maintained with supplemented media at 37° C. in the presence of 5% $CO_2$ in air. All other chemicals used in this study were of analytical grade.

Animals

Male Balb/c mice (20-25 g; Charles River Laboratories) were utilized for the studies. The protocol for in vivo experiments was approved by the Animal Care and Use Committee, Caliper Life Sciences—A Perkinelmer Company, Alameda CA. The animals were acclimated to laboratory conditions for one week prior to experiments and were on standard animal chow and water ad libitum. The temperature of room was maintained at 22±1° C. and the relative humidity of the experimentation room was found in the range of 35-50%.

Preparation of Nano-Luc and NanoLuc-DiR

Nano-Luc and NanoLuc-DiR were prepared by hot melt homogenization (31). Luciferin and/or Xenolight DiR were dissolved in organic solvent and mixed with lipid phase comprised of different lipids. Organic phase was removed by rota-evaporator for 30 min at 60° C. The lipid phase was mixed with the aqueous phase (20 mL) containing surfactant at the same temperature using a Cyclone IQ2 with Sentry™ Microprocessor (USA) at 20,000 rpm for five (5) min. This mixture was passed through Nano-DeBee® (BEE International, South Easton, MA) at 20,000-30,000 psi for three to five cycles. Throughout the process, temperature was maintained at 60° C.

Response Surface Methodology (RSM)

A response surface design was used to evaluate how responses behave at all the studied variables in the experimental region using quadratic polynomial equation. The aim of RSM is to determine the conditions that provide process and product improvement (32). The objective of the present study was to select the lipid, oil and surfactant for the Nano-Luc formulation with the desired response. The particle size, entrapment efficiency, loading efficiency and release rate at 24 hr were used as dependent variables. The actual values of independent variables are reported in Table 1. The parameter level selection was based on a preliminary study and on findings in the literature (Table 1). Design-Expert software (V. 8.0.7.1, Stat-Ease Inc., Minneapolis, MN, USA) was used for the generation and evaluation of the statistical experimental design.

TABLE 1

Variables in response surface design.

| Independent Variables | Levels | | |
|---|---|---|---|
| | 1 | 2 | 3 |
| A: Luciferin (mg) | 50 | 100 | 200 |
| B: Lipids (700 mg) | Monosteol | Precirol | Geleol |
| C: Oils (330 mg) | Miglyol | MCT oil | Transcutol |
| D: Surfactant (480 µL) | Tween 20 | Tween 80 | Mixture (1:1) |

Dependent Variables
Y1: Mean Particle Size (nm)
Y2: Entrapment Efficiency (%)
Y3: Loading Efficiency (%)
Y4: 24 h Release rate (%)

Central Composite Design

A central composite design was utilized to further optimize significant factors and to assess main, interaction and quadratic effects of the factors on properties of Nano-Luc. Lipid and oil concentrations were selected as significant factors based on the RSM optimization desirability study results. Each of the factors was tested at five (5) different levels and five (5) center points were included. Design-Expert software was used for the design, analysis and plotting of the various 3D and contour graphs.

Optimization of Responses Using Desirability Function

The multiple response method makes use of an objective function called the desirability function. It reflects the desirable ranges for each response (di). The desirability for each response can be calculated at a given point in the experimental domain. The optimum is the point with the highest value for the desirability. The entrapment efficiency and loading efficiency were targeted to maximum, while particle size and release rate were limited to <200 nm and <50%, respectively, in the procedure, as these values confirm the desired product outcome. The desirability function of these parameters was calculated using Design-Expert software.

Characterization of Nano-Luc and NanoLuc-DiR

The particle size and zeta potential of nanoparticles were measured using Nicomp 380 ZLS (Particle Sizing Systems, Port Richey, FL). To measure the total amount of drug present in the system, 0.1 ml of formulation was mixed with 0.9 ml of tetrahydrofuran, and the mixture was centrifuged at 5000 rpm for 5 min. The supernatant was collected and absorption was measured at 327 nm.

Entrapment efficiency was determined using vivaspin centrifuge filters. 0.5 ml of formulation was placed on top of the vivaspin centrifuge filter membrane (molecular weight cut-off was 10,000 Daltons) and centrifuged for 20 min at 5000 rpm. About 20 µl flow-through was collected out of 500 µl at the bottom of vivaspin filter, and absorption was measured at 327 nm to determine the luciferin content. The drug loading was determined by centrifuging 1.0 ml of formulation at 16,000 g for 1.5 h, and sediment was dissolved in tetrahydrofuran. The content of luciferin was measured by absorption at 327 nm. Drug loading was calculated using following equation (33):

$$\text{Luciferin Content (\% w/w)} = (\text{mass of nanoparticle recovered})/\text{mass of Luciferin in nanoparticle} \times 100 \quad (1)$$

Drug Release Studies

Drug release studies were performed using USP 1 (basket) dissolution apparatus (Vankel, NC). One (1) ml of nanoparticle formulation was placed in a soaked cellulose membrane (6000-8000 molecular weight cut off), and ends were closed and placed inside the basket. The dissolution media (200 ml) was phosphate buffer saline (PBS) pH 7.4, containing 0.5% w/v Volpo-20 and 0.5% v/v Tween 80. The baskets were rotated at 50 rpm for 72 h at 37.0±0.1° C. The samples (0.5 ml) were collected at different time points with replacement of equal dissolution media. Luciferin content was measured at 327 nm.

Differential Scanning Calorimetry

The interaction of luciferin and Xenolight DiR with lipids and association of the nanoparticle formulation was evaluated using a DSCQ100 (TA instrument, DE). About 5 mg of formulation was weighed and sealed in an aluminum hermetic pan, and the thermal pattern was determined against an empty pan from 0° C. to 300° C. at 5° C. min$^{-1}$ heating rate. Transition temperatures were determined from the endothermic peak minima, while transition enthalpies were obtained by integration of the endothermic transitions using linear baselines. Graphical illustrations of observations are shown in FIGS. 8A-8F.

Accelerated Stability Studies

Figure 9:
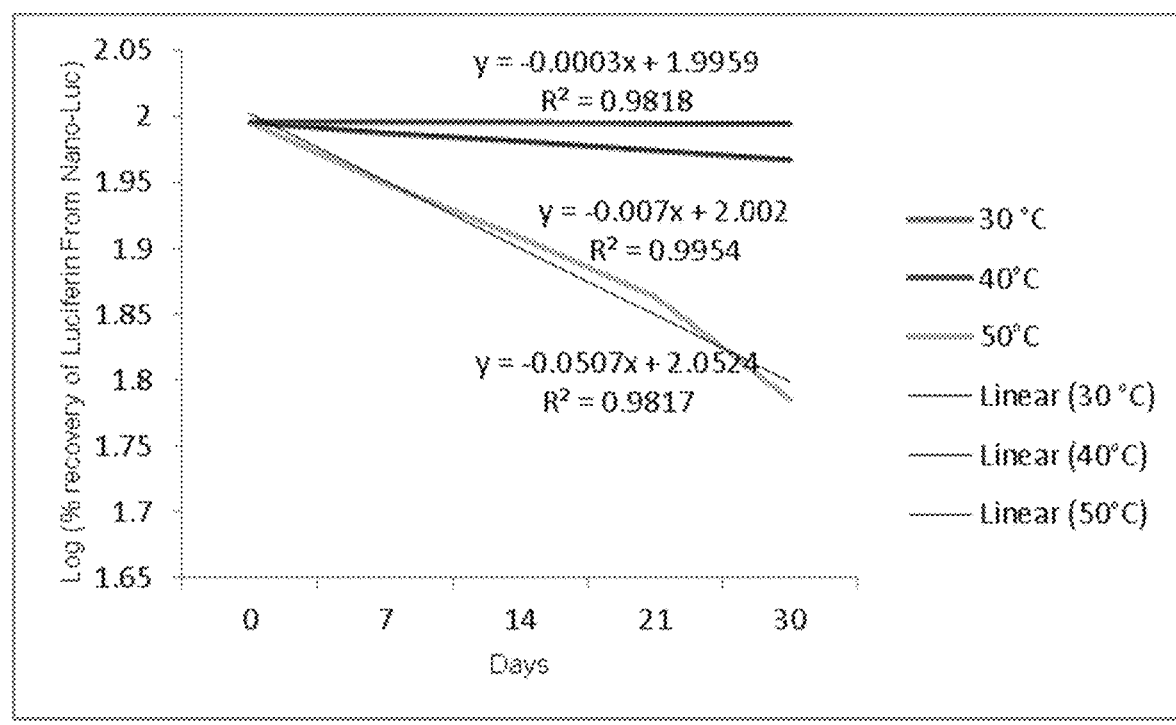
FIG. 9 is a graph of log (% luciferin recovery) vs. time for the effect of temperature (30° C., 40° C. and 50° C.) on Nano-Luc stability.

Nano-Luc and NanoLuc-DiR were stored at different temperatures 30±1° C., 40±1° C. and 50±1° C., along with at room temperature protected from light (mean temperature being 25.7±0.6° C.), for a month (34). Aliquots were removed after intervals of time (0 days, 7 days, 14 days, 21 days and one month), and formulations were analyzed for particle size, entrapment efficiency, release rate and luciferin content by methods described previously. As depicted in FIG. 9, a graph was plotted between log % luciferin remaining vs. time. The slope of the curve was determined from the graph, and degradation rate constant (K) was calculated by using the equation:

$$\text{Slope} = 2.303/K \quad (2)$$

Where, K is the degradation rate constant.

The effect of temperature (30° C., 40° C. and 50° C.) on degradation was studied by plotting log K vs. 1/T (Kelvin-1) (Arrhenius plot), as seen in FIG. 9. Further, the value of K at 25° C. and 8° C. ($K_8$ and $K_{25}$) was extrapolated from the Arrhenius plot, and shelf life at both room temperature (25° C.) and refrigerator temperature (8° C.) was predicted from Eq. (2).

In Vivo Tumor Models

In vivo tumors were grown using lung cancer cell lines (A549 and H460) and breast cancer cell lines (4T1 and MDA-MB-231). All the cell lines were modified for the luciferase reporter gene expression.

Xenograft Tumor Model

The adherent tumor cells were washed with PBS, harvested from conXuent cultures by 5-min exposure to 0.25% trypsin and 0.02% EDTA solution in an incubator. Trypsinization was stopped with medium containing 10% FBS. The cells were centrifuged, and the floating cells in the supernatant were discarded. The cell pellet was resuspended in medium containing 10% FBS and mixed thoroughly. Trypan blue staining was used to determine the number of viable cells. The resuspended cells were centrifuged, and cell dilutions of $2 \pm 10^6$ cells/100 µl were prepared in growth medium. The 100 µl of cell suspension was injected subcutaneously into the right flank area of each mouse. The mice were randomized into control and treatment groups when xenografts were palpable with a tumor size of 50 mm$^3$.

Orthotopic Tumor Model

The orthotopic tumor model was used to mimic the cancer in humans in athymic nu/nu mice (6-week old). Mice were anesthetized and a 5 mm skin incision was made to the left chest, 5 mm below the scapula. Hamilton syringes (1 mL) with 28-gauge hypodermic needles were used to inject the cell inoculums through the sixth intercostal space into the left lung. The needle was advanced to a depth of 3 mm and removed after the injection of the cells ($1 \times 10^6$ per mouse) suspended in 100 µLPBS (pH 7.4) into the lung parenchyma. Only cell suspensions of >90% viability, as determined by trypan blue exclusion, were used. Wounds from the incisions were closed with surgical skin clips. Animals were observed for 45 to 60 min until fully recovered. Mice developed lung tumors 10-14 days after inoculation of the cells, and mice were randomized in various groups after 10 days post tumor implantation.

Metastatic Tumor Model

Nu/Nu mice were anesthetized and tumor cells (2 million per mouse) were injected via tail vein. Only cell suspensions of >90% viability, as determined by trypan blue exclusion, were used. A pilot study showed that all the nude mice develop lung tumors at 10-14 days after intravenous injection of tumor cells. Ten days after tumor implantation, the animals were randomly divided into groups to receive treatment.

In Vivo Imaging

Bioluminescence/Fluorescence Imaging

Mice were anesthetized with isoflurane and imaged for different time points up to 24 hr following IP, IV and SQ injection of 150 mg/kg luciferin solution, Nano-Luc (equivalent to 150 mg/kg of luciferin) and NanoLuc-DiR (equivalent to 150 mg/kg of luciferin). Imaging was performed with an IVIS Spectrum (16). Bioluminescent signals were quantified using Living Image® software (Caliper Life Sciences., Alameda, CA.).

Tumor Multimodality (CT/DLIT/FLIT) Imaging

Mice were anesthetized with isoflurane and imaged following IP, IV and SQ injection of NanoLuc-DiR (equivalent to 150 mg/kg of luciferin). Imaging was performed with an IVIS SpectrumCT (35). Bioluminescent signals were quantified using Living Image® software (Caliper Life Sciences., Alameda, CA.).

Statistical Analysis

Pooled data were expressed as mean±standard deviations (SD) and model parameters as estimates±standard errors (SE). Means were compared between two groups by t-test and between three dose groups by one-way variance analysis (ANOVA); data were explored for two-way ANOVA analyses, where applicable. Correlations between doses and parameters were sought by use of the linear regression coefficient (r) and the coefficient of determination ($R^2$). Probability (p) values <0.05 were considered significant. All statistical analyses were performed using GraphPad Prism® 5.0 software (San Diego, CA).

Results

Experimental Design and Effect of Variables on Response

Luciferin containing nanoparticles were prepared using a hot melt homogenization method. The experimental runs with variables and corresponding responses for the 32 formulations tested are presented in Table 2.

Presentation of experiments with actual values for factor levels in design with their responses for particle size, entrapment efficiency, loading efficiency and 24 hr release rate. Each experiment was performed using three (3) replicates of different nanoparticles.

| Run | A: Luciferin mg | B: Lipids mg | C: Oils mg | D: Surfactant ul | Y1: Mean Particle Size | Y2: Entrapment Efficiency | Y3: Loading Efficiency % | Y4: 24 hr Release Rate |
|---|---|---|---|---|---|---|---|---|
| 1 | 100 | Monosteol | Miglyol | Mixture of Tween 20 and Tween 80 | 179 | 99 | 89 | 50.89 |
| 2 | 50 | Geleol | MCT oil | Tween 20 | 168 | 97 | 75 | 42.68 |
| 3 | 50 | Presirol | MCToil | Tween 80 | 180 | 94 | 76 | 59.64 |
| 4 | 200 | Geleol | MCT oil | Mixture of Tween 20 and Tween 80 | 173 | 99 | 69 | 39.89 |
| 5 | 100 | Presirol | Transcutol | Tween 80 | 168 | 94 | 60 | 59.32 |
| 6 | 100 | Presirol | Miglyol | Tween 80 | 179 | 96 | 90 | 49.98 |
| 7 | 50 | Geleol | Miglyol | Mixture of Tween 20 and Tween 80 | 200 | 97 | 91 | 57.5 |
| 8 | 200 | Geleol | Transcutol | Tween 80 | 210 | 96 | 67 | 48.36 |
| 9 | 100 | Monosteol | MCT oil | Tween 20 | 179 | 96 | 82 | 45.65 |
| 10 | 50 | Monosteol | MCT oil | Mixture of Tween 20 and Tween 80 | 168 | 91 | 86 | 50.25 |
| 11 | 200 | Presirol | Miglycol | Mixture of Tween 20 and Tween 80 | 187 | 93 | 91 | 57.32 |
| 12 | 100 | Presirol | Transcutol | Tween 80 | 188 | 92 | 67 | 54.32 |
| 13 | 100 | Presirol | Miglyol | Tween 80 | 175 | 95 | 92 | 59.35 |
| 14 | 200 | Presirol | Transcutol | Mixture of Tween 20 and Tween 80 | 172 | 89 | 59 | 61.32 |

-continued

Presentation of experiments with actual values for factor levels in design with their responses for particle size, entrapment efficiency, loading efficiency and 24 hr release rate. Each experiment was performed using three (3) replicates of different nanoparticles.

| Run | A: Luciferin mg | B: Lipids mg | C: Oils mg | D: Surfactant ul | Y1: Mean Particle Size | Y2: Entrapment Efficiency | Y3: Loading Efficiency % | Y4: 24 hr Release Rate |
|---|---|---|---|---|---|---|---|---|
| 15 | 200 | Presirol | MCT oil | Tween 80 | 198 | 82 | 81 | 56.31 |
| 16 | 200 | Monosteol | MCT oil | Mixture of Tween 20 and Tween 80 | 189 | 92 | 84 | 48.36 |
| 17 | 200 | Monosteol | Miglyol | Tween 20 | 192 | 96 | 91 | 47.69 |
| 18 | 50 | Presirol | Franscutol | Mixture of Tween 20 and Tween 80 | 167 | 89 | 65 | 44.36 |
| 19 | 100 | Presirol | MCT oil | Mixture of Tween 20 and Tween 80 | 158 | 89 | 72 | 48.36 |
| 20 | 100 | Monosteol | MCT oil | Tween 20 | 167 | 97 | 81 | 47.68 |
| 21 | 50 | Monosteol | Franscutol | Tween 20 | 162 | 94 | 73 | 44.98 |
| 22 | 200 | Presirol | MCT oil | Tween 20 | 176 | 86 | 64 | 56.35 |
| 23 | 50 | Monosteol | Miglyol | Tween 80 | 164 | 97 | 81 | 48,55 |
| 24 | 200 | Monosteol | Transcutol | Tween 80 | 167 | 95 | 69 | 43.98 |
| 25 | 200 | Geleol | Miglyol | Tween 80 | 173 | 91 | 84 | 47.85 |
| 26 | 100 | Monosteol | Miglyol | Mixture of Tween 20 and Tween 80 | 149 | 92 | 88 | 49.35 |
| 27 | 100 | Geleol | Transcutol | Mixture of Tween 20 and Tween 80 | 158 | 87 | 56 | 48.65 |
| 28 | 50 | Presirol | Transcutol | Tween 20 | 164 | 88 | 57 | 32.89 |
| 29 | 200 | Geleol | Transcutol | Tween 20 | 187 | 91 | 68 | 68.35 |
| 30 | 100 | Geleol | Miglyol | Tween 20 | 188 | 92 | 87 | 61.34 |
| 31 | 100 | Geleol | Miglyol | Tween 20 | 172 | 89 | 91 | 59.39 |
| 32 | 100 | Geleol | MCT oil | Tween 80 | 195 | 82 | 78 | 54.85 |

As can be seen in Table 2, the mean particle size ranged from 149 nm to 210 nm depending on the factor level selected during preparation. The response surface quadratic model was used for analysis purposes. Statistical analysis revealed that none of the factors were significant to influence mean particle size (Y1), as shown in Table 3.

TABLE 3

This table illustrates statistical analysis of mean particle size (Y1), entrapment efficiency (Y2), loading efficiency (Y3), and 24 hr release rate (Y4) in the Response Surface design.

|  | Y1: Mean Particle Size | | Y2: Entrapment Efficiency | | Y3: Loading Efficiency | | Y4: 24 hr Release Rate | |
|---|---|---|---|---|---|---|---|---|
|  | F value | p value | F value | p value | F value | p value | F value | p value |
| A: Luciferin | 2.4297 | 0.1798 | 1.3226 | 0.3021 | 0.1213 | 0.7418 | 6.3462 | 0.0453* |
| B: Lipids | 1.0120 | 0.4275 | 2.7413 | 0.1571 | 10.0924 | 0.0176* | 6.9900 | 0.0271* |
| C: Oils | 0.0677 | 0.9353 | 6.3760 | 0.0421* | 149.5454 | <0.0001* | 2.3294 | 0.1784 |
| D: Surfactant | 2.1018 | 0.2175 | 1.1472 | 0.3890 | 0.8709 | 0.4736 | 0.6808 | 0.5414 |

*Significant values at p <0.05

The entrapment efficiency was represented in percentage of loading efficiency, ranging from 82% to 99% depending on the factor level selected during preparation (see Table 2). The response surface quadratic model with inverse transform was used for analysis purposes. Statistical analysis revealed that oils were the significant factor to influence entrapment efficiency (Y2), as seen in Table 3. As shown in Table 2, for all formulations the loading efficiency (Y3) of Nano-Luc was in range of 56% to 92%. The most significant factor affecting the loading efficiency was shown to be oils (p<0.05) followed by lipids (p<0.05) used in the preparation of Nano-Luc.

An increase in release rate was observed with increase in luciferin concentration, and lipids were also significantly influencing the release rate. Effect of lipid- and oil-type factors on loading efficiency, entrapment efficiency, 24 hr release rate and mean particle size are shown in FIGS. 5A-5D.

Central Composite Design

After the lipids and oils were found as critical factors based on the screening design, a 2-factor, 5-level central composite design was applied to explore the optimum levels of these factors, as seen in Table 4.

TABLE 4

Presentation of experiments with actual values for variables in central composite design with their responses for entrapment efficiency, loading efficiency, and 24 hr release rate.

| Run | A:Monosteol (mg) | B:Miglyol (mg) | X1: Entrapment Efficiency (%) | X2: Loading Efficiency (%) | X3: 24 hr Release rate (%) |
|---|---|---|---|---|---|
| 1 | 600 | 250 | 86.64 | 71.58 | 58.25 |
| 2 | 600 | 250 | 85 | 74.25 | 57.69 |
| 3 | 300 | 400 | 57.36 | 79.36 | 67.05 |
| 4 | 600 | 250 | 86.58 | 72.69 | 56.98 |
| 5 | 600 | 250 | 84.36 | 74.23 | 55.89 |
| 6 | 900 | 100 | 95.36 | 58.95 | 35.68 |
| 7 | 600 | 462.13 | 87.25 | 99.25 | 61.35 |
| 8 | 900 | 400 | 98.35 | 99.51 | 45.98 |
| 9 | 1024.26 | 250 | 99.9 | 84.36 | 34.89 |
| 10 | 300 | 100 | 56.98 | 42.36 | 69.35 |
| 11 | 600 | 37.86 | 97.65 | 31.35 | 35.24 |
| 12 | 600 | 250 | 84.69 | 78.25 | 52.35 |
| 13 | 175.73 | 250 | 76.38 | 95.35 | 67.25 |

This methodology included 2 groups of design points, including 2-level factorial design points, axial or star points, and center points (36). Two independent factors were studied at 5 different levels, coded as $-\alpha$, $-1$, 0, 1, and $+\alpha$, to determine the main, interaction and quadratic effects of the solute and Soluplus concentrations on the selected responses. The value for alpha (1.414) was intended to fulfill the rotatability in the design. The other variables were fixed at the following values: luciferin (100 mg); surfactant (480 µl). The experimental runs with formulation variables and corresponding responses for the 13 tested formulations are presented in Table 4. The best fit for each of the responses was found for the quadratic models of Y1 and Y2, and the linear model of Y3. The statistical analyses for response following analyses of the models were described as the effect of various factors on the tested responses, as seen in Table 5.

TABLE 5

Statistical analysis of entrapment efficiency (X1), loading efficiency (X2) and 24 hr release rate (X3) in the Response Surface design.

| | X1: Entrapment Efficiency | | X2: Loading Efficiency | | X3: 24 hr Release Rate | |
|---|---|---|---|---|---|---|
| | EC | p value | EC | p value | EC | p value |
| Intercept | 85.454 | N/A | 74.2 | N/A | 0.01780 | N/A |
| A-Monosteol | 14.0790 | 0.0046 | 2.6497 | 0.4148 | 0.0049 | 0.0002 |
| B-Miglyol | −1.4172 | 0.6930 | 21.6981 | 0.0002 | −0.0028 | 0.0053 |
| AB | 0.6525 | 0.8972 | 0.89 | 0.8428 | −0.0016 | 0.1389 |
| A^2 | −1.9776 | 0.6089 | 5.9443 | 0.1127 | 0.0014 | 0.1094 |
| B^2 | 0.1773 | 0.9630 | −6.3331 | 0.0947 | 0.0016 | 0.0632 |

EC (Estimated Coefficient)
*Significant value at p <0.05

Figure 6A:
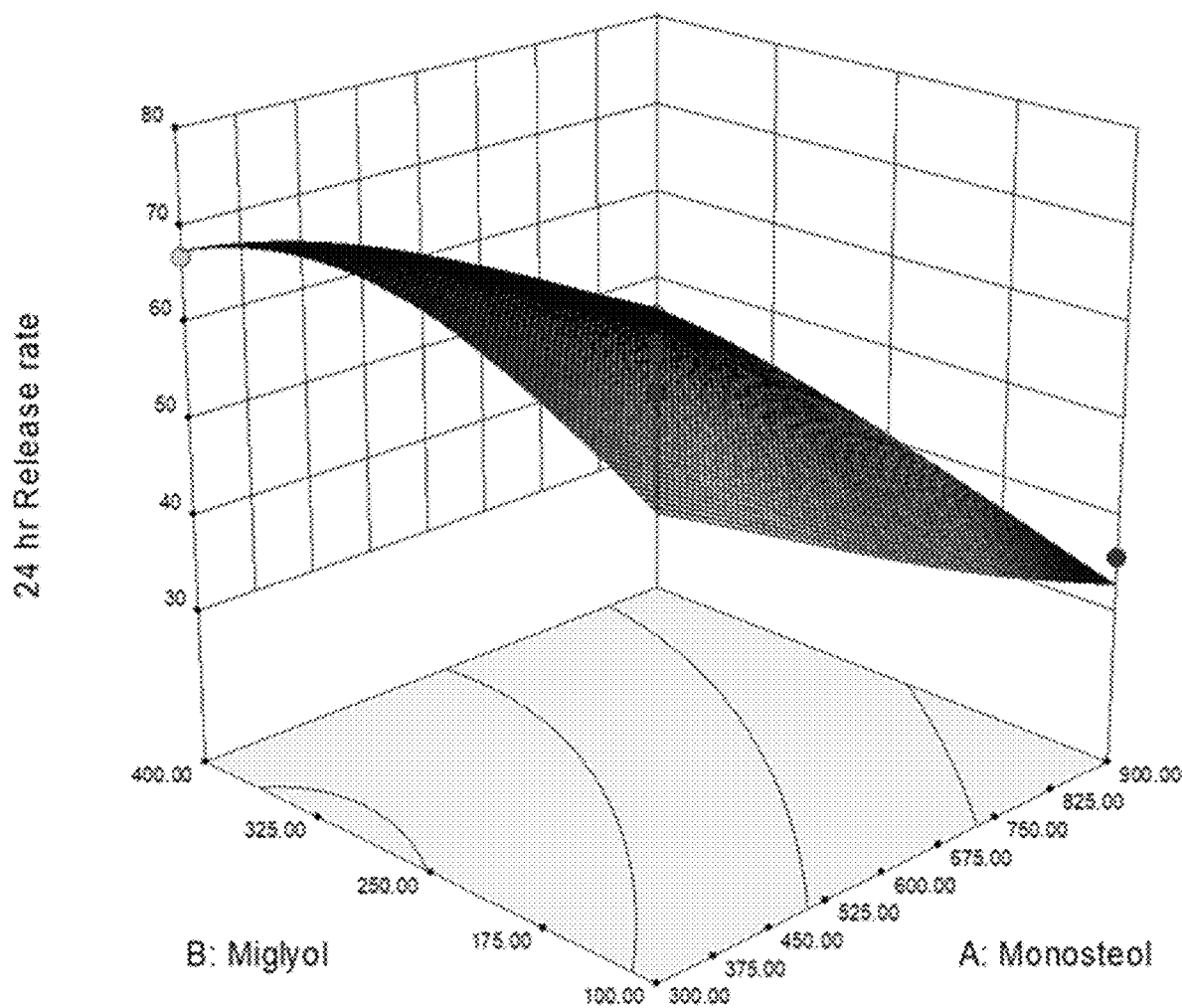
FIG. 6A is response surface plots showing the effect of different concentration of lipid and oil on release rate, loading efficiency and entrapment efficiency of Nano-Luc.
Figure 6A:
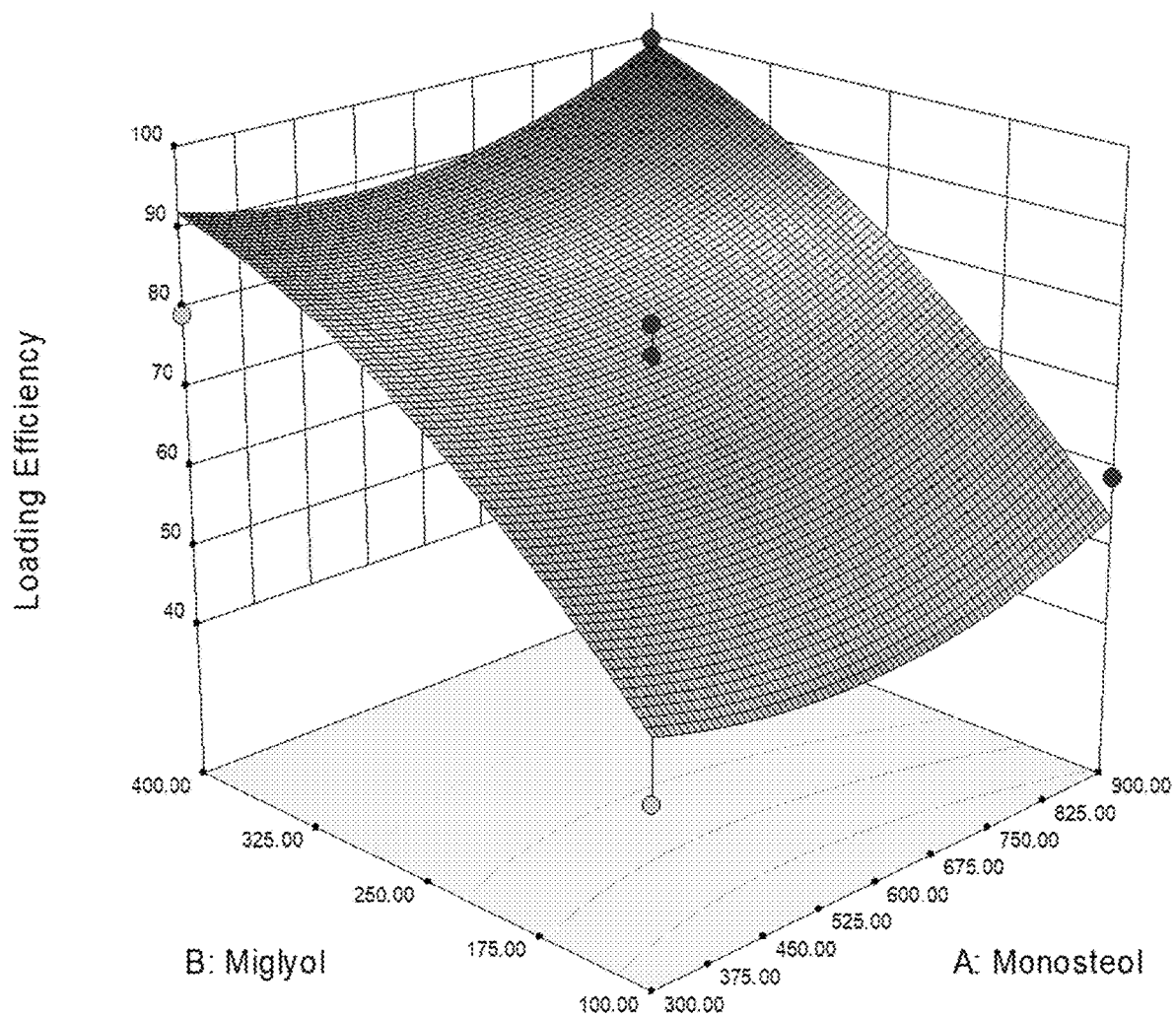
Figure 6A:
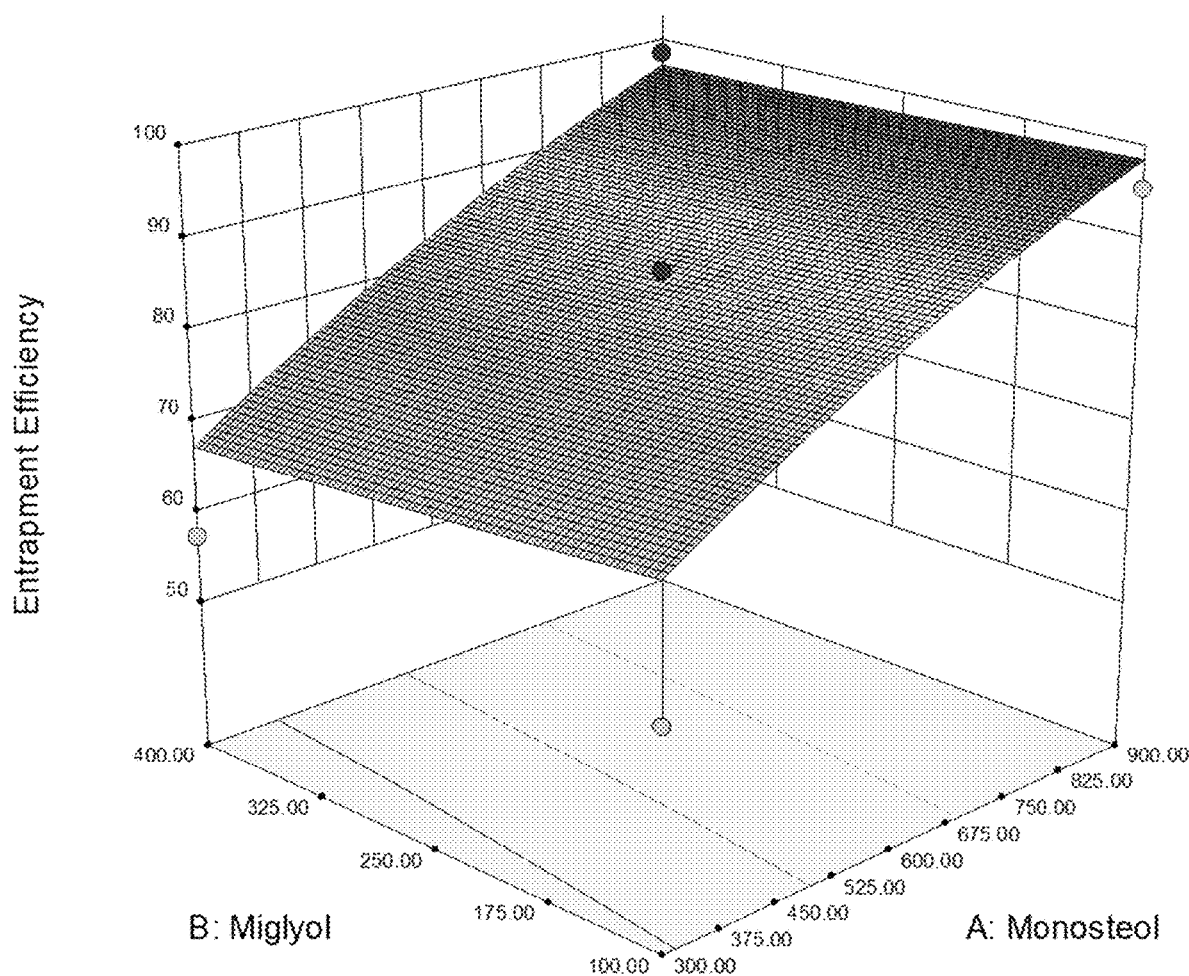
Figure 6B:
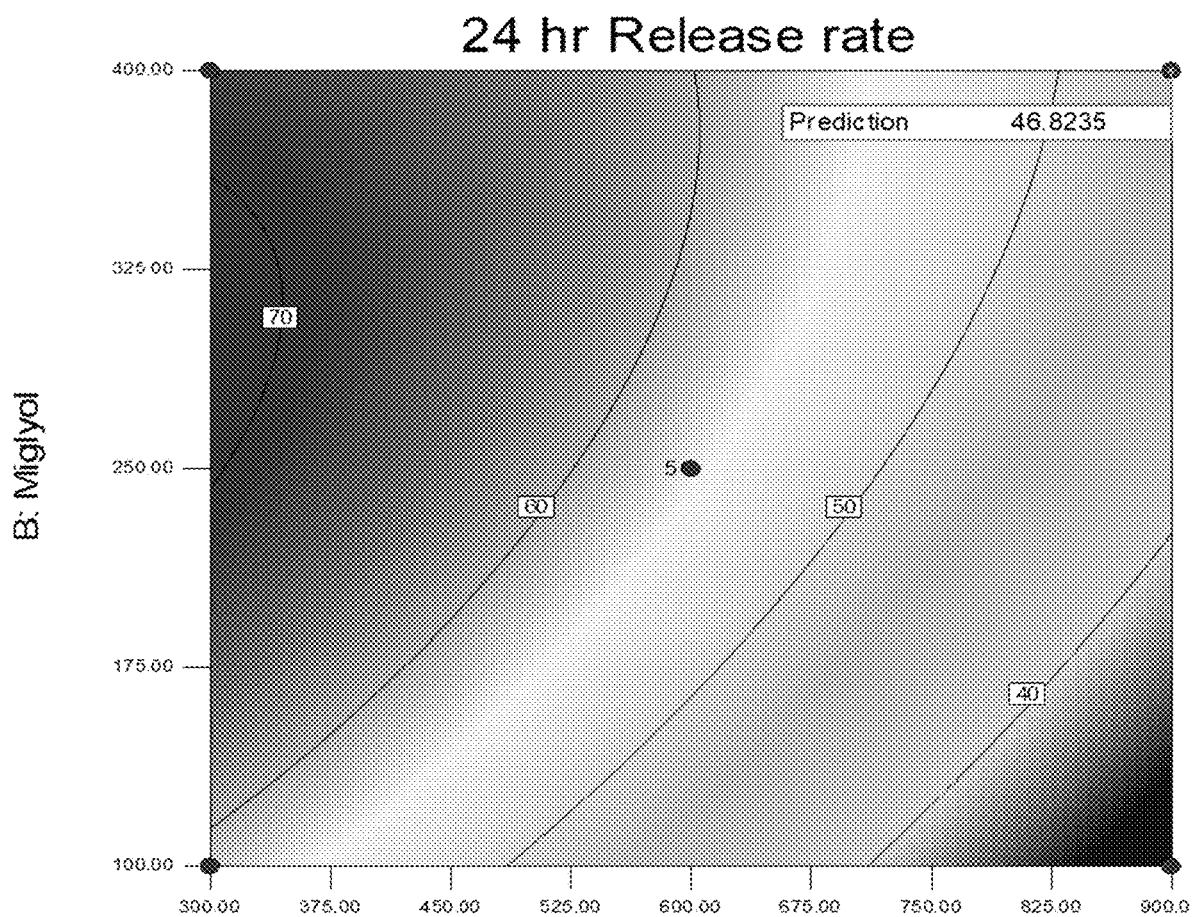
FIG. 6B is contour plots showing the effect of different concentration of lipid and oil on release rate, loading efficiency and entrapment efficiency of Nano-Luc.
Figure 6B:
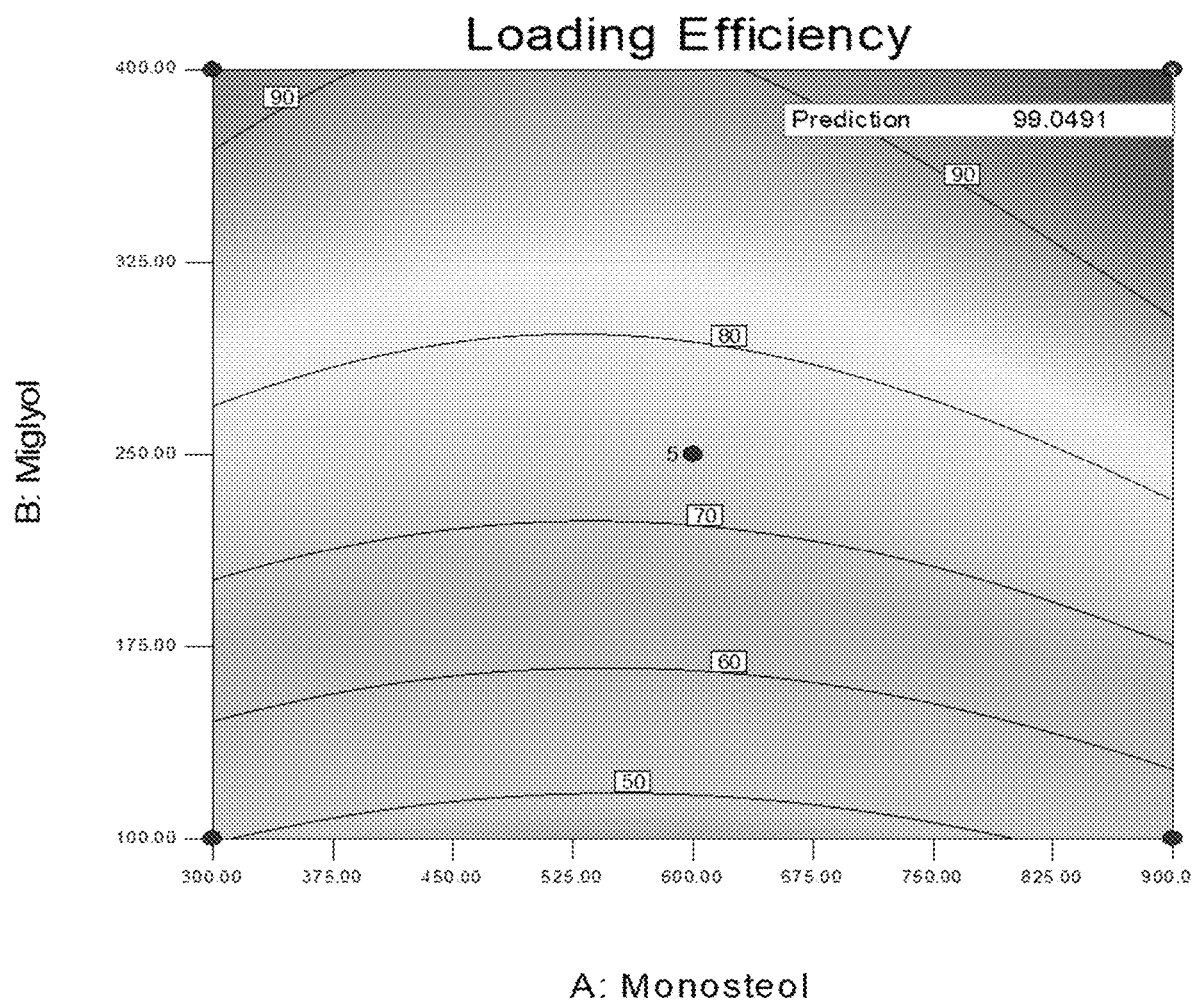
Figure 6B:
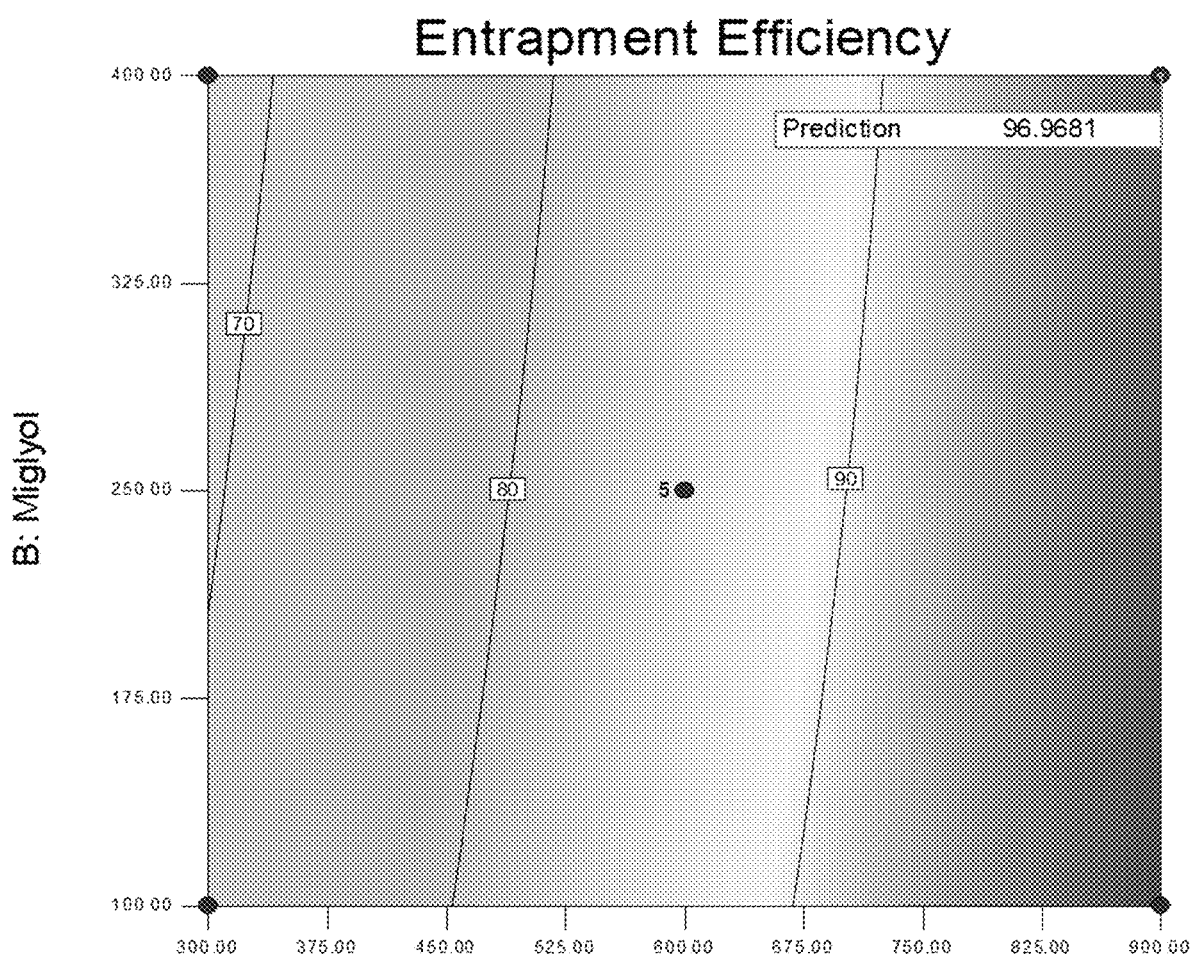
Figure 7A:
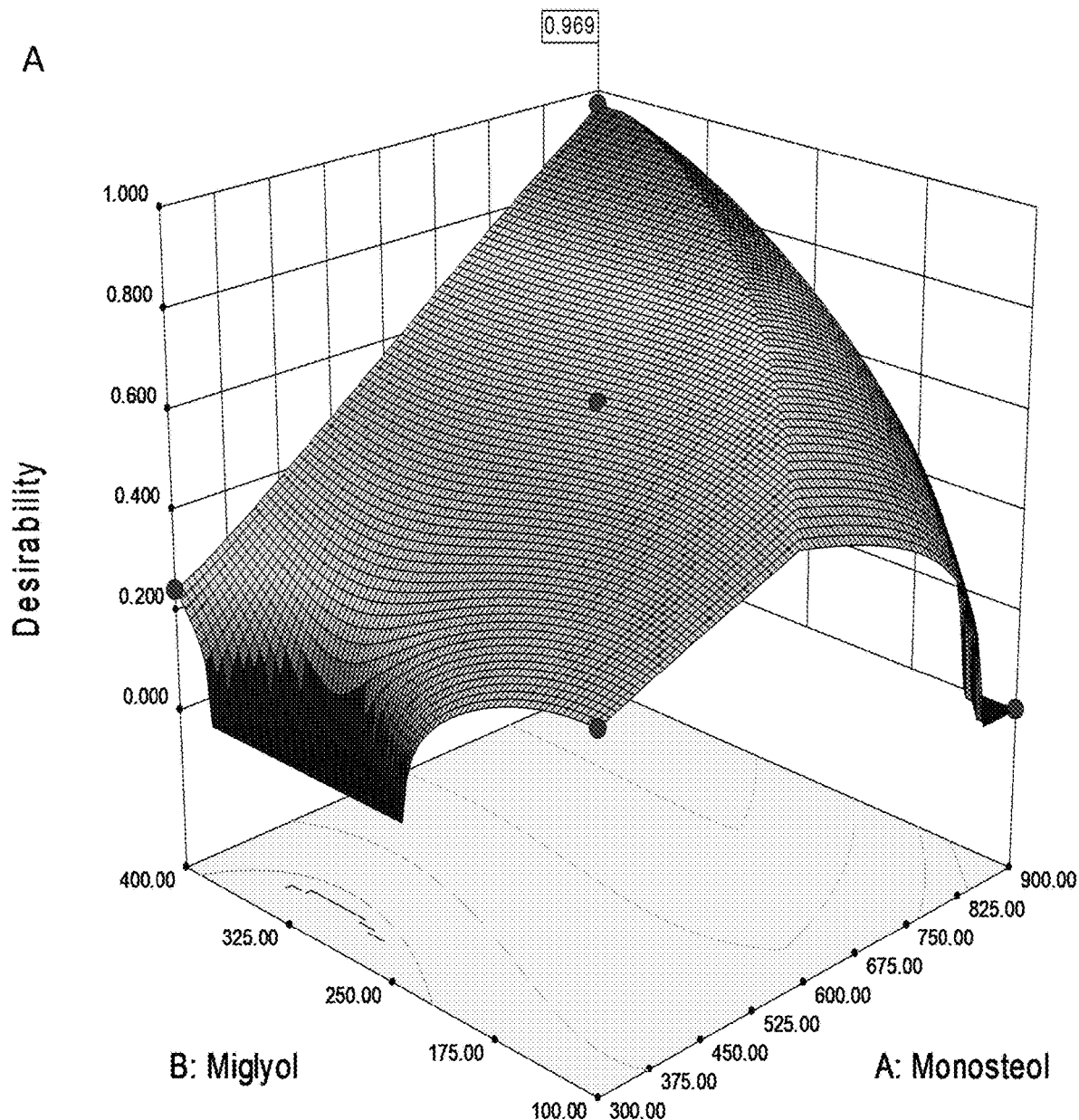
FIG. 7A is a response surface plot of desirability function.
Figure 7B:
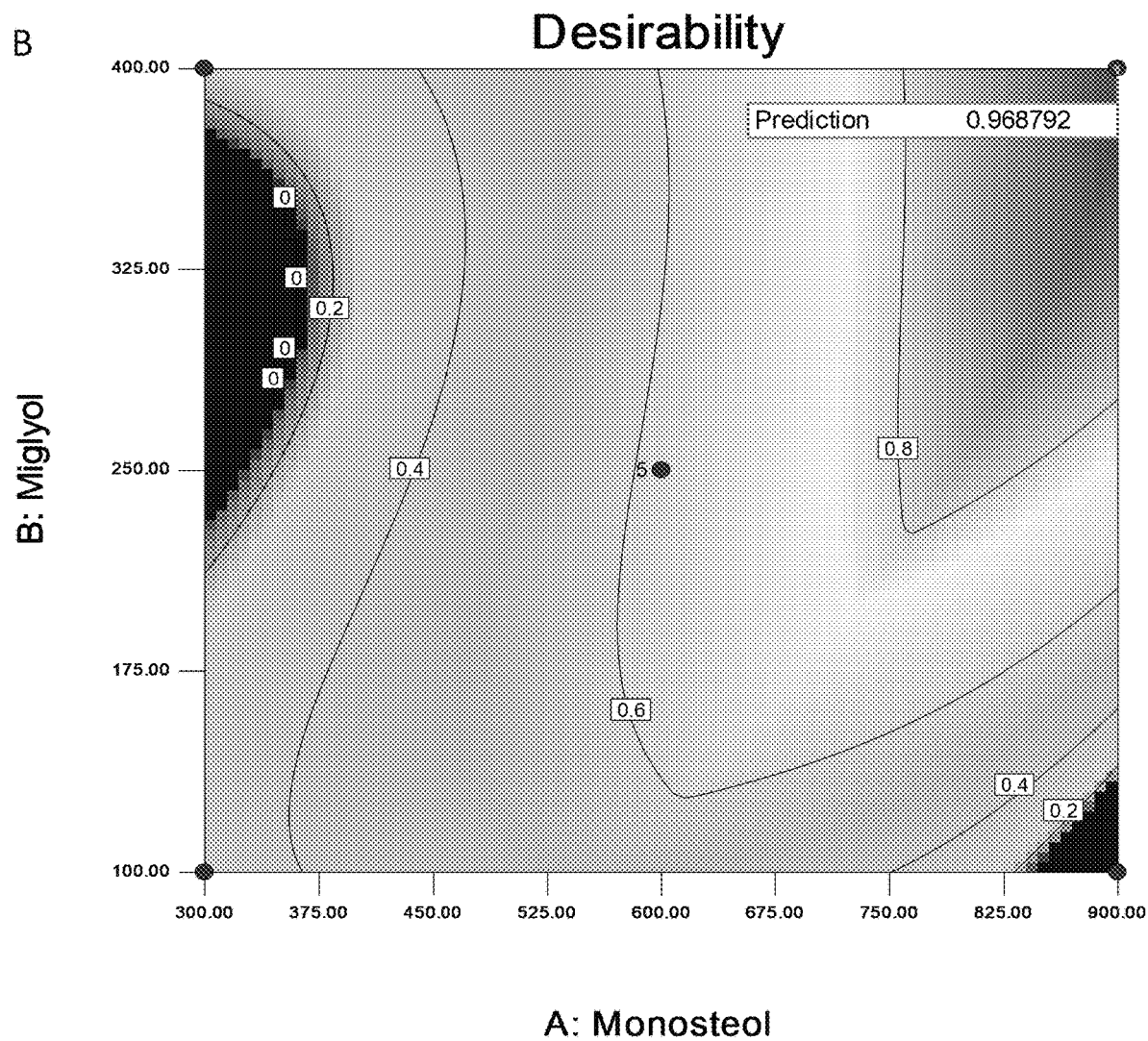
FIG. 7B is a contour plot of desirability function.

Contour plots and three-dimensional response surfaces were drawn to estimate the effects of the independent variables on each response (FIGS. 6A and 6B). The overall desirability response was calculated from the individual desirability of each of the responses using DOE v8.0.7. The optimized composition was identified with a desirability value of 0.968 (FIGS. 7A and 7B).

Differential Scanning Calorimetry (FIGS. 8A-8F)

Figure 8A:
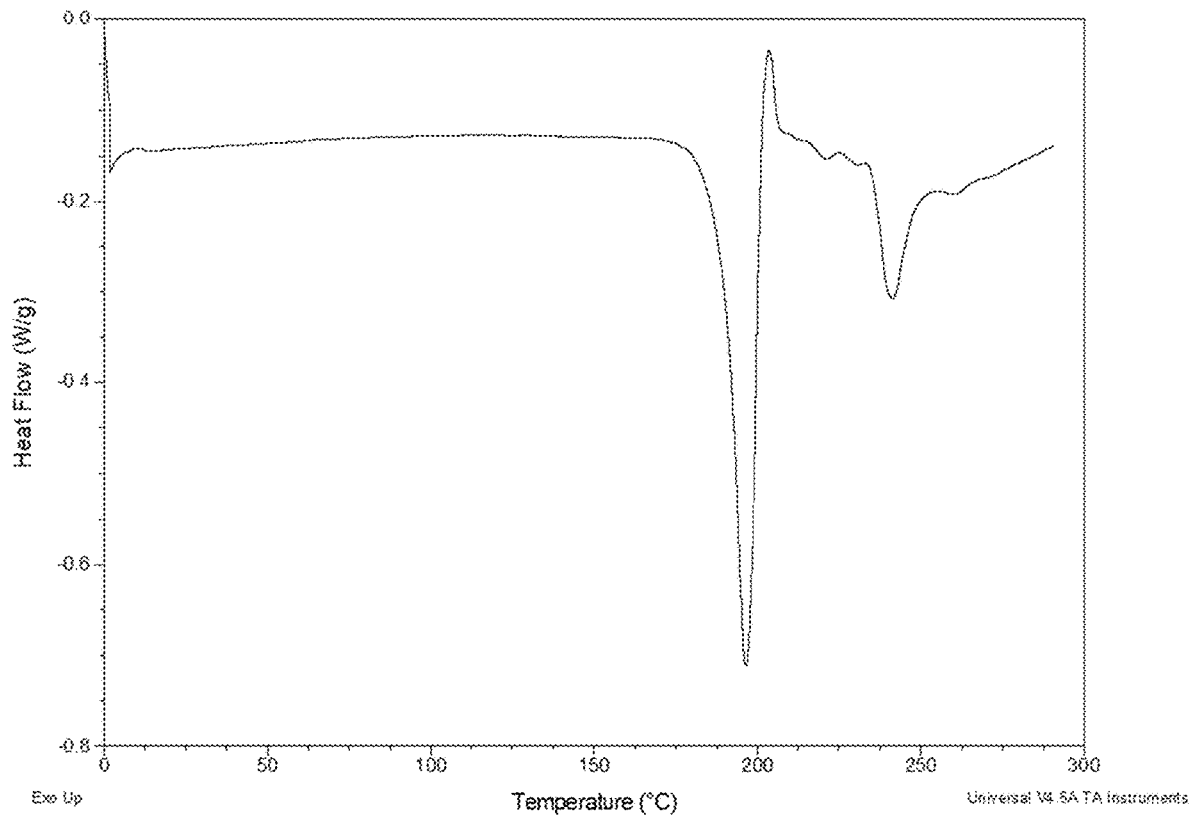
FIG. 8A depicts differential scanning calorimetry of luciferin.
Figure 8B:
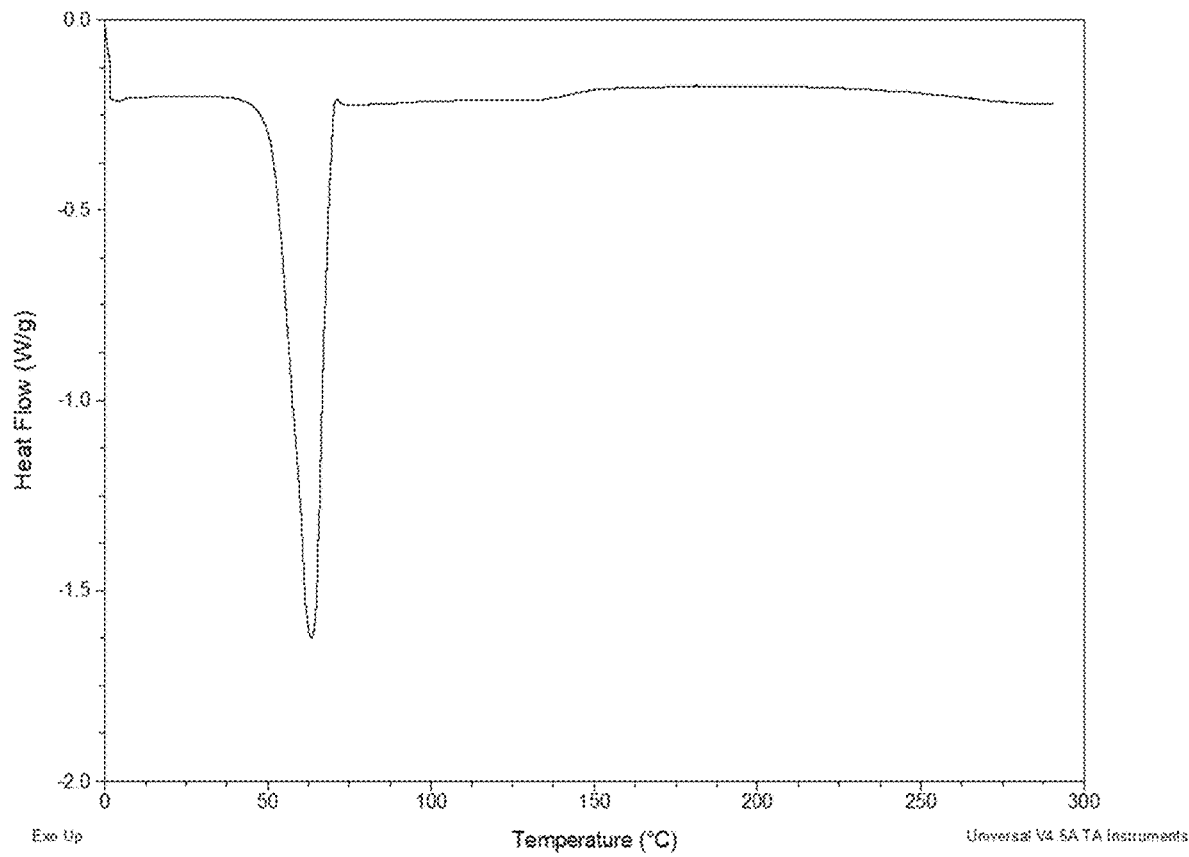
FIG. 8B depicts differential scanning calorimetry of Geleol™.
Figure 8C:
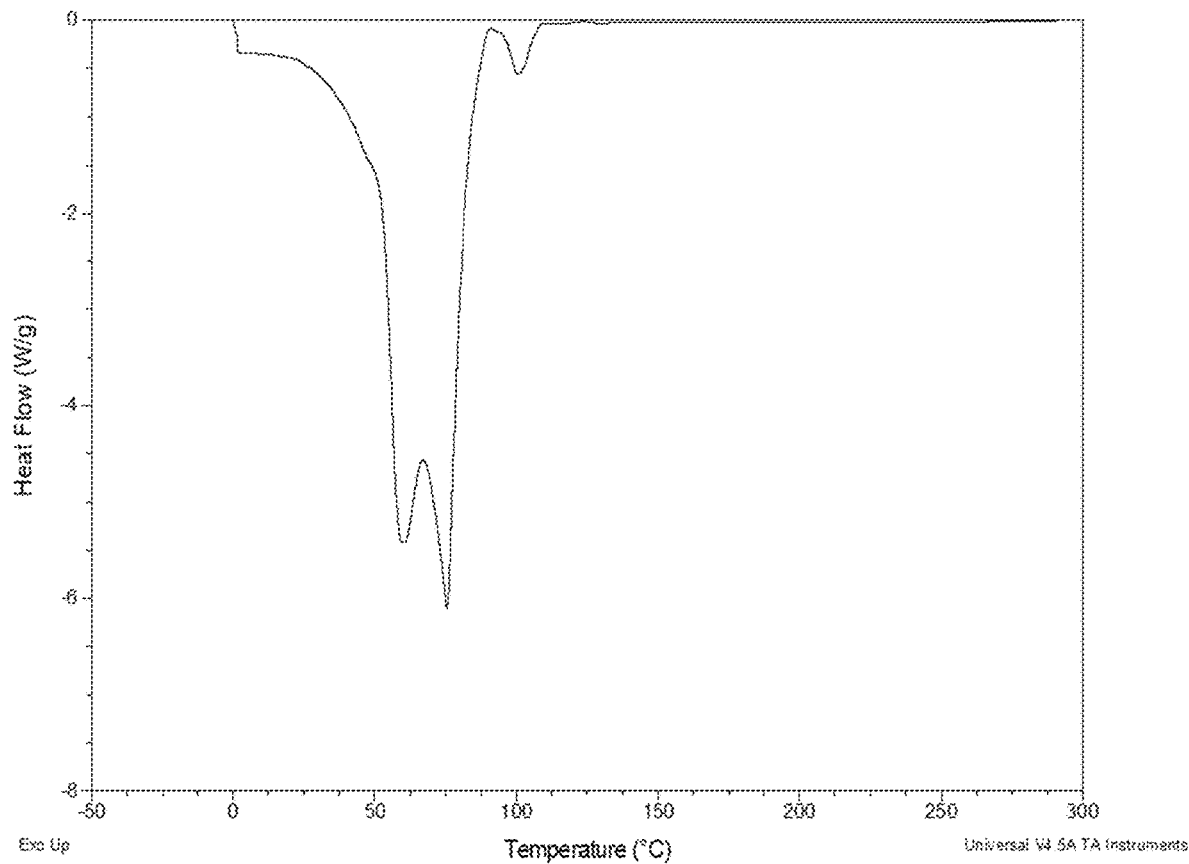
FIG. 8C depicts differential scanning calorimetry of Nano-Luc (formulation 1).
Figure 8D:
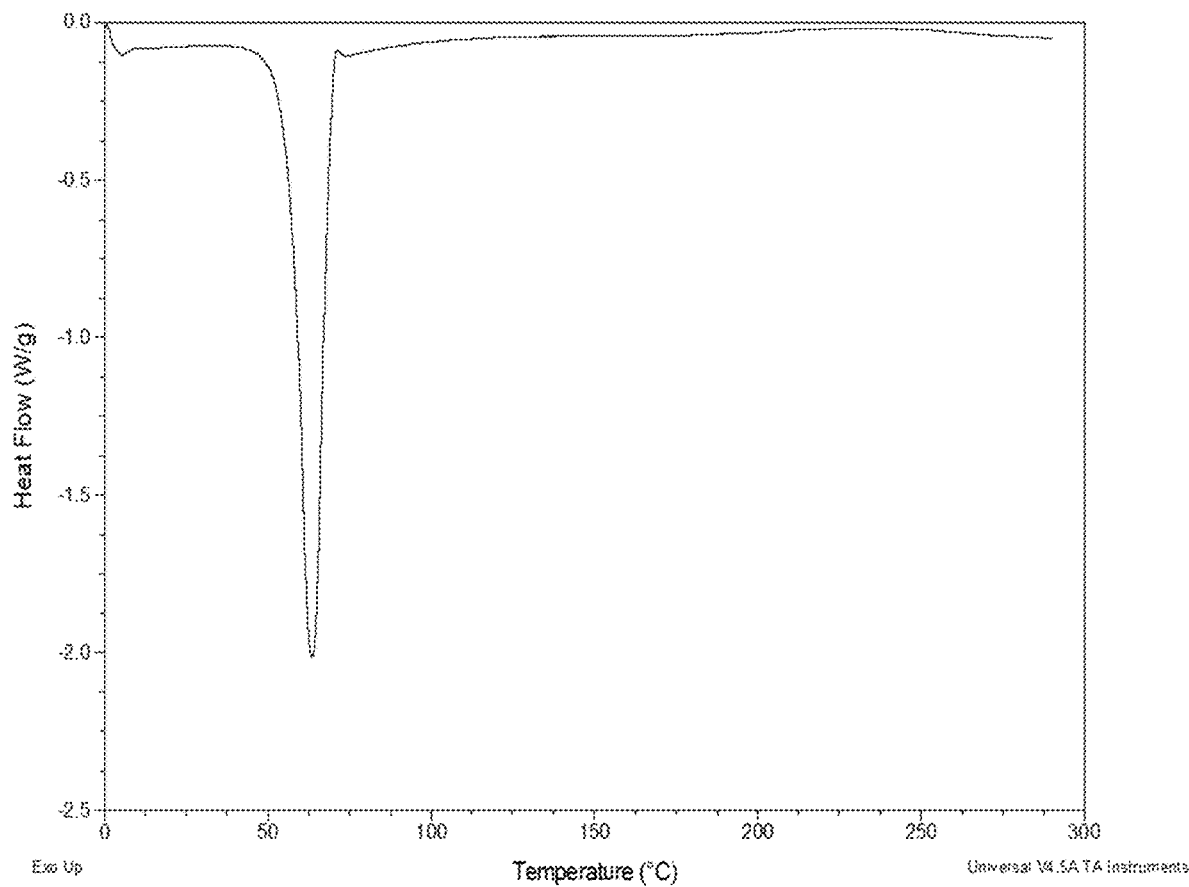
FIG. 8D depicts differential scanning calorimetry of Precirol™.
Figure 8E:
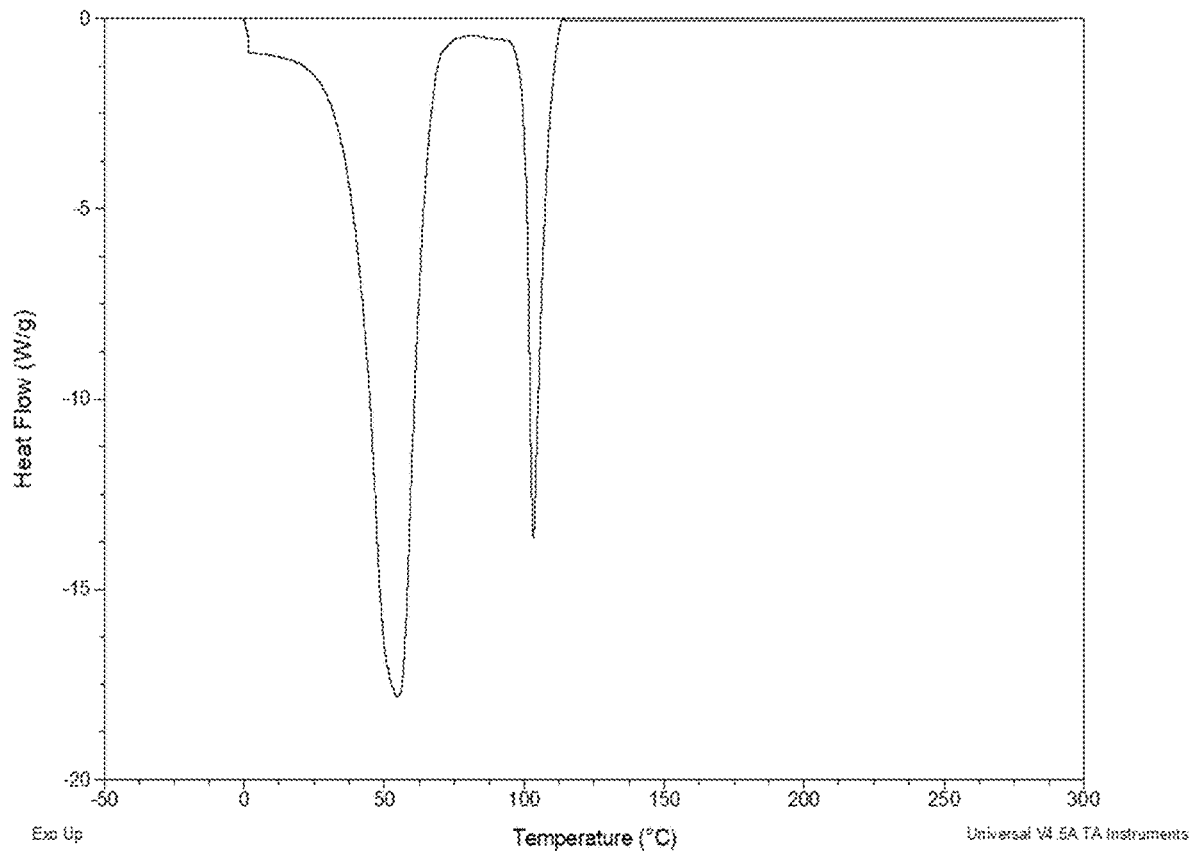
FIG. 8E depicts differential scanning calorimetry of Nano-Luc (formulation 2).
Figure 8F:
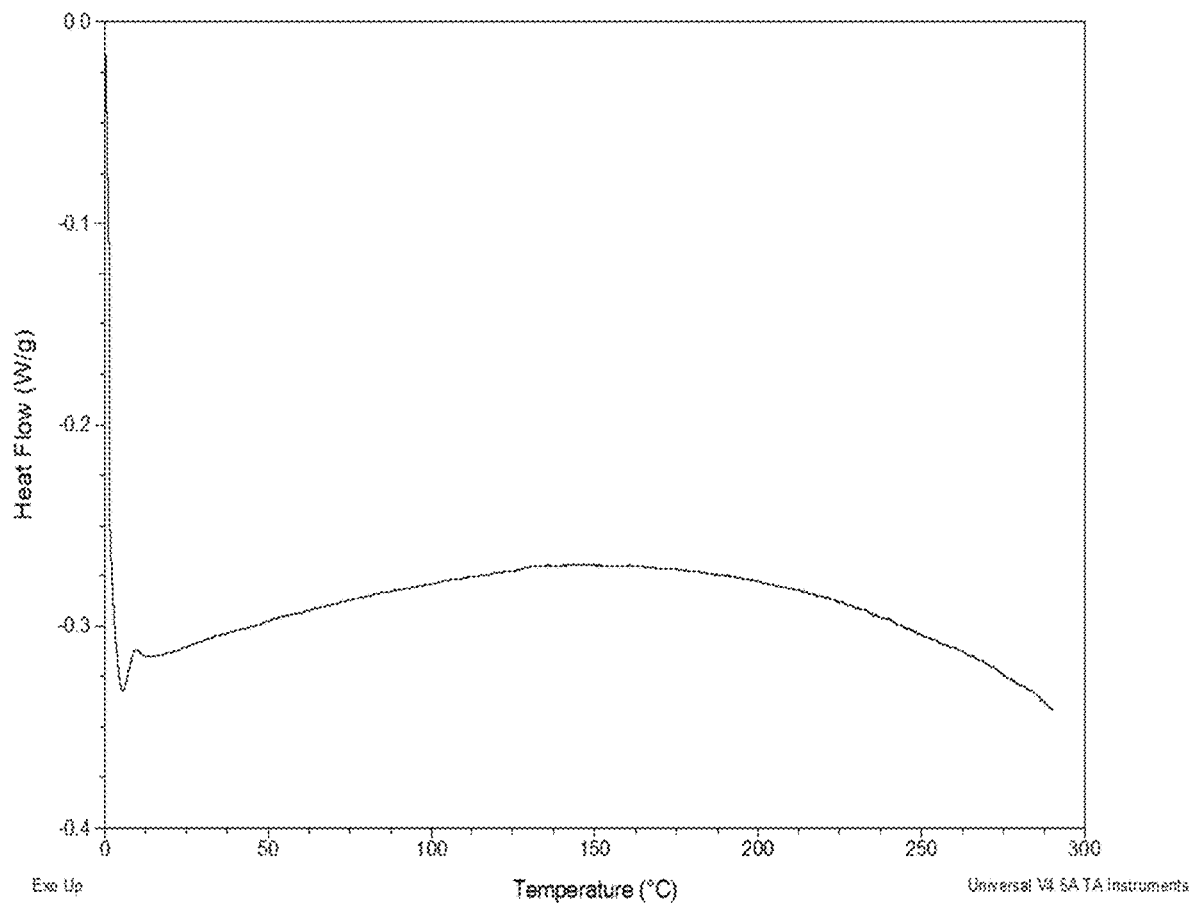
FIG. 8F depicts differential scanning calorimetry of Miglyol™.

For the free luciferin, the thermogram revealed a small, clear event at about 197° C. (FIG. 8A). No melting was observed before or during the process which can therefore most likely be attributed to a solid-solid phase transformation. The new modification was stable upon cooling. Upon further heating, a very pronounced DSC endothermic peak appeared at about 237° C. (FIG. 8A), and subsequently, the drug decomposed and turned black. The DSC thermogram of Precirol™ and Monosteol™ alone showed a sharp endothermic peak at about 63° C.

Following the addition of Miglyol™ and luciferin, there was a depression in the endothermic peak mainly because these entities behave as impurities. Also, DSC studies were performed to confirm the absence of drug excipients interactions. The DSC thermograms of physical mixture of components are shown in FIG. 9 in the same ratio as formulation and Nano-Luc. The DSC thermogram showed a sharp endothermic peak for luciferin at 197° C. and for Precirol™ at 63° C. No considerable shift in the position of endothermic peaks was observed in the DSC thermogram of physical mixture.

Stability Studies

Accelerated stability studies were conducted on Nano-Luc using the particle size, loading efficiency, and entrapment efficiency as the prime parameters. There was a slight increase in the particle size during the one-month storage from the 172±5.62 nm to 188.56±7.80 nm with not much change in PDI (i.e., initially it was 0.330±0.06 and after 1 month it was 0.348±0.01).

The entrapment efficiency and loading efficiency (%) of Nano-Luc batch initially was found to be 97.66±2.72% and 96.12±3.86%, respectively. After a month, the entrapment efficiency and loading efficiency of Nano-Luc batch was found to be 96.67±0.14% and 94.12±2.34%, respectively, indicating that the drug can be retained within the nanoparticles for the sufficient period of time. Also, the accelerated stability studies at 30° C., 40° C. and 50° C. were conducted and percentage recovery of luciferin from Nano-Luc was measured at different time points, as seen in FIG. 9.

Regarding storage of the Nano-Luc, there were no significant alterations in the size, PDI and entrapment efficiency of the nanoparticles. There was a decrease in loading efficiency at 50° C., since the melting point confirmed by DSC (FIGS. 9B and 9D) was near 60° C. A possible reason is the alteration of the lipid matrix and leaching of luciferin from the caged matrix.

In Vivo Imaging and Kinetics of Free Luciferin and Nano-Luc/NanoLuc-DiR

Figure 12A:
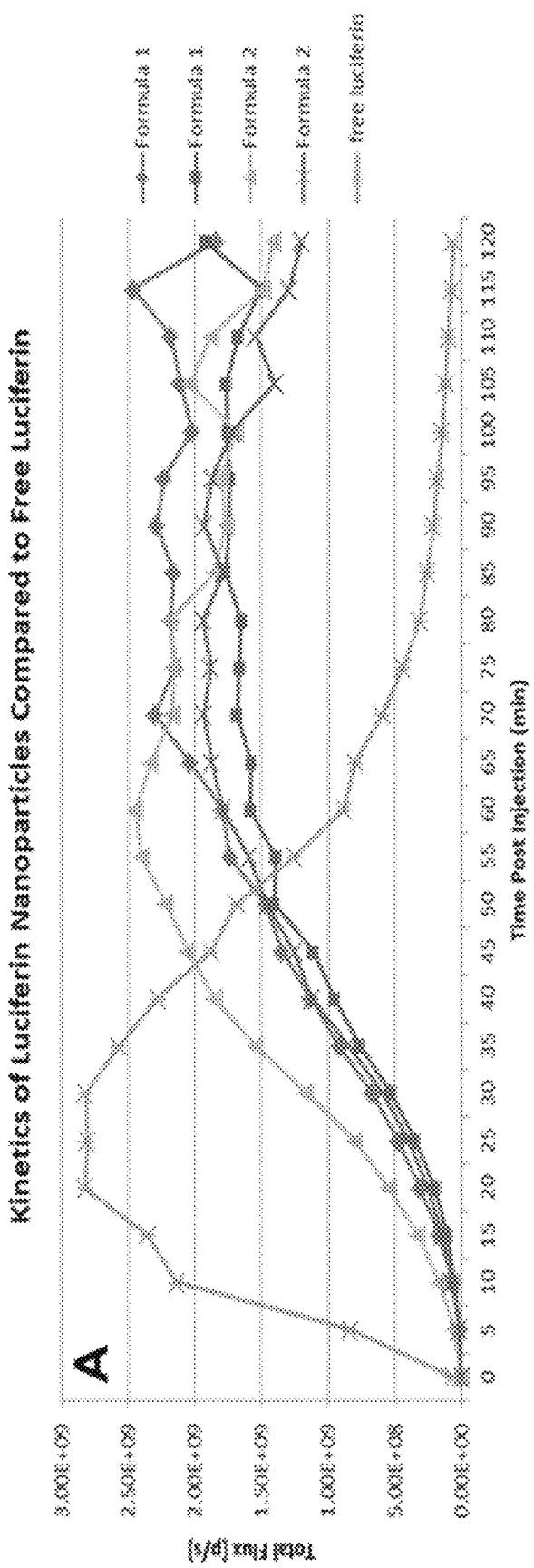
FIG. 12A is a graphical illustration showing in vivo kinetics of Nano-Luc compared to free luciferin, total flux of bioluminescence vs. time plot following IP injection of Nano-Luc and free luciferin.
Figure 12B:
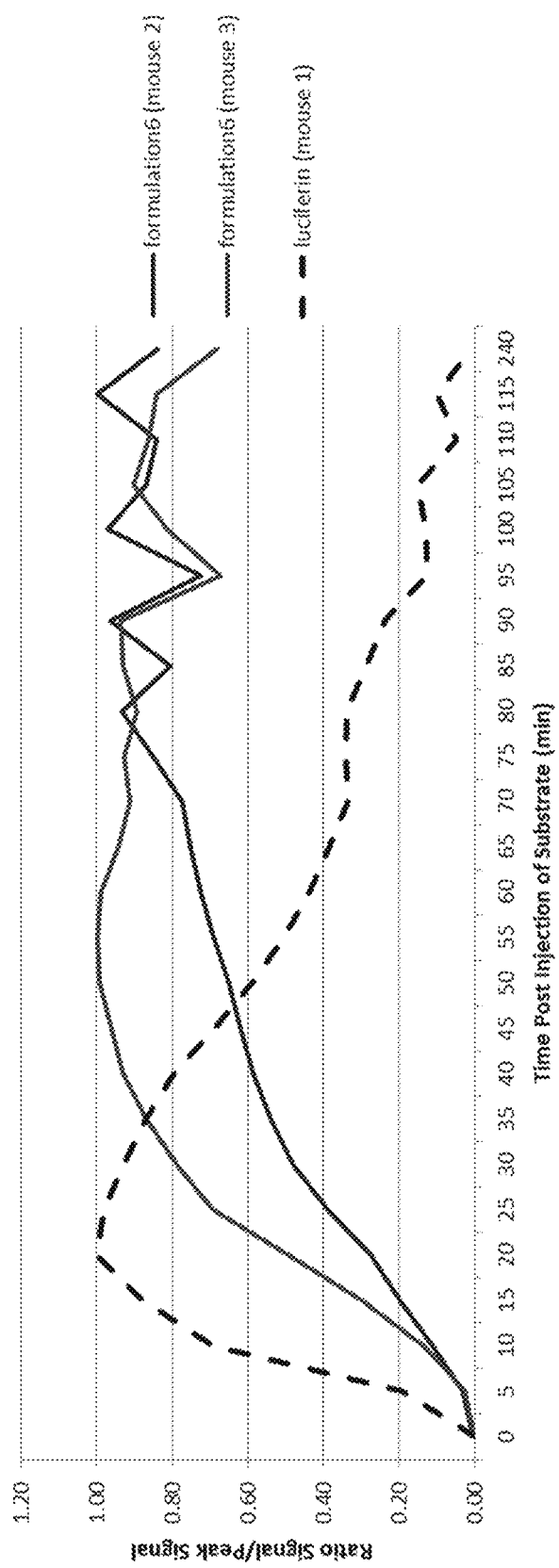
FIG. 12B is a graphical illustration showing in vivo kinetics of Nano-Luc compared to free luciferin, normalized to peak signal flux vs. time plot following subcutaneous injection of Nano-Luc and free luciferin.
Figure 12C:
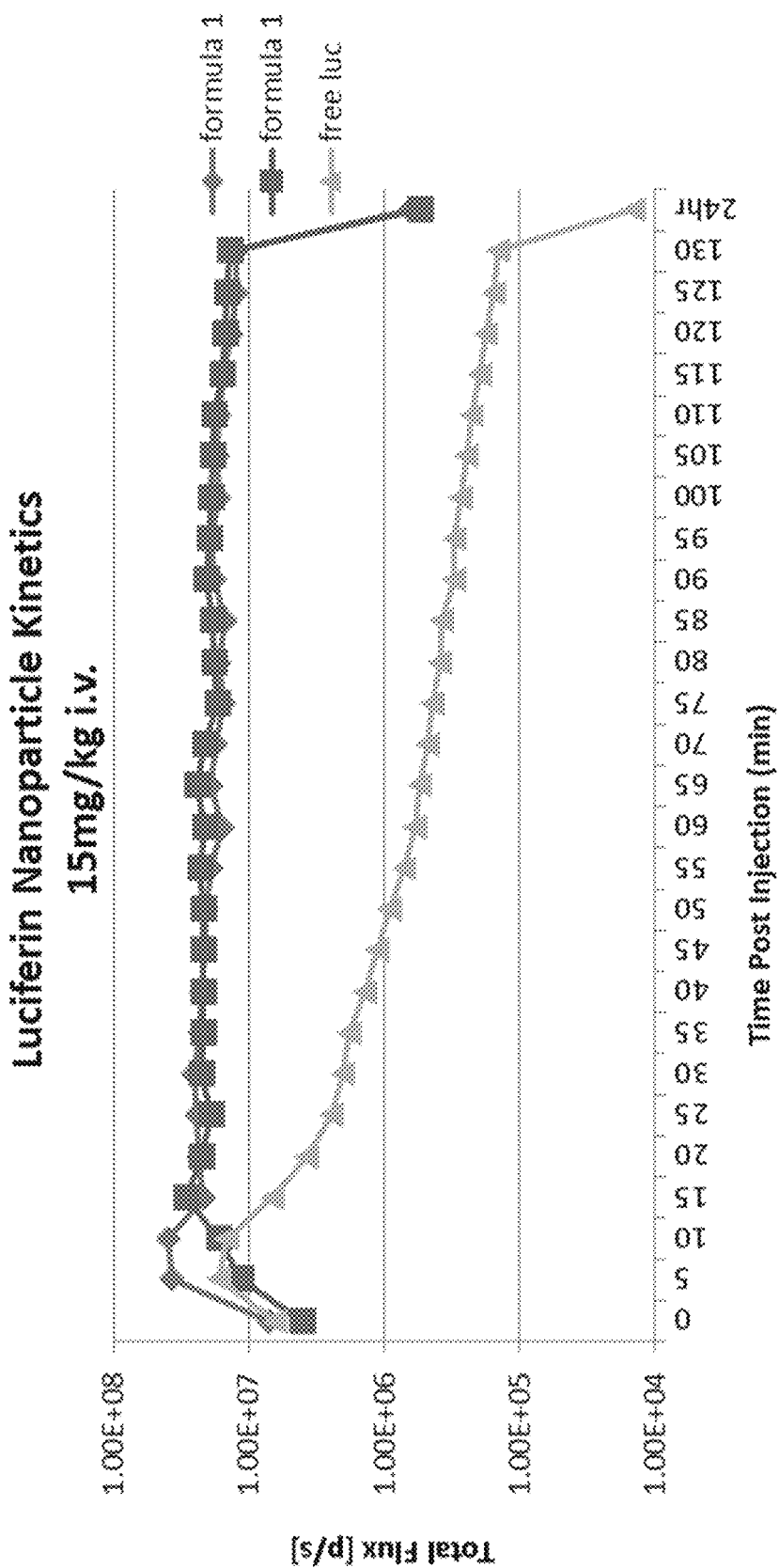
FIG. 12C is a graphical illustration showing in vivo kinetics of Nano-Luc compared to free luciferin, total flux of bioluminescence vs. time plot following IV injection of Nano-Luc and free luciferin.

Free luciferin was cleared from circulation within 60 min, as is apparent in 5 min and 120 min images in 4T1-luc models. With a matched intensity color map and total injected luciferin, the images acquired for Nano-Luc luciferin in formulations are compared to that of free luciferin for the corresponding animal models (FIGS. 12A-12C). General trends of short circulation of free luciferin, fast release from Nano-Luc (IV), and slow release from Nano-Luc (IP/SC) over time were observed for all tumor models.

Figures 10A, 10B:
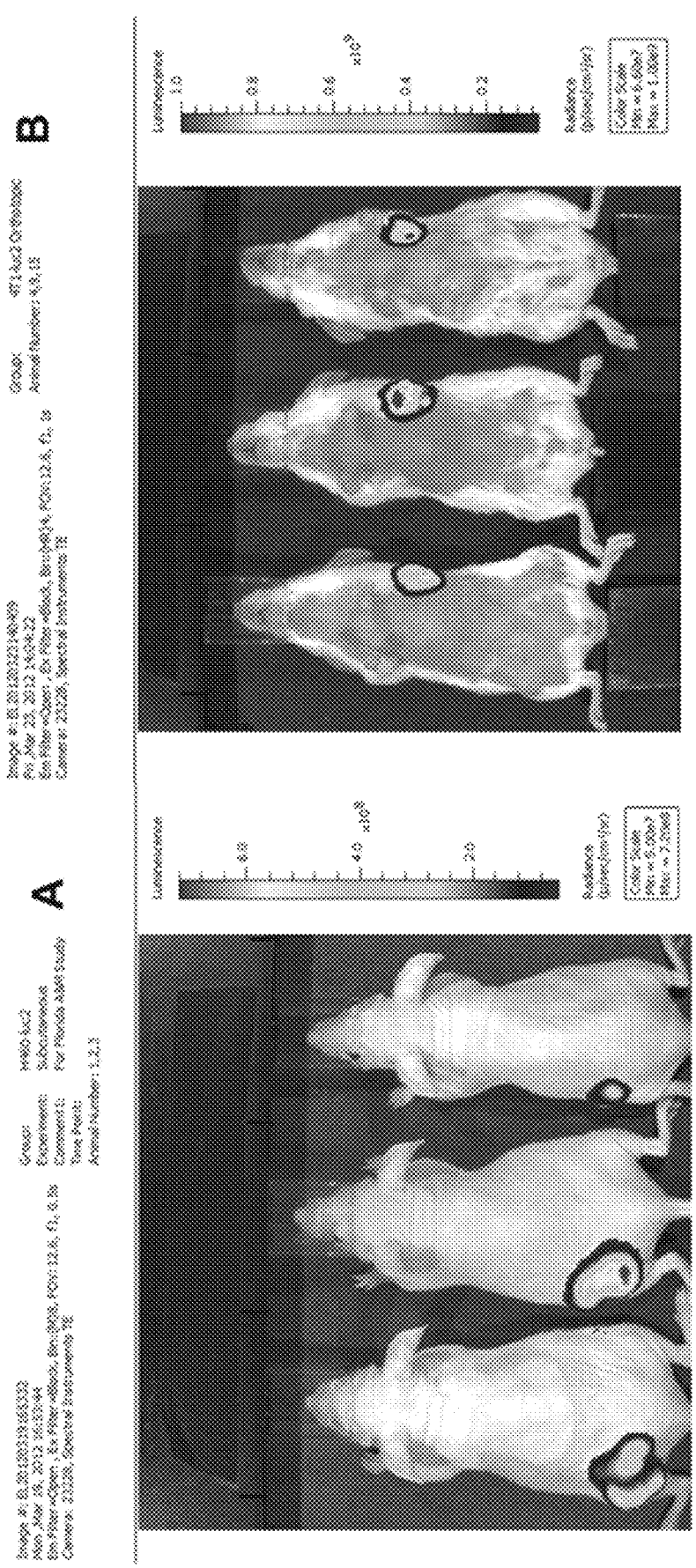
FIG. 10A depicts Nano-Luc tumor imaging in mice with subcutaneous 4T1-luc2 tumors using 150 mg/kg luciferin equivalent Nano-Luc by IP.
FIG. 10B depicts Nano-Luc tumor imaging in mice with orthotopic 4T1-luc2 tumors using 150 mg/kg luciferin equivalent Nano-Luc by IP.
Figure 11A:
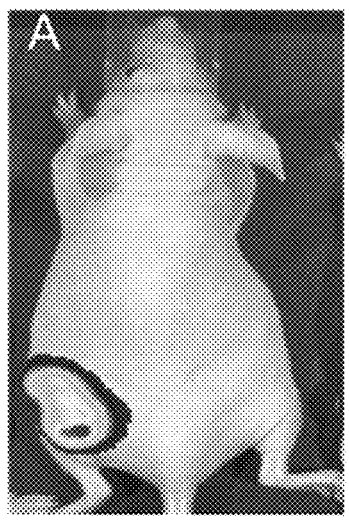
FIG. 11A depicts Nano-Luc tumor imaging in mice with subcutaneous H460-luc2 tumors using 150 mg/kg luciferin equivalent Nano-Luc by IV.
Figure 11B:
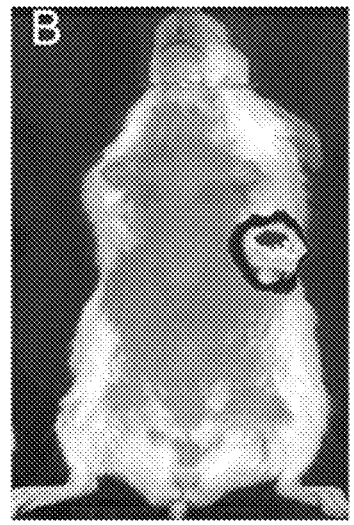
FIG. 11B depicts Nano-Luc tumor imaging in mice with orthotopic 4T1-luc2 tumors using 150 mg/kg luciferin equivalent Nano-Luc by IV.
Figure 11C:
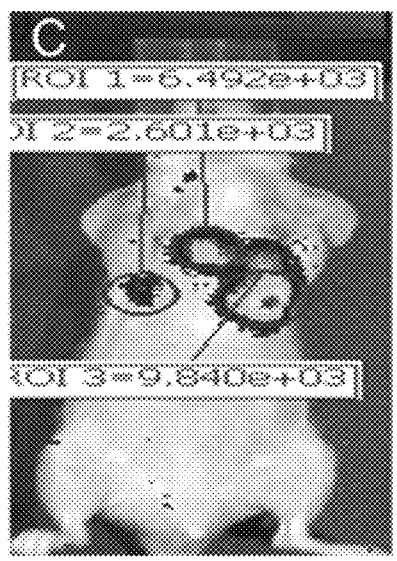
FIG. 11C depicts Nano-Luc tumor imaging in mice with mb231-luc2 metastatic tumors using 150 mg/kg luciferin equivalent Nano-Luc by IV.

Bioluminescence intensities quantified by drawing an ROI on each tumor as well as on the lower back of the animal showed similar PK profiles. The bioluminescence images were then quantified and used to evaluate the pharmacokinetics of free and Nano-Luc luciferin in 4T1-luc tumor models, as seen in FIGS. 10A and 10B. A rapid clearance of free luciferin was observed with a similar kinetic in all models (FIG. 12A-12B) with an estimated tin value of more than 2 hr in IP/SC delivery of Nano-Luc. Intravenous Nano-Luc luciferin, however, showed a two phase release kinetic, a rapid release in the early phase (t<30 min), followed by a slower steady release kinetic (FIG. 12C).

As seen in FIG. 12C, radiance resulting from the injection of Nano-Luc increased over the first hour and remained steady for another 4 hr and started declining slowly. However, radiance was detectable over 24 hr. With free luciferin, during the first 30 minutes, a rapid increased in radiance was observed; after 30 minutes, a rapid decline can be seen. Luciferin loaded in Nano-Luc had a 400-fold greater phase II half-life in circulation as compared to free luciferin.

Figure 13A:
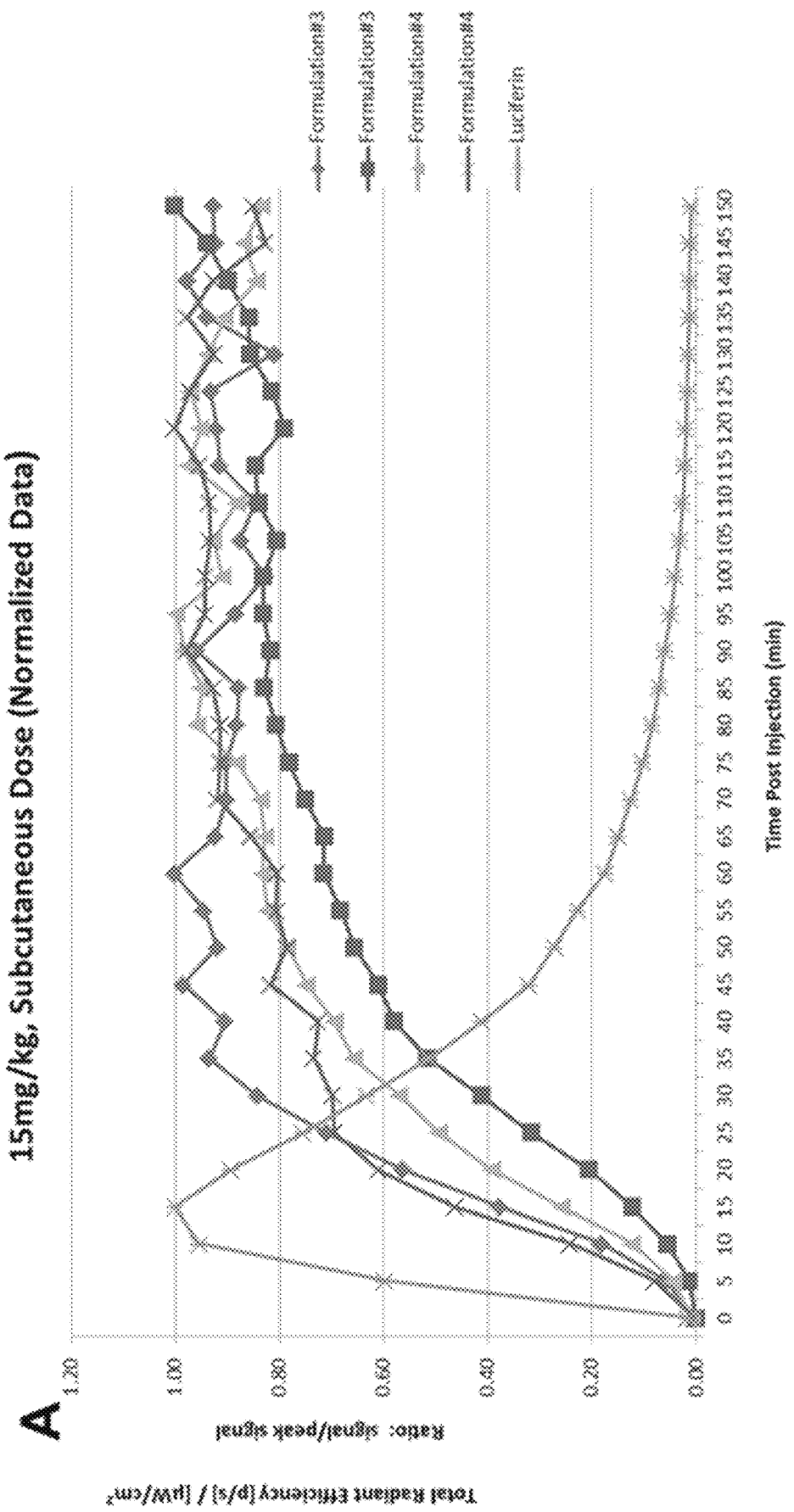
FIG. 13A is a graphical illustration showing in vivo kinetics of NanoLuc-DiR compared to free luciferin, normalized to peak signal flux vs. time plot following subcutaneous injection of NanoLuc-DiR and free luciferin.
Figure 13B:
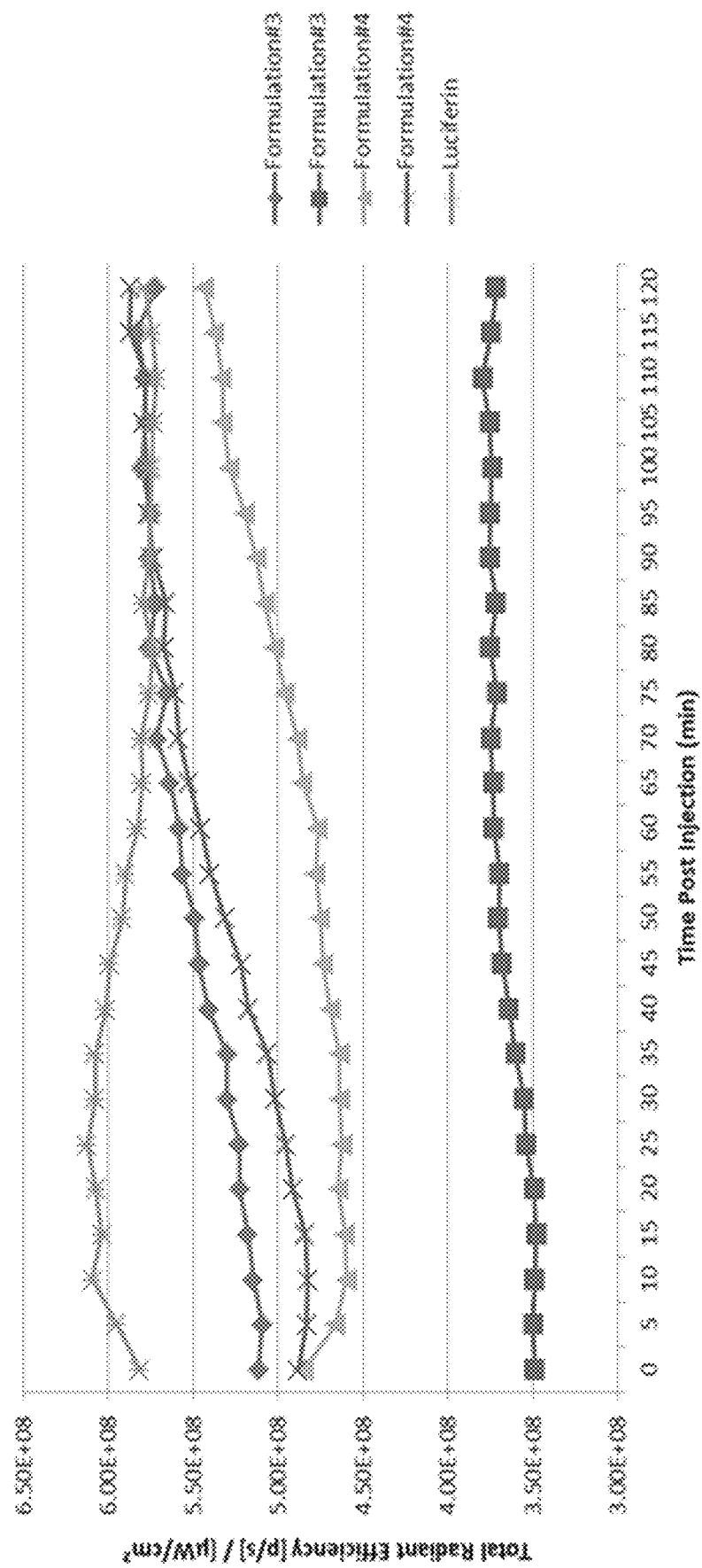
FIG. 13B is a graphical illustration showing in vivo kinetics of NanoLuc-DiR compared to free luciferin, total flux of fluorescence vs. time plot following dose of Nano-Luc-DiR.

The multimodality (Spectrum CT/FLIT/DLIT) imaging of 4T1-luc tumor model was visualized using 3D construct of tumor and mice, followed by administration of NanoLuc-DiR. A similar trend was observed with respect to luciferin release and expression of bioluminescence intensities from NanoLuc-DiR formulations (FIG. 13A) as compared to Nano-Luc. Additionally, florescence intensities were steady over the period of time (FIG. 13B).

Discussion

Luciferase reporters are established to analyze molecular and cellular events with simple, cost-effective, extremely sensitive and non-invasive method to image biologic processes in vivo (37) using bioluminescence imaging (38). Luciferin (e.g., a firefly luciferase substrate) is an amphipathic molecule with a relatively short half-life of 5.33 min (25) and permeability co-efficient of $3.6 \times 10^{-9}$ cm·s$^{-1}$ (25). Due to the faster clearance of luciferin from plasma and limitation of multiple injections of luciferin (25), the foregoing study proposed controlled sustained release of luciferin with effective radiance for imaging over the period of 24 hr.

For the formulation of luciferin as Nano-Luc, Monosteol™ and Precirol™ were found to be the most suitable lipids due to the higher solubility and partitioning. High amounts of mono-, di-, and triglycerides present in lipids help the drug to solubilize in the lipid fraction. Miglyol provides additional space for drug molecules to get entrapped, thus enhancing drug loading (39).

For the optimization of Nano-Luc, response surface experimental design showed a significant correlation between dependent and independent factors. Quadratic model was found to be the most suitable for defining the relationship for all the responses (model F value <0.05; lack of fit value >0.05 as per one-way ANOVA). Central composite design showed correlation between lipid concentrations and response variable entrapment efficiency, loading efficiency and release of luciferin from Nano-Luc.

Figure 14:
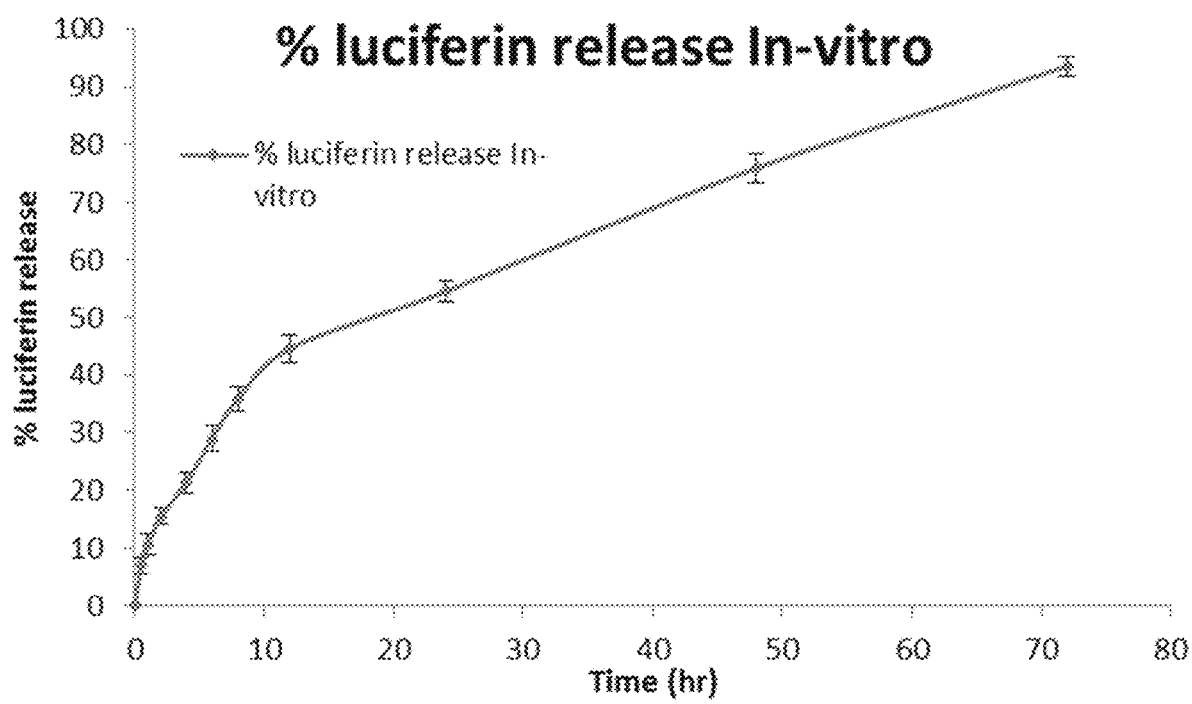
FIG. 14 is a graphical illustration showing the release rate profile of luciferin from Nano-Luc in vitro.

After the analysis of data, optimization using DOE Vr 8.0.7 software was performed to get a particle size of less than 200 nm with maximum entrapment efficiency and loading efficiency with 50 percent drug release at 24 hr. The intention behind these particular selections was to provide controlled sustained release of luciferin. FIG. 14 depicts the release rate of luciferin from Nano-Luc in in vitro conditions over time.

Using these criteria, the three variables were then combined to determine an overall optimum design. FIGS. 5A-5D show an acceptable region that describes the requirements of these responses. This optimum region could therefore be used to construct the design space of Nano-Luc with high quality characteristics. A further central composite design optimization and validation process was then undertaken using desirable characteristics (FIGS. 7A and 7B) that depended on the prescriptive criteria of maximum entrapment efficiency, maximum loading efficiency and release rate.

The DSC thermograms of Monosteol™, Miglyol™, Precirol™ and Nano-Luc were represented in FIGS. 8A-8F. The DSC study concluded with the absence of any chemical interaction between luciferin and excipient. The luciferin endothermic peak was not observed in the DSC thermogram of Nano-Luc, likely at least in part because of the molecular inclusion of luciferin in the lipid matrix.

Similar results have been reported earlier by other researchers (40-41). Puglia et al. (42) observed that the addition of ketoprofen or naproxen to the lipid formulations resulted in the broadening of the lipid endothermic peak. DSC thermograms of Nano-Luc showed broadening of lipid peak, and the reasons for this observation may be (1) the excipients undergoing several heating and cooling cycles, (2) the smaller size of the particles contributing to a larger surface area, and (3) Miglyol™, luciferin and surfactant behaving as impurities.

It was found that entrapment efficiency of nanoparticulate formulation was not changed drastically during stability studies, indicating that the formulation was stable at specified storage condition up to one month. The stability data indicated that the lipids have contributed to the stabilization of the formulation and could be useful for improving the shelf life of Nano-Luc. This might be attributed to the fact that transformation of colloidal suspension into solid form has the advantages of preventing particle aggregation, degradation reactions (hydrolysis), and leakage of the drug. Furthermore, the shelf-life of Nano-Luc estimated at 25° C. was more than ten months, while at 8° C. it was more than two years.

To evaluate the in vivo effectiveness of Nano-Luc, nanoparticles were administrated via SC, IP and IV route into mice having tumor expressing luciferase. Free luciferin cleared rapidly (within 60 min) with a biphasic time course. Luciferin encapsulated in Nano-Luc remained in the system giving radiance enough for imaging for more than 24 hr. For a period of 20 min, Nano-Luc formulations demonstrated an early and rapid release similar to free luciferin by IV administration. On the contrary, SC and IP administration of Nano-Luc demonstrated slow release of luciferin in vivo compared to free luciferin, with peak intensity lower than that of free luciferin. This phenomenon was also observed by Gross et al (21) for osmotic pump delivery of luciferin.

Table 6 illustrates the significant differences between certain embodiments of the current invention and the research disclosed in Kheirolomoom et al. (25) and Gross et al. (21).

TABLE 6

Comparison of the current methodology with the conventional methodologies of Kheirolomoom et al. (25) and Gross et al. (21).

| | Nano-Luc | Luciferin liposome (Kheirolomoom et al.) | Luciferin Osmotic pump (Gross et al.) |
|---|---|---|---|
| Method of preparation | Hot-melt homogenization at high speed followed by few cycles of high pressure homogenization | Thin lipid film hydration followed by extrusion | Micro-osmotic pumps (Alzet Model 1007D, 0.5 µL/h release rate, 100 µL reservoir; Durect, Cupertino, CA) were loaded with d-luciferin (50 mg/mL in sterile phosphate-buffered saline [PBS]) under aseptic conditions according to the manufacturer's instructions |
| Delivery method | Intravenous, intra-peritoneal, subcutaneous | Intra-tumoral, intravenous | Surgically implanted (subcutaneously) in the dorsal neck fat pad |
| Components | Luciferin, solid lipid, oil (liquid lipid) e.g. miglyol, monosteol, precirol, etc. | Luciferin, pH buffers, solid lipid, polyethylene glycol, e.g., DPPC, lyso-palmitoyl PC, DSPE-PEG2k, SoyPC, cholesterol | Luciferin and sterile phosphate-buffered saline |
| Luciferin loading type/ efficiency | Passive loading: 2-10 mg/ml; or 50-250 ug/mg of lipid | Passive loading: max 28.8 ug/mg of lipid Active loading: max 172 ug/mg of lipid | 100 µL of 50 mg/mL Luciferin: |
| Encapsulation/ Entrapment efficiency of luciferin | >98% | 90-95% | N/A |

Apart from these differences and the advantages of the current invention that are readily apparent, bioluminescence kinetics was steady over the period of 4 hr utilizing embodiments of the current invention at peak flux, while the kinetic profile of the liposomes shows no steady flux but steady decrease in luciferin kinetics (Kheirolomoom et al. (25)). Additionally, as described previously, imaging with embodiments of the current invention was possible over 24 hr, while with liposomes in Kheirolomoom et al. (25), imaging was possible over 12 hr.

The osmotic pump delivery disclosed in Gross et al. (21) showed release and imaging possible for 48 hr; however, raw bioluminescence compared to free luciferin was 70-150 folds lower with the osmotic pump. Moreover, the bioluminescence signal was not steady in photon count, while with embodiments of the current invention provide a steady bioluminescence signal for 4 hr.

Regarding preparation for administration, Kheirolomoom et al. (25) requires local hyperthermia to be induced with ultrasound to heat the tumor area at 42° C., in order to increase the raw bioluminescence radiance. Overall, in Kheirolomoom et al. (25), without hyperthermia, radiance was about 75 times lower relative to free luciferin; with hyperthermia, radiance was still about 25 times lower relative to free luciferin. It was found that radiance was only about 10 times lower relative to free luciferin when utilizing the current methodology. The liposome's raw bioluminescence with hyperthermia in Kheirolomoom et al. (25) at equivalent molar concentration of luciferin was about 30-50% lower than that of Nano-Luc without using any local hyperthermia.

With IV administration, flux efficiency of Nano-Luc luciferin was higher than that of free luciferin, which may be due to faster clearance of free luciferin from the system than Nano-Luc. This rapid release of luciferin was followed by a slow release in the second phase, which was more likely the release of the encapsulated luciferin. The early rapid release observed for luciferin in Nano-Luc likely results from the total luciferin that was initially associated with the outer core of Nano-Luc (39).

Whereas the osmotic pump delivery approach by Gross et al (21) requires surgical implantation of device, the current methodology can be performed by simple injection via SC, IP, or IV route.

As per Kheirolomoom et al (25), intravenously injected long circulating luciferin liposomes provided sufficient radiance for more than 12 hr of imaging, while Nano-Luc provided sufficient radiance for 24 hr. Also, in vivo kinetics for the liposome showed declining phase from time of injection as per Kheirolomoom et al (25) and never showed steady phase in luciferin kinetics, further illustrating the low level of raw bioluminescence radiance. In contrast, Nano-Luc showed steady kinetics for about 2 hr and started slowly declining over the remaining period, as seen in FIG. 12C.

Additionally, the multimodal imaging approach using NanoLuc-DiR—including bioluminescence radiance, fluorescence intensity and spectral imaging—has permitted evaluation of the imaging of tumor modality using IVIS® spectrum CT/FLIT/DLIT. The application of this approach can be varied with different parameters. For example, an alternative method permits assessments of targeted therapeutic efficacy while monitoring tumor regression during treatment in vivo. This is in contrast to conventional tumor measurements at the termination of treatment periods. Overall, embodiments of the current invention can significantly shorten the time required for assessing preclinical efficacy.

Further, it enables screening of drug/nanoparticle localization in tumors in vivo with high resolution, quantitatively and specifically. This may be a useful approach to screen a panel of new nano-therapeutics in vivo in order to select an effective nano-therapeutic for further testing of therapeutic efficacy. The characterization of nano-therapeutic particles in vivo would involve attachment of fluorophores to particles to visualize the localization in vivo. Whether the molecules of interest are inherently fluorescent (Xenolight DiR) or labeled with a fluorophore, the multimodality imaging method described herein can provide a powerful approach for characterizing nanoparticle activities in vivo in preclinical studies.

The foregoing study exemplified the development and evaluation of nanoparticles of an in vivo imaging agent luciferin. The prepared Nano-Luc was optimized for its formulation and in vitro parameters. Accelerated stability assessment of prepared Nano-Luc shows the potential of the nanoparticle in protection of the entrapped drug. The calculated shelf life of Nano-Luc was found to be more than 10 months at 25° C. Nano-Luc delivered luciferin over a relatively lengthy period of time, expressing sufficient bioluminescence radiance (within tumors) for more than 24 hours of imaging when administered by IP, SC, or IV to mice expressing luciferase. Nano-Luc kinetic studies revealed a steady and longer release of luciferin when encapsulated as compared to free luciferin. Furthermore, NanoLuc-DiR showed possibility of tumor multimodality imaging, as well as its use for characterizing nanoparticle activities in vivo in preclinical studies.

REFERENCES

1. Di Carli M F, Dorbala S, Meserve J, El Fakhri G, Sitek A, Moore S C. Clinical myocardial perfusion PET/C T. J Nucl Med. 2007 May; 48 (5): 783-93.
2. Mosconi L, Tsui W H, Herholz K, Pupi A, Drzezga A, Lucignani G, et al. Multicenter standardized 18F-FDG PET diagnosis of mild cognitive impairment, Alzheimer's disease, and other dementias. J Nucl Med. 2008 March; 49 (3): 390-8.
3. Zhao B, Schwartz L H, Larson S M. Imaging surrogates of tumor response to therapy: anatomic and functional biomarkers. J Nucl Med. 2009 February; 50 (2): 239-49.
4. Hillner B E, Liu D, Coleman R E, Shields A F, Gareen I F, Hanna L, et al. The National Oncologic PET Registry (NOPR): design and analysis plan. J Nucl Med. 2007 November; 48 (11): 1901-8.
5. Hargreaves R J. The role of molecular imaging in drug discovery and development. Clin Pharmacol Ther. 2008 February; 83 (2): 349-53.
6. Niu G, Chen X. Has molecular and cellular imaging enhanced drug discovery and drug development? Drugs R D. 2008; 9 (6): 351-68.
7. Willmann J K, van Bruggen N, Dinkelborg L M, Gambhir S S. Molecular imaging in drug development. Nat Rev Drug Discov. 2008 Jul.; 7 (7): 591-607.
8. Cho H, Ackerstaff E, Carlin S, Lupu M E, Wang Y, Rizwan A, et al. Noninvasive multimodality imaging of the tumor microenvironment: registered dynamic magnetic resonance imaging and positron emission tomography studies of a preclinical tumor model of tumor hypoxia. Neoplasia. 2009 March; 11 (3): 247-59, 2p following 59.
9. Hayashi D, Tkacz J N, Hammond S, Devenney-Cakir B C, Zaim S, Bouzegaou N, et al. Gastroenteropancreatic neuroendocrine tumors: multimodality imaging features with pathological correlation. Jpn J Radiol. 2011 February; 29 (2): 85-91.
10. Cai W, Chen X. Multimodality molecular imaging of tumor angiogenesis. J Nucl Med. 2008 June; 49 Suppl 2: 113S-28S.
11. Zinn K R, Chaudhuri T R, Szafran A A, O'Quinn D, Weaver C, Dugger K, et al. Noninvasive bioluminescence imaging in small animals. ILAR J. 2008; 49 (1): 103-15.
12. Sadikot R T, Blackwell T S. Bioluminescence imaging. Proc Am Thorac Soc. 2005; 2 (6): 537-40, 11-2.
13. Badr C E, Tannous B A. Bioluminescence imaging: progress and applications. Trends Biotechnol. 2011 Dec.; 29 (12): 624-33.
14. Zhang N, Lyons S, Lim E, Lassota P. A spontaneous acinar cell carcinoma model for monitoring progression of pancreatic lesions and response to treatment through noninvasive bioluminescence imaging. Clin Cancer Res. 2009 Aug. 1; 15 (15): 4915-24.
15. Zhang W, Feng J Q, Harris S E, Contag P R, Stevenson D K, Contag C H. Rapid in vivo functional analysis of transgenes in mice using whole body imaging of luciferase expression. Transgenic Res. 2001 October; 10 (5): 423-34.
16. Lim E, Modi K D, Kim J. In vivo bioluminescent imaging of mammary tumors using IVIS spectrum. J Vis Exp. 2009 (26).
17. Bhaumik S, Gambhir S S. Optical imaging of *Renilla* luciferase reporter gene expression in living mice. Proc Natl Acad Sci USA. 2002 Jan. 8; 99 (1): 377-82.
18. Frackman S, Anhalt M, Nealson K H. Cloning, organization, and expression of the bioluminescence genes of Xenorhabdus *luminescens*. J Bacteriol. 1990 October; 172 (10): 5767-73.
19. Siragusa G R, Nawotka K, Spilman S D, Contag P R, Contag C H. Real-time monitoring of *Escherichia coli* O157: H7 adherence to beef carcass surface tissues with a bioluminescent reporter. Appl Environ Microbiol. 1999 April; 65 (4): 1738-45.
20. Zhao H, Doyle T C, Coquoz O, Kalish F, Rice B W, Contag C H. Emission spectra of bioluminescent reporters and interaction with mammalian tissue determine the sensitivity of detection in vivo. J Biomed Opt. 2005 Jul.-Aug.; 10 (4): 41210.
21. Gross S, Abraham U, Prior J L, Herzog E D, Piwnica-Worms D. Continuous delivery of D-luciferin by implanted micro-osmotic pumps enables true real-time bioluminescence imaging of luciferase activity in vivo. Mol Imaging. 2007 Mar.-Apr.; 6 (2): 121-30.
22. Hiler D J, Greenwald M L, Geusz M E. Imaging gene expression in live transgenic mice after providing luciferin in drinking water. Photochem Photobiol Sci. 2006 Nov.; 5 (11): 1082-5.
23. Berger F, Paulmurugan R, Bhaumik S, Gambhir S S. Uptake kinetics and biodistribution of 14C-D-luciferin—a radiolabeled substrate for the firefly luciferase catalyzed bioluminescence reaction: impact on bioluminescence based reporter gene imaging. Eur J Nucl Med Mol Imaging. 2008 December; 35 (12): 2275-85.
24. Gross S, Piwnica-Worms D. Real-time imaging of ligand-induced IKK activation in intact cells and in living mice. Nat Methods. 2005 August; 2 (8): 607-14.
25. Kheirolomoom A, Kruse D E, Qin S, Watson K E, Lai C Y, Young L J, et al. Enhanced in vivo bioluminescence imaging using liposomal luciferin delivery system. J Control Release. 2010 Jan. 25; 141 (2): 128-36.
26. Souto E B, Wissing S A, Barbosa C M, Muller R H. Development of a controlled release formulation based on SLN and NLC for topical clotrimazole delivery. Int J Pharm. 2004 Jun. 18; 278 (1): 71-7.
27 Kakkar V, Muppu S K, Chopra K, Kaur I P. Curcumin loaded solid lipid nanoparticles: an efficient formulation approach for cerebral ischemic reperfusion injury in rats. Eur J Pharm Biopharm. 2013 Feb. 26.
28. Muller R H, Radtke M, Wissing S A. Nanostructured lipid matrices for improved microencapsulation of drugs. Int J Pharm. 2002 Aug. 21; 242 (1-2): 121-8.
29. Corn D J, Kim Y, Krebs M D, Mounts T, Molter J, Gerson S, et al. Imaging Early Stage Osteogenic Differentiation of Mesenchymal Stem Cells. J Orthop Res. 2013 Feb. 25.
30 Zhang G J, Chen T B, Davide J, Tao W, Vanko A, Connolly B, et al. Visualization of Mitotic Arrest of Cell Cycle with Bioluminescence Imaging in Living Animals. Mol Imaging Biol. 2013 Feb. 26.
31. Pardeike J, Hommoss A, Muller R H. Lipid nanoparticles (SLN, NLC) in cosmetic and pharmaceutical dermal products. Int J Pharm. 2009 Jan. 21; 366 (1-2): 170-84.

32. Singh B, Bhatowa R, Tripathi C B, Kapil R. Developing micro-/nanoparticulate drug delivery systems using "design of experiments". Int J Pharm Investig. 2011 April; 1 (2): 75-87.

33. Xiang Q Y, Wang M T, Chen F, Gong T, Jian Y L, Zhang Z R, et al. Lung-targeting delivery of dexamethasone acetate loaded solid lipid nanoparticles. Arch Pharm Res. 2007 April; 30 (4): 519-25.

34. Singh A, Ahmad I, Akhter S, Jain G K, Iqbal Z, Talegaonkar S, et al. Nanocarrier based formulation of Thymoquinone improves oral delivery: Stability assessment, in vitro and in vivo studies. Colloids and Surfaces B: Biointerfaces. 2013; 102 (0): 822-32.

35. Lim E, Modi K, Christensen A, Meganck J, Oldfield S, Zhang N.

Monitoring tumor metastases and osteolytic lesions with bioluminescence and micro CT imaging. J Vis Exp. 2011 (50).

36. Hao J, Wang F, Wang X, Zhang D, Bi Y, Gao Y, et al. Development and optimization of baicalin-loaded solid lipid nanoparticles prepared by coacervation method using central composite design. Eur J Pharm Sci. 2012 Sep. 29; 47 (2): 497-505.

37. Contag C H, Ross B D. It's not just about anatomy: in vivo bioluminescence imaging as an eyepiece into biology. J Magn Reson Imaging. 2002 October; 16 (4): 378-87.

38. Gross S, Piwnica-Worms D. Spying on cancer: molecular imaging in vivo with genetically encoded reporters. Cancer Cell. 2005 January; 7 (1): 5-15.

39. Patlolla R R, Chougule M, Patel A R, Jackson T, Tata P N, Singh M. Formulation, characterization and pulmonary deposition of nebulized celecoxib encapsulated nanostructured lipid carriers. J Control Release. 2010 Jun. 1; 144 (2): 233-41.

40. Schwarz C, Mehnert W. Freeze-drying of drug-free and drug-loaded solid lipid nanoparticles (SLN). Int J Pharm. 1997 Nov. 28; 157 (2): 171-9.

41. Venkateswarlu V, Manjunath K. Preparation, characterization and in vitro release kinetics of clozapine solid lipid nanoparticles. J Control Release. 2004 Mar. 24; 95 (3): 627-38.

42. Puglia C, Blasi P, Rizza L, Schoubben A, Bonina F, Rossi C, et al. Lipid nanoparticles for prolonged topical delivery: an in vitro and in vivo investigation. Int J Pharm. 2008 Jun. 5; 357 (1-2): 295-304.

Definitions of Claim Terms

Bio-imaging agent: This term is used herein to refer to a molecule that emits a contrast signal, such as the emission of light or color, when catalyzed or on its own. Emission of this contrast signal allows the site, where the bio-imaging agent has been catalyzed, to be imaged in vivo. Various types of bio-imaging agents are contemplated, for example fluorescent dyes, bioluminescent agents, chemi-luminescent agents, carbon nanotubes, metal nanoparticles/nanotubes (e.g., gold, silver, rare metals, selenium, etc.), non-metallics (e.g., silica, porous silica, etc.), gas (e.g., perfluorocarbon, nitrogen, etc.), radio-isotopes, phosphate-based compounds (e.g., disodium etidronate, tin pyrophosphate, polyphosphate4 and sodium trimetaphosphate, etc.), among others.

Effective, detectable biofluorescence: This term is used herein to refer to a contrast signal emitted from the target, wherein the signal has a strength that can be detected using known imaging techniques, for example radiography, MRI, nuclear medicine, photo-acoustic imaging, tomography, and ultrasound, among others.

Enhanced half-life: This term is used herein to refer to an increase in the amount of time required for the concentration of a particular reactant to fall from a specific value to half of that specific value. An increased half-life of a reactant would allow that reactant to have a certain effect over a greater period of time. For example, if the in vivo half-life of luciferin is enhanced or increased, one would be able to conduct in vivo bio-imaging for a greater period of time.

Entrapment efficiency: This term is used herein to refer to the ratio of the amount of an active agent (drug) actually encapsulated within a carrier to the amount of that active agent (drug) that was added. A higher entrapment efficiency would typically be desired, as that would indicate a high percentage of active agent added became encapsulated within the carrier, as desired.

Ingredient: This term is used herein to refer to any substance used to formulate and fabricate a nanoparticle carrier as described herein. Examples include, but are not limited to, lipids, metals, polymers, and carbon nanotubes, alone or in combination.

Loading efficiency: This term is used herein to refer to the ratio of the amount of an active agent (drug) in a carrier system to the total weight of that carrier system. A higher loading efficiency would typically be desired, so long as the overall system was effective in its purpose.

Optimized: This term is used herein to refer to an entity, or an aspect thereof, having the most favorable or desirable qualities. There can be a cause and effect relationship between two aspects of an entity, such that optimizing one aspect would cause the other aspect to have the most favorable or desirable qualities. For example, the ratio of ingredients in a nanoparticle carrier should be optimized to allow for maximum entrapment and loading efficiencies, along with a desired release rate. The optimal ratio of ingredients would depend, in part, on the type of ingredients used and the effects desired in the resulting nanoparticle carrier.

Predetermined ratio: This term is used herein to refer to a proportion of the amount of solid phase ingredients used to fabricate a nanoparticle carrier to the amount of liquid phase ingredients used to fabricate that nanoparticle carrier. This ratio is important in that it determines characteristics of the resulting nanoparticle carrier, for example the nanoparticle carrier's entrapment efficiency, loading efficiency, and release rate of the bio-imaging agent or other active substance.

Release rate: This term is used herein to refer to the rate at which an active agent (drug) is released from within its corresponding carrier. Once released, that active agent (drug) can have its intended effects on its target. A desired release rate would depend on the ultimate goal. For example, a drug may be desired to be released all at once after a certain period of time. Alternatively, a drug may be desired to be released constantly and consistently throughout a certain period of time. With bio-imaging, typically one would want the agent to be released constantly throughout the imaging period, so that the target can be imaged throughout the imaging period.

Stable: This term is used herein to refer to the thermodynamic characteristic of a substance or entity being consistent or difficult to modify chemically. Thus, if solid phase and liquid phase ingredients have a predetermined ratio that is stable, then the resulting mixture of the ingredients (e.g., a nanoparticle carrier) would be difficult to modify chemically (e.g., melting, freezing, inactivating, destabilizing, etc.).

Subject: This term is used herein to refer to any animate or inanimate animal body that is submitted to the system and/or method of the current invention, or any aspect thereof. Wide ranges of subjects are contemplated, and examples include, but are not limited to, vertebrate animals, human beings, primates, mice, etc.

Target: This term is used herein to refer to a specific structure that one desires to image and thus should be sufficiently biofluorescent to be imaged. This structure can be natural, such as an internal organ in a human being, or can be artificial, such as tumor cells injected into a mouse.

Target-honing molecule: This term is used herein to refer to a target specifier that enhances delivery of a drug by directing the drug (and the corresponding carrier) to a particular target or goal. This can be accomplished, for example, by the molecules having tags with only specific binding regions that correlate to the target cell type of interest. An example of a target-honing molecule is the CREKA peptide, which targets tumor cells in the body. Thus, this type of target-honing molecule can be called a tumor-honing molecule. Various classes of target-honing molecules are contemplated, for example peptides, proteins, RNA, DNA, SiRNA, etc.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of delivering an active substance or agent to a target within a subject for medical and preclinical imaging, comprising:
   providing at least one nanoparticle to the subject wherein the at least one nanoparticle carrier comprising
      about 700 mg of at least one solid phase lipid selected from the group consisting of propylene glycol palmitostearate, glyceryl palmitostearate, and combinations thereof;
      about 330 mg of at least one liquid phase lipid or oil selected from the group consisting of caprylic/capric triglycerides, medium chain triglycerides, diethylene glycol monoethyl ether, and combinations thereof; and
      about 480 µl of at least one surfactant selected from the group consisting of polyoxyethylene sorbitan monolaurate, polyoxyethylene sorbitan monooleate, and a combination thereof;
   encapsulating an active pharmaceutical agent within the at least one nanoparticle;
   encapsulating a luciferin within the at least one nanoparticle;
   conjugating a target-honing molecule to a surface of the at least one nanoparticle to form a nanoparticle delivery system; and
   administrating the nanoparticle delivery system to the subject;
   wherein biofluorescence of the luciferin occurs as a steady release for up to about 4 hours after intravenous administration of the nanoparticle delivery system to the subject; and
   wherein the biofluorescence of the luciferin is detectable in the subject for at least 24 hours after intravenous administration of the nanoparticle delivery system to the subject.

2. The method of claim 1, wherein release rate of the luciferin is about 50% at 24 hours after intravenous administration with at least 92% encapsulation efficiency.

3. The method of claim 1, wherein the nanoparticle delivery system is less than about 200 nm in size.

4. The method of claim 1, wherein the at least one liquid phase lipid is the caprylic/capric triglyceride.

5. The method of claim 1, wherein the pharmaceutical agent is 1,1-bis(3' indolyl)-1-(p-biphenyl) methane (DIM-C-pPhC6H5).

6. The method of claim 1, wherein the target-honing molecule targets a tumor in the subject.

7. The method of claim 6, wherein the target-honing molecule is a CREKA peptide.

8. The method of claim 1, wherein the nanoparticle delivery system is formed by hot melt homogenization followed by high pressure homogenization.

* * * * *